US009950018B2

(12) United States Patent
Shin et al.

(10) Patent No.: US 9,950,018 B2
(45) Date of Patent: Apr. 24, 2018

(54) BACTERIOPHAGE AND COMPOSITION COMPRISING SAME

(71) Applicant: CJ CHEILJEDANG CORPORATION, Seoul (KR)

(72) Inventors: Eun Mi Shin, Seoul (KR); Gi Duk Bae, Seoul (KR); Jae Won Kim, Yongin-si (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 15/304,489

(22) PCT Filed: Mar. 13, 2015

(86) PCT No.: PCT/KR2015/002472

§ 371 (c)(1),
(2) Date: Oct. 14, 2016

(87) PCT Pub. No.: WO2015/160089

PCT Pub. Date: Oct. 22, 2015

(65) Prior Publication Data

US 2017/0035817 A1 Feb. 9, 2017

(30) Foreign Application Priority Data

Apr. 15, 2014 (KR) ........................ 10-2014-0044996

(51) Int. Cl.

| | |
|---|---|
| ***C12N 7/00*** | (2006.01) |
| ***A61K 35/76*** | (2015.01) |
| ***A23K 20/195*** | (2016.01) |
| ***A23K 20/10*** | (2016.01) |
| ***A01N 63/00*** | (2006.01) |

(Continued)

(52) U.S. Cl.

CPC .............. *A61K 35/76* (2013.01); *A01N 63/00* (2013.01); *A23K 20/10* (2016.05); *A23K 20/195* (2016.05); *A23L 2/52* (2013.01); *A61K 9/0053* (2013.01); *C11D 3/381* (2013.01); *C11D 3/48* (2013.01);

(Continued)

(58) Field of Classification Search

None

See application file for complete search history.

(56) References Cited

U.S. PATENT DOCUMENTS 8,021,657 B2 9/2011 Bruessow et al.

FOREIGN PATENT DOCUMENTS

| | | |
|---|---|---|
| CN | 101724607 A | 6/2010 |
| KR | 10-2011-0041670 A | 4/2011 |

(Continued)

OTHER PUBLICATIONS

Blast: search results for 10k of SEQ ID No. 1. Also see search notes. (Year: 2017).*

(Continued)

*Primary Examiner* — Michelle S Horning

(74) *Attorney, Agent, or Firm* — Knobbe Martens Olson & Bear LLP

(57) ABSTRACT

The present invention relates to a novel bacteriophage ΦCJ27 (KCCM11465P) and a composition containing the same as an active ingredient. Further, the present invention relates to a method for preventing and/or treating infective diseases caused by enterotoxic *Escherichia coli* (ETEC) of non-human animals using the ΦCJ27 (KCCM11465P) and the composition.

11 Claims, 3 Drawing Sheets

(51) Int. Cl.
*A23L 2/52* (2006.01)
*A61K 9/00* (2006.01)
*C11D 3/38* (2006.01)
*C11D 3/48* (2006.01)

(52) U.S. Cl.
CPC ............ *C12N 7/00* (2013.01); *A23V 2002/00* (2013.01); *C12N 2795/00021* (2013.01)

(56) References Cited

FOREIGN PATENT DOCUMENTS

| | | | |
|---|---|---|---|
| KR | 10-1101376 | B1 | 1/2012 |
| KR | 10-1260645 | B1 | 5/2013 |
| KR | 10-1381793 | B1 | 4/2014 |
| KR | 10-1381795 | B1 | 4/2014 |
| KR | 10-1381797 | B1 | 4/2014 |
| KR | 10-1381798 | B1 | 4/2014 |
| WO | 2013/073843 | A1 | 5/2013 |
| WO | 2013/157813 | A1 | 10/2013 |

OTHER PUBLICATIONS

International Search Report dated Jun. 19, 2015 of PCT/KR2015/002472 which is the parent application and its English translation—5 pages.

Notice of Allowance dated Jan. 21, 2016 of corresponding Korean Patent Application No. 10-2014-0042911—2 pages.

Office Action dated Jul. 18, 2017 of corresponding Japanese Patent Application No. 2016-561675—4 pages.

Cha et al., "Effect of Bacteriophage in Enterotoxigenic *Escherichia coli* (ETEC) Infected Pigs", 2012, Journal of Veterinary Medical Science, vol. 74, Issue 8, pp. 1037-1039.

Dini et al., "Isolation and Selection of Coliphages as Potential Biocontrol Agents of Enterohemorrhagic and Shiga Toxin-producing *E. coli* (EHEC and STEC) in Cattle", Journal of Applied Microbiology, 2010, vol. 109, pp. 873-887.

Jamalludden et al., Isolation and Characterization of Nine Bacteriophages that lyse O149 Enterotoxigenic *Escherichia Coli*, Veterinary Microbiology, 2007, vol. 124, pp. 47-57.

NCBI, GenBank Accession No. KF582788.1, Apr. 2, 2014.

Extended European Search Report dated Nov. 28, 2017 in corresponding European Patent Application No. 15780499.8—9 pages.

Endersen et al., "Phage Therapy in the Food Industry", Annual Review of Food Science and Technology, Jan. 9, 2014, vol. 5, No. 1, pp. 327-349.

Kim et al., "Evaluation of bacteriophages for prevention and treatment of diarrhea due to experimental enterotoxigenic *Escherichia coli* K88 infection of weaned piglets", Korean J. Vet. Serv., 2011, vol. 34, Issue 4, pp. 341-352.

Bourdin et al., "Coverage of diarrhoea-associated *Escherichia coli* isolates from different origins with two types of phage cocktails", Microbial Biotechnology, 2014, vol. 7, pp. 165-176.

Jamalludeen et al., "Evaluation of bacteriophages for prevention and treatment of diarrhea due to experimental enterotoxigenic *Escherichia coli* O149 infection of pigs", Veterinary Microbiology, 2009, vol. 136, pp. 135-141.

Yan et al., "Effect of Bacteriophage Supplementation on the Growth Performance, Nutrient Digestibility, Blood Characteristics, and Fecal Microbial Shedding in Growing Pigs", Asian-Aust. J. Anim. Sci., Oct. 2012, vol. 25, No. 10, pp. 1451-1456.

Brussow, "Phage therapy: the *Escherichia coli* experience", Microbiology, 2005, vol. 151, pp. 2133-2140.

Chan et al., "Phage cocktails and the future of phage therapy", Future Microbiology, 2013, vol. 8, No. 6, pp. 769-783.

* cited by examiner

【Fig. 1】
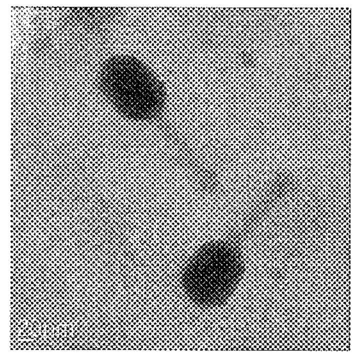
【Fig. 2】
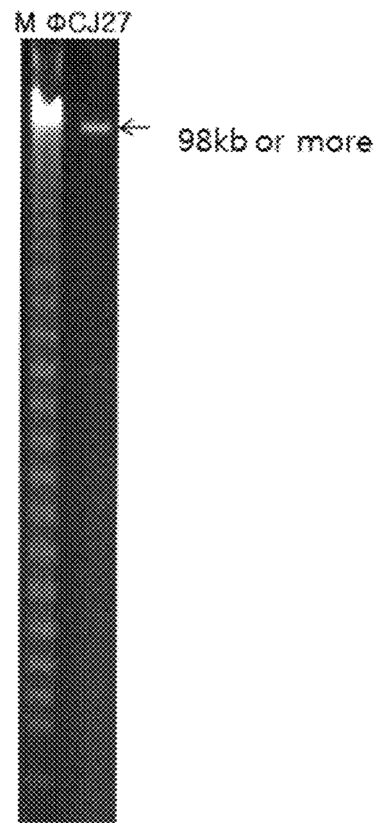

【Fig. 3】
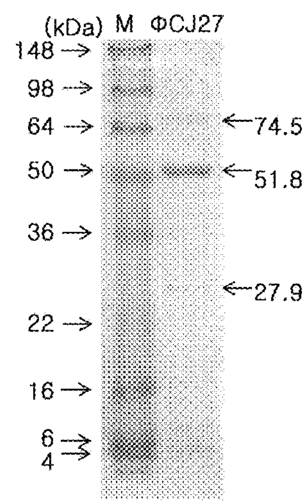
【Fig. 4】
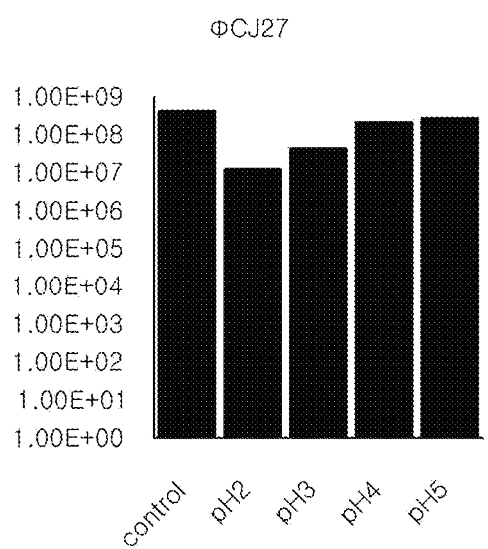

【Fig. 5】
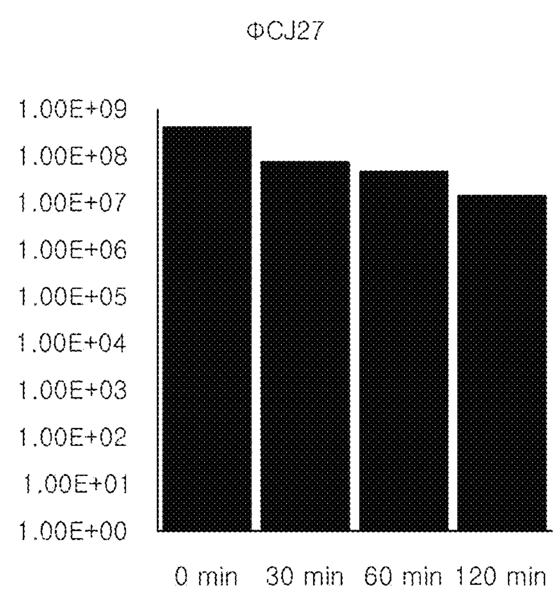

BACTERIOPHAGE AND COMPOSITION COMPRISING SAME

TECHNICAL FIELD

The present invention relates to a novel bacteriophage having a specific ability to kill enterotoxigenic *Escherichia coli* (ETEC), a composition including the same, and a method for preventing or treating infectious diseases of animals using the novel bacteriophage or the composition.

BACKGROUND ART

*Escherichia coli* (hereinafter also referred to as *E. coli*) is a Gram-negative, short rod bacterium of genus *Escherichia*, family Enterobacteriaceae, and one of normal flora found in intestines of various animals including mammals. Most strains of *E. coli* are non-pathogenic and can cause opportunistic infection, but some highly pathogenic strains cause various intestinal diseases and sepsis in animals including humans.

*Escherichia coli* can be classified into enterotoxigenic *Escherichia coli* (ETEC), enteropathogenic *Escherichia coli* (EPEC), enterohemorrhagic *Escherichia coli* (EHEC), enteroaggregative *Escherichia coli* (EAEC), enteroinvasive *Escherichia coli* (EIEC), necrotoxigenic *Escherichia coli* (NTEC), and the like, and particularly, enterotoxigenic *Escherichia coli* is known to cause infectious diseases in pigs.

Currently, with the trend toward large-scale group housing in pig farming, porcine colibacillosis has emerged as the most frequent and bothering disease in pig farms. Recently, outbreaks of porcine colibacillosis, which stunts piglet growth due to diarrhea and mortality, have been increasing in Korea, causing enormous economic loss to pig farmers.

For prevention and treatment of porcine colibacillosis, although various antibiotics have been applied to pigs in the related art, abuse or misuse of antibiotics can induce antibiotic resistance in pigs or can cause the antibiotics to remain in the pigs' body, leading to global restrictions on administration of antibiotics.

Meanwhile, a bacteriophage refers to a bacteria-specific virus capable of infecting a specific bacterium and preventing and inhibiting growth of the bacterium. As bacteriophages have stronger host specificity than antibiotics, and recent emergence of bacteria resistant to antibiotics and residual antibiotics in animals are growing problems, application of bacteriophages has drawn great interest.

Studies on bacteriophages have been actively performed in many countries, and there has been an increasing tendency to obtain approval from the Food and Drug Administration (FDA) for compositions using bacteriophages in addition to patent applications for bacteriophages.

However, bacteriophage related technologies for prevention and/or treatment of infectious diseases, which are important issues in the livestock industry including pig farming, due to enterotoxigenic *Escherichia coli* are still insufficient and therefore, there is a need for such bacteriophages and development of relevant technologies.

DISCLOSURE

Technical Problem

As a result of earnest investigation aimed at overcoming the emergence of bacteria resistant to antibiotics and residual antibiotics in animals and at effectively preventing and treating infectious diseases caused by *Escherichia coli*, the present inventors isolated a novel bacteriophage ΦCJ27 (KCCM11465P) having a specific ability to kill enterotoxigenic *Escherichia coli* from natural sources.

In addition, the present inventors identified morphological, biochemical, and genetic properties of the novel bacteriophage, confirmed that the bacteriophage has excellent acid resistance and heat resistance, and the like, and developed antibiotics, disinfectants, additives for feeds, other compositions, and the like using the bacteriophage, a composition for preventing or treating infectious diseases caused by *Escherichia coli*, and a method for preventing or treating diseases using the same.

It is an object of the present invention to provide a novel bacteriophage ΦCJ27 (KCCM11465P) having a specific ability to kill enterotoxigenic *Escherichia coli*.

It is another object of the present invention to provide a composition for preventing and/or treating infectious diseases caused by enterotoxigenic *Escherichia coli*, including the bacteriophage ΦCJ27 (KCCM11465P) as an active ingredient.

It is a further object of the present invention to provide antibiotics, additives for feeds, additives for drinking water, feeds, drinking water, disinfectants or detergents, including the bacteriophage ΦCJ27 (KCCM11465P) as an active ingredient.

It is yet another object of the present invention to provide a method for preventing and/or treating infectious diseases caused by enterotoxigenic *Escherichia coli* in a non-human animal using the bacteriophage ΦCJ27 (KCCM11465P) or the composition including the bacteriophage ΦCJ27 (KCCM11465P) as an active ingredient.

Technical Solution

One aspect of the present invention provides a novel bacteriophage ΦCJ27 (KCCM11465P) having a specific ability to kill enterotoxigenic *Escherichia coli*.

Another aspect of the present invention provides a composition for preventing or treating infectious diseases caused by enterotoxigenic *Escherichia coli*, including the bacteriophage ΦCJ27 (KCCM11465P) as an active ingredient.

A further aspect of the present invention provides antibiotics, additives for feeds, additives for drinking water, feeds, drinking water, disinfectants or detergents, including the bacteriophage ΦCJ27 (KCCM11465P) as an active ingredient.

Yet another aspect of the present invention provides a method for preventing and/or treating infectious diseases caused by enterotoxigenic *Escherichia coli*, including: administering the bacteriophage ΦCJ27 (KCCM11465P) or the composition including the bacteriophage ΦCJ27 (KCCM11465P) as an active ingredient to a non-human animal.

Advantageous Effects

The bacteriophage ΦCJ27 (KCCM11465P) according to the present invention has an effect of having a specific ability to kill enterotoxigenic *Escherichia coli*.

Further, the bacteriophage ΦCJ27 (KCCM11465P) according to the present invention has excellent acid resistance and heat resistance, and thus can be employed not only as an agent for preventing or treating infectious diseases caused by enterotoxigenic *Escherichia coli* at various ranges of temperature and pH, but also as antibiotics, additives for feeds, additives for drinking water, feeds, drinking water, disinfectants, detergents, and the like, including the bacteriophage ΦCJ27 (KCCM11465P) as an active ingredient.

Further, the present invention provides the bacteriophage ΦCJ27 (KCCM11465P) or antibiotics including the same as an active ingredient, and the antibiotics have effects in that the antibiotics have specificity for enterotoxigenic *Escherichia coli* as compared to prior antibiotics and thus selectively kill specific pathogenic bacteria without killing beneficial bacteria; and that the antibiotics do not induce antibiotic resistance, resulting in extension of lifetime of products as compared to prior antibiotics.

Further, the present invention has effects of preventing or treating infectious diseases caused by enterotoxigenic *Escherichia coli* by administering the bacteriophage ΦCJ27 (KCCM11465P) or the composition including the bacteriophage ΦCJ27 (KCCM11465P) as an active ingredient to a non-human animal.

DESCRIPTION OF DRAWINGS

FIG. 1 is an electron microscope image of a novel bacteriophage ΦCJ27 (KCCM11465P) (hereinafter referred to as 'ΦCJ27').

FIG. 2 shows results of pulsed field gel electrophoresis (PFGE) of a novel bacteriophage ΦCJ27.

FIG. 3 shows results of sodium dodecyl sulfate polyacrylamide gel electrophoresis (SDS-PAGE) of a novel bacteriophage CJ27.

FIG. 4 is a graph depicting results of acid resistance experiment of a novel bacteriophage ΦCJ27.

FIG. 5 is a graph depicting results of heat resistance experiment of a novel bacteriophage ΦCJ27 at 60° C.

EMBODIMENTS

Hereinafter, embodiments of the present invention will be described in more detail. Description of details apparent to a person having ordinary knowledge in the art will be omitted herein.

One embodiment of the present invention provides a novel bacteriophage ΦCJ27 (KCCM11465P) (hereinafter referred to as 'ΦCJ27') having a specific ability to kill enterotoxigenic *Escherichia coli* (ETEC).

Enterotoxigenic *Escherichia coli* is a Gram-negative bacillus and an aerobic or facultative anaerobic bacterium which decomposes lactose and fructose to generate acids and gases. Enterotoxigenic *Escherichia coli* grows well on common media and is capable of growing at a temperature of about 7° C. to about 48° C. with ideal growth temperature ranging from about 35° C. to about 37° C. Further, enterotoxigenic *Escherichia coli* can grow at pH ranging from pH 4.5 to pH 9.

Since enterotoxigenic *Escherichia coli* produces enterotoxins similar to those produced from *Vibrio cholera*, a patient infected with enterotoxigenic *Escherichia coli* exhibits symptoms similar to a patient infected with *Vibrio cholera*. The produced enterotoxins can be broadly classified into heat-labile enterotoxin (LT) and heat-stable enterotoxin (ST). The heat-labile enterotoxin loses its activity when heated at about 60° C. for about 10 minutes, whereas the heat-stable enterotoxin does not lose its activity when heated at about 100° C. for about 30 minutes.

Enterotoxigenic *Escherichia coli* proliferates in an upper portion of the small intestine, and when the concentration of enterotoxigenic *Escherichia coli* approaches about $10^7$ colony forming units (cfu) to about $10^8$ cfu per unit volume (1 ml) of intestinal juices, enterotoxigenic *Escherichia coli* can cause infectious diseases including colibacillosis caused by *Escherichia coli.*

A bacteriophage is a bacteria-specific virus capable of infecting a specific bacterium and inhibiting growth of the bacterium, and is a virus including single or double-stranded deoxyribonucleic acid (DNA) or ribonucleic acid (RNA) as a genetic material.

Specifically, the bacteriophage ΦCJ27 according to the embodiment of the present invention is a bacteriophage that has species specificity of selectively infecting enterotoxigenic pathogenic *Escherichia coli* and morphologically belongs to Myoviridae having an elongated head and a contractile tail (see FIG. 1).

Homology between a nucleotide sequence of the bacteriophage ΦCJ27 and decoded nucleotide sequences of other bacteriophages is compared and results are shown in Table 1. The bacteriophage ΦCJ27 shows stable acid resistance at pH 2.0 to pH 5.0 without losing activity (FIG. 4), and in terms of heat resistance, the bacteriophage ΦCJ27 shows activity decline of about 1 log or less when exposed to 60° C. for one hour (FIG. 5). DNA nucleotide sequence of the bacteriophage ΦCJ27 is set forth in SEQ ID NO: 1 of Sequence List.

The bacteriophage ΦCJ27 is a novel bacteriophage isolated by the present inventor, and was deposited at the Korean Culture Center of Microorganisms (KCCM) (361-221, Hongje 1-dong, Seodaemun-gu, Seoul, Korea) on Oct. 25, 2013 under accession number KCCM 11465P.

Another embodiment of the present invention provides a composition for preventing or treating infectious diseases caused by enterotoxigenic *Escherichia coli*, including the bacteriophage ΦCJ27 as an active ingredient.

Since the bacteriophage ΦCJ27 exhibits antibacterial activity capable of specifically killing enterotoxigenic *Escherichia coli*, the bacteriophage ΦCJ27 can be utilized in prevention or treatment of diseases caused by infection with enterotoxigenic *Escherichia coli*. Examples of infectious diseases caused by enterotoxigenic *Escherichia coli* to be prevented or treated using the bacteriophage ΦCJ27 include colibacillosis, specifically porcine colibacillosis, without being limited thereto.

Herein, the term "colibacillosis" refers to a disease occurring due to infection with pathogenic *Escherichia coli* in animals, and symptoms thereof include sepsis, diarrhea (infant diarrhea and post weaning diarrhea), toxemia (edema and cerebrospinal angiopathy), and the like. Thereamong, sepsis is an acute systemic infection with high mortality which occurs mainly in infancy within two to three days after birth. Diarrhea is a gastrointestinal infection symptom frequently occurring during suckling within one week old to two weeks old and directly after weaning, which is a cause of mortality or stunted development. Toxemia mainly occurs after weaning in piglets at 8 week old to 12 week old, and can frequently cause sudden death after exhibiting edema and neurological symptoms.

Herein, the term "preventing" or "prevention" refers to all actions to inhibit the diseases or delay occurrence of the diseases by administering the bacteriophage ΦCJ27 and/or the composition including the bacteriophage ΦCJ27 as an active ingredient to an animal.

Herein, the term "treating" or "treatment" refers to all actions to improve or ameliorate symptoms of infectious diseases by administering the bacteriophage ΦCJ27 and/or the composition including the bacteriophage ΦCJ27 as an active ingredient to an animal.

The composition for preventing or treating infectious diseases caused by enterotoxigenic *Escherichia coli* according to this embodiment may include the bacteriophage ΦCJ27 in amounts of $5\times10^2$ pfu/ml to $5\times10^{12}$ pfu/ml, specifically, $1\times10^6$ pfu/ml to $1\times10^{10}$ pfu/ml.

The composition for preventing or treating infectious diseases caused by enterotoxigenic *Escherichia coli* according to this embodiment may further include pharmaceutically acceptable carriers, and may be formulated with the carriers to provide foods, medicines, additives for feeds or additives for drinking water, and the like. Herein, the term “pharmaceutically acceptable carriers” refers to carriers or diluents that do not stimulate an organism and do not inhibit biological activity and properties of administered compounds.

Types of carriers applicable to this embodiment are not particularly limited and any pharmaceutically acceptable carriers commonly used in the art may be utilized. Examples of the carriers may include saline, distilled water, Ringer’s solution, buffered saline, an albumin injection solution, a dextrose solution, a maltodextrin solution, glycerol, and ethanol, without being limited thereto. These may be used alone or in combination thereof.

Furthermore, as needed, other common additives such as antioxidants, buffered solutions and/or cytostatics may be added to the composition according to the present invention, and diluents, dispersants, surfactants, binders and/or lubricants may be further added to the composition according to the present invention to formulate injectable formulations such as aqueous solutions, suspensions and emulsions, pills, capsules, granules, and tablets.

Methods for administering the composition for preventing or treating infectious diseases caused by enterotoxigenic *Escherichia coli* according to this embodiment are not particularly limited, and any methods commonly used in the related art may be used. One example of the administration method may include oral administration or parenteral administration.

Examples of dosage forms for oral administration may include troches, lozenges, tablets, water soluble suspensions, oil-based suspensions, formulated powder, granules, emulsions, hard capsules, soft capsules, syrups, and elixirs.

In order to formulate the composition according to this embodiment into dosage forms such as tablets or capsules, binders such as lactose, saccharose, sorbitol, mannitol, starches, amylopectin, cellulose and gelatin; excipients such as dicalcium phosphate; disintegrators such as corn starch and sweet potato starch; lubricants such as magnesium stearate, calcium stearate, sodium stearyl fumarate and polyethylene glycol wax may be further included, and for capsule formulation, liquid carriers such as fatty oils may be further included in addition to the aforementioned substances.

Methods for parenterally administering the composition of this embodiment may include, for example, intravenous injection, intraperitoneal administration, intramuscular administration, subcutaneous administration, and topical administration, and a method of applying or spraying the composition according to the present invention to an affected region, without being limited thereto.

In order to formulate parenteral dosage forms, for example, the composition of this embodiment may be formulated into dosage forms for injection such as subcutaneous injection, intravenous injection and intramuscular injection; suppositories; or dosage forms for spraying such as aerosols so as to permit inhalation through inhalers, without being limited thereto. In order to formulate dosage forms for injection, the composition of this embodiment may be mixed with stabilizers or buffering agents in water to prepare solutions or suspensions, which are formulated into dosage forms for unit administration such as ampoules or vials. When the composition is formulated into dosage forms for spraying such as aerosols, the composition may be formulated with propellants and the like together with additives such that a concentrate dispersed in water or wetted powder is dispersed therein.

Suitable amounts of applying, spraying or administering the composition for preventing or treating infectious diseases caused by enterotoxigenic *Escherichia coli* according to this embodiment may differ according to factors such as age, body weight and sex of animals, degree of disease symptoms, ingested foods, rate of excretion, and the like in addition to a method for formulating the composition, an administration method, administration time and/or routes for administration, and a generally skilled veterinarian can easily determine and prescribe dose amounts effective for intended treatment.

A further embodiment of the present invention provides antibiotics including the bacteriophage ΦCJ27 as an active ingredient.

Herein, the term “antibiotics” refers to a preparation that is administered to animals including humans in medicine form and exhibits efficacy of sterilizing bacteria, and is used as a general term for antiseptics, germicides and antibacterial agents.

Antibiotics of this embodiment including the bacteriophage ΦCJ27 as an active ingredient have effects in that the antibiotics have specificity for enterotoxigenic *Escherichia coli* as compared to typical antibiotics and thus kill specific pathogenic bacteria, but not beneficial bacteria; and in that the antibiotics do not induce antibiotic resistance, causing extension of lifetime of products as compared to typical antibiotics.

Yet another embodiment of the present invention provides an additive for feeds or an additive drinking water, which includes the bacteriophage ΦCJ27 as an active ingredient.

The additives for feeds or the additives for drinking water may be used by separately preparing additives for feeds or additives for drinking water using the bacteriophage CJ27 or the composition including the same and mixing feeds or drinking water with the additives, or directly adding the bacteriophage ΦCJ27 or the composition including the same in a process of preparing feeds or drinking water.

The bacteriophage ΦCJ27 or the composition including the bacteriophage ΦCJ27 as an active ingredient used in the form of additives for feeds or additives for drinking water according to this embodiment may be a liquid form or a dried form, for example, a dried powder form.

For example, the bacteriophage ΦCJ27 according to the present invention is mixed in powder form in amounts of 0.05% by weight (wt %) to 10 wt %, specifically 0.1 wt % to 2 wt %, based on the weight of additives for feeds.

Methods for drying the additives for feeds or additives for drinking water according to this embodiment to yield dried powder are not particularly limited, and any methods commonly used in the related art may be utilized. Examples of the drying method may include air drying, natural drying, spray drying, and lyophilization, without being limited thereto. These methods may be used alone or in combination thereof.

The additives for feeds or additives for drinking water according to this embodiment may further include other non-pathogenic microorganisms. Non-restrictive examples of the microorganisms may be selected from the group consisting of *Bacillus* sp. such as *Bacillus subtilis* capable of producing proteases, lipases and/or glycosyltransferases; lactic acid bacteria such as *Lactobacillus* sp. having physiological activity and organic material decomposing capability under anaerobic conditions like the stomach of cattle; filamentous bacteria such as *Aspergillus oryzae* having effects of weight gain in animals, increase in milk production, and increase of digestion-absorption rate of feed; and yeasts such as *Saccharomyces cerevisiae*, and the like. These microorganisms may be used alone or in combination thereof.

The additives for feeds or additives for drinking water according to this embodiment including the bacteriophage ΦCJ27 as an active ingredient may further include other additives as needed. Examples of usable additives may include binders, emulsifiers, and preservatives added for prevention of quality deterioration of feeds or drinking water; amino acid, vitamin, enzyme, probiotics, flavoring agents, non-protein nitrogen compounds, silicate, buffering agents, coloring agents, extracting agents or oligosaccharides that are added in order to increase utility of feeds or drinking water; and other supplements to feeds, and the like. These additives may be used alone or in combination thereof.

The additives for feeds according to the present invention may be present in amounts of 0.05 parts by weight to 10 parts by weight, specifically 0.1 parts by weight to 2 parts by weight, based on 100 parts by weight of feed. The additives for drinking water according to the present invention may be present in amounts of 0.0001 parts by weight to 0.01 parts by weight, specifically 0.001 parts by weight to 0.005 parts by weight, based on 100 parts by weight of drinking water. Within these ranges, the additives allow activity of the bacteriophage ΦCJ27 against enterotoxigenic *Escherichia coli* to be sufficiently displayed.

Yet another embodiment of the present invention provides feeds or drinking water prepared by adding the additives for feeds or the additives for drinking water including the bacteriophage ΦCJ27 as an active ingredient to feeds or drinking water, or directly adding the bacteriophage ΦCJ27 thereto.

Feeds used in this embodiment are not particularly limited, and any feeds commonly used in the related art may be used. Examples of the feeds may include vegetable feeds such as grains, root vegetables, food processing byproducts, algae, fibers, pharmaceutical byproducts, oils and fats, starches, residues or byproducts of grains and the like; and animal feeds such as proteins, inorganic substances, oils and fats, minerals, single cell proteins, and animal planktons or foods. These feeds are used alone or in combination thereof.

Drinking water used in this embodiment is not particularly limited, and any drinking water commonly used in the related art may be used.

Yet another embodiment of the present invention provides disinfectants or detergents including the bacteriophage ΦCJ27 as an active ingredient. Dosage forms of the disinfectants or detergents are not particularly limited, and any dosage forms commonly used in the related art may be used.

In order to remove enterotoxigenic *Escherichia coli*, the disinfectants may be sprayed to habitats of animals, slaughterhouses, dead regions, kitchens, and cooking equipment, without being limited thereto.

The detergents may be used to wash a surface of the dermis or body parts of animals that are exposed to or can be exposed to enterotoxigenic *Escherichia coli*, without being limited thereto.

Yet another embodiment of the present invention provides a method for preventing or treating infectious diseases caused by enterotoxigenic *Escherichia coli* using the bacteriophage ΦCJ27 or the composition including the bacteriophage ΦCJ27 as an active ingredient.

Specifically, the prevention method or treatment method of this embodiment includes administering a pharmaceutically effective amount of the bacteriophage ΦCJ27 or the composition including the bacteriophage ΦCJ27 as an active ingredient to a non-human animal that is exposed to or can be exposed to enterotoxigenic *Escherichia coli*. Suitable total amounts of the bacteriophage ΦCJ27 or the composition including the same per day may be determined by a veterinarian within proper medicinal judgment, as apparent to those skilled in the art.

A concrete pharmaceutically effective amount of the bacteriophage ΦCJ27 or the composition including the bacteriophage ΦCJ27 as an active ingredient may be determined by taking into account the sorts and degree of reaction to achieve, age, body weight, general health condition, sex or diet of corresponding individuals, administration time and administration routes of bacteriophage ΦCJ27 or a composition including the same, and secretion rate of the composition, treatment period, and the like, and may differ depending upon various factors and similar factors well known in the field of medicine including components of medicines that are used simultaneously or at different times.

The bacteriophage ΦCJ27 or the composition including the bacteriophage ΦCJ27 as an active ingredient may be administered in the form of a pharmaceutical preparation to an animal by intranasal spraying, or directly added to feeds or drinking water for animals so as to be digested, and may be mixed in the form of additives for feeds or additives for drinking water with feeds or drinking water and then administered to an animal.

Routes and methods for administration of the bacteriophage ΦCJ27 or the composition including the bacteriophage ΦCJ27 as an active ingredient are not particularly limited, and the administration route may be realized by any routes and methods so long as the administration allows the bacteriophage ΦCJ27 or the composition including the same to reach desired tissues. Namely, the bacteriophage ΦCJ27 or the composition including the bacteriophage ΦCJ27 as an active ingredient may be administered by various oral or parenteral routes, and examples of administration may include oral, rectal, topical, intravenous, intraperitoneal, intramuscular, intra-arterial, trans-dermal, intranasal, and inhalation, without being limited thereto.

Hereinafter, the present invention will be described in more detail with reference to a preferred example. It should be understood that these examples are not to be construed in any way as limiting the present invention.

Example 1—Isolation of Bacteriophage that Infects Enterotoxigenic *Escherichiac coli*

Example 1-1

Bacteriophage Screening and Single Bacteriophage Isolation 50 ml of a specimen obtained from pig feces collected around Samwhawonjong farm in Gwangcheon, Hongsung-gun, Chungcheong Province and environmental samples were centrifuged at 4,000 rpm for 10 minutes, and the resulting supernatant was filtered through a 0.45 μm filter to prepare a specimen liquid, which in turn was used to perform a soft agar overlay method. The soft agar overlay method refers to a method of observing bacteriophage lysis using a host cell growing on top-agar (attached to a solid medium using 0.7% agar).

Specifically, 150 μl of a shaking culture solution ($OD_{600}$=2) of enterotoxigenic *Escherichia coli* (UK27) separated by the Department of Veterinary Medicine, Konkuk University and 2 ml of 10×LB medium (10 g/l of tryptophan; 5 g/l of yeast extract; 10 g/l of NaCl) were mixed with 18 ml of the filtered specimen liquid, followed by culturing at 30° C. for 18 hours, and the resulting cultured solution was centrifuged at 4,000 rpm for 10 minutes, and the resulting supernatant was filtered through a 0.45 μm filter. Subsequently, a mixed solution consisting of 5 ml of 0.7% (w/v) agar and 150 μl of a shaking culture solution ($OD_{600}$=2) of enterotoxigenic *Escherichia coli* (UK27) was poured and solidified on an LB medium plate, to which 10 μl of the specimen liquid was added dropwise, followed by culturing at 30° C. for 18 hours, thereby identifying formation of plaques.

Since it is known that one sort of bacteriophage is present per plaque, the inventors tried to isolate single bacteriophages from the formed plaques. Specifically, 400 μl of SM solution (5.8 g/l of NaCl; 2 g/l of $MgSO_4 7H_2O$; 50 ml of 1M Tris-HCl (pH 7.5)) was added to the plaques and left at room temperature for 4 hours, thereby obtaining a bacteriophage solution. Subsequently, 100 μl of the bacteriophage solution was mixed with 5 ml of 0.7% (w/v) agar and 150 μl of a shaking culture solution ($OD_{600}$=2) of enterotoxigenic *Escherichia coli* (UK27), which was used to perform a soft agar overlay method using an LB medium plate having a diameter of 150 mm wherein cultivation was performed until the bacteriophage was completely lysed. After completion of cultivation, 5 ml of SM solution was added to the LB medium plate and left at room temperature for 4 hours, thereby obtaining a bacteriophage solution.

To the obtained solution, 1% (v/v) chloroform was added and mixed for 10 minutes, followed by centrifugation at 4,000 rpm for 10 minutes, thereby obtaining a supernatant, which in turn was filtered through a 0.45 μm filter, thereby obtaining a final specimen.

Example 1-2

Large Scale Culture and Purification of Bacteriophage

Bacteriophage obtained in Example 1-1 was cultured at large scale using enterotoxigenic *Escherichia coli* (UK27), and then the bacteriophage was purified therefrom.

Specifically, enterotoxigenic *Escherichia coli* (UK27) was shaking cultured, and inoculated at $1.5\times10^{10}$ cfu, followed by centrifuging at 4,000 rpm for 10 minutes, and resuspending in 4 ml of SM solution. To this solution, the bacteriophage was added at $1.5\times10^{7}$ pfu with multiplicity of infection (MOI) of 0.001, and then left at room temperature for 20 minutes. 150 ml of LB medium was inoculated therewith, and cultured at 30° C. for 5 hours.

After completion of cultivation, chloroform was added to a volume of 1% (v/v) of the final volume, followed by stirring for 20 minutes, to which DNase I and RNase A as restriction enzymes were added in a final concentration of 1 μg/ml, respectively, and left at 30° C. for 30 minutes. Subsequently, sodium chloride and polyethylene glycol were added to a final concentration of 1M and 10% (w/v), respectively, and left at 4° C. for 3 hours, followed by centrifuging at 4° C. and 12,000 rpm for 20 minutes, thereby obtaining a precipitate.

The obtained precipitate was suspended in 5 ml of SM solution and then left at room temperature for 20 minutes, 1 ml of chloroform was added thereto with stirring, followed by centrifugation at 4° C. with 4,000 rpm for 20 minutes, thereby obtaining a supernatant. The supernatant was filtered through a 0.45 μm filter, followed by ultracentrifugation (35,000 rpm, 1 hour, 4° C.) using a glycerol density gradient method (density: 40%, 5% glycerol), thereby purifying a bacteriophage.

The present inventors isolated a bacteriophage having a specific ability to kill enterotoxigenic *Escherichia coli* from samples collected from pig feces, which was designated as "Bacteriophage ΦCJ27" and deposited at the Korean Culture Center of Microorganisms (KCCM) (361-221 Hongje 1-dong, Seodaemun-gu, Seoul, Korea) on Oct. 25, 2013 under accession number KCCM 11465P.

Example 2

Morphology Observation of ΦCJ27

The bacteriophage ΦCJ27 purified in Example 1 was diluted in 0.01% gelatin solution, and then fixed with a 2.5% glutaraldehyde solution. The resulting bacteriophage was added dropwise to a carbon-coated mica plate (ca. 2.5 mm×2.5 mm), acclimated for 10 minutes, and then washed with distilled water. The carbon film was mounted on a copper grid, and stained with 2% uranyl acetate for 60 seconds, dried, and examined under a transmission electron microscope (JEM-1011, 120 kV, magnification of ×200,000) (FIG. 1).

FIG. 1 is a transmission electron microscope image of bacteriophage ΦCJ27, in which the bacteriophage ΦCJ27 had morphological characteristics of an elongated head and a contractile tail, indicating that the bacteriophage belongs to family Myoviridae.

Example 3

Total Genomic DNA Size Analysis of ΦCJ27

Genomic DNA was extracted from the bacteriophage ΦCJ27 purified in Example 1.

Specifically, to a cultured solution of the purified bacteriophage ΦCJ27, 20 mM ethylenediaminetetraacetic acid (EDTA), 50 μg/ml protease K and 0.5% (w/v) sodium dodecyl sulfate (SDS) were added and left at 50° C. for one hour, to which an equal amount of phenol (pH 8.0) was added with stirring, followed by centrifugation at room temperature and 12,000 rpm for 10 minutes, thereby obtaining a supernatant.

The supernatant was mixed with an equal volume of PC (phenol:chloroform=1:1), followed by centrifugation at room temperature and 12,000 rpm for 10 minutes, thereby obtaining a supernatant. The supernatant was mixed with an equal volume of chloroform, followed by centrifugation at room temperature and 12,000 rpm for 10 minutes, thereby obtaining a supernatant. The supernatant was mixed with 3M sodium acetate in an amount of 10% (v/v) based on the total volume, followed by the addition of 2-fold volumes of cold 95% ethanol, mixing, and standing at −20° C. for 1 hour. The resulting substance was centrifuged at 0° C. and 12,000 rpm for 10 minutes, from which a supernatant was removed to obtain a precipitate, which was dissolved in 50 μl of TE buffered solution (Tris-EDTA, pH 8.0). The extracted DNA was diluted 10 fold, and then concentration of DNA was determined by measuring absorbance at $OD_{260}$.

Next, 1 μg of DNA was loaded on a 1% PFGE (pulsed field gel electrophoresis) agarose gel, and developed using BIORAD PFGE SYSTEM NO. 7 PROGRAM (size ranging from 25 kb to 100 kb; switch time ramp 0.4 seconds to 2.0 seconds, linear shape; forward voltage, 180 V; reverse voltage, 120 V) at room temperature for 20 hours (FIG. 2).

FIG. 2 is an electrophoresis gel photograph of genomic DNA of the bacteriophage ΦCJ27, and it could be seen that the genomic DNA size of the bacteriophage ΦCJ27 was 98 kb or more. In FIG. 2, M corresponds to DNA ladder as a standard for size measurement.

Example 4

Protein Pattern Analysis of ΦCJ27

15 μl of purified bacteriophage ΦCJ27 solution ($10^{11}$ pfu/ml titer) was mixed with 3 μl of 5×SDS sample solution, and then boiled for 5 minutes to perform 12% SDS-PAGE (FIG. 3).

FIG. 3 is an electrophoresis photograph of SDS-PAGE results performed on the bacteriophage ΦCJ27, and it could be seen that main proteins had a size of about 27.9 kDa, about 51.8 kDa and about 74.5 kDa.

Example 5

Analysis of Genetic Properties of ΦCJ27

In order to determine genetic properties of the bacteriophage ΦCJ27 purified in Example 1, DNA of the bacteriophage ΦCJ27 was analyzed using an FLX Titanium Sequencer (Roche) as a gene analyzer. Genes were recombined using GS and de novo assembler software (Roche) by Macrogen Inc. Open reading frame was identified using GeneMark.hmm, Glimmer v3.02 and FGENESB software. Open reading frame was annotated using BLASTP and InterProScan program.

Nucleotide sequence of the bacteriophage ΦCJ27 showed similarity to nucleotide sequence of previously reported bacteriophage (Enterobacteria phage HX01, complete genome), but it could be seen that there were no bacteriophages in which all fragments 100% coincide. Accordingly, it could be seen that the bacteriophage was a novel isolated bacteriophage.

The following Table 1 shows comparison results between nucleotide sequence of the bacteriophage ΦCJ27 and decoded nucleotide sequence of the prior reported bacteriophage in the art.

TABLE 1

| Query | | | | Subject Description | E-Value | Identities | |
|---|---|---|---|---|---|---|---|
| Name | Length | Start | End | | | Match/Total | Pct. (%) |
| SEQ ID NO: 1 | 171637 | 144696 | 167103 | Enterobacteria phage HX01, complete genome | 0 | 21905/22425 | 97 |

DNA of the prepared bacteriophage ΦCJ27 was analyzed using a DNA sequencer and total nucleotide sequence is set forth in SEQ ID NO: 1.

Example 6 pH Stability of ΦCJ27

In order to identify whether the bacteriophage ΦCJ27 can maintain stability at low pH like stomach conditions, stability of the bacteriophage ΦCJ27 was examined at various pH (pH 2.0, 3.0, 4.0, 5.0).

For the experiment, various pH solutions (sodium acetate buffer solutions (pH 4.0 and pH 5.0) and sodium citrate buffer solutions (pH 2.0 and pH 3.0)) were prepared at a concentration of 0.2M.

180 μl of each pH solution was mixed with 20 μl of a bacteriophage solution with $3.8\times10^9$ PFU/ml titer to allow each pH solution to have a concentration of 1M, and then the resulting solution was left at room temperature for 2 hours. For a control group, 20 μl of a bacteriophage solution with $3.8\times10^9$ PFU/ml titer was mixed with 180 μl of SM solution by the same method, and the resulting solution was left at room temperature for 2 hours. Thereafter, the solutions were serially diluted, and 10 μl of each of solutions in each dilution step was cultured by the soft agar overlay method at 30° C. for 18 hours to determine bacteriophage titer based on whether the bacteriophage was lysed (FIG. 4).

FIG. 4 shows experimental results of acid resistance of the bacteriophage ΦCJ27. In FIG. 4, it could be seen that the bacteriophage ΦCJ27 did not lose its activity and maintained stability from pH 2.0 to pH 5.0, as compared with the control group.

Example 7

Heat Stability of Bacteriophage ΦCJ27

If bacteriophages are formulated into additives for feeds among dosage forms of bacteriophages, heat can be generated during formulation procedures, and thus, the following experiment was performed in order to determine heat stability of bacteriophages.

Specifically, 200 μl of bacteriophage ΦCJ27 solution with $3.8\times10^8$ PFU/ml was left at 60° C. for 0 minute, 30 minutes, 60 minutes and 120 minutes, respectively. Thereafter, the resulting experimental culture solution was serially diluted, and 10 μl of each of solutions in each dilution step was cultured by the soft agar overlay method at 30° C. for 18 hours to determine bacteriophage titer based on whether the bacteriophage was lysed (FIG. 5).

FIG. 5 shows experimental results of heat resistance of bacteriophage ΦCJ27. As shown in FIG. 5, it could be seen that bacteriophage ΦCJ27 exhibited activity decline of about 1 log or less until bacteriophage ΦCJ27 was exposed to 60° C. for one hour and activity decline of 1 log or more when bacteriophage ΦCJ27 was exposed for more than 120 minutes.

Example 8

Examination of Infection Range of Bacteriophage ΦCJ27 on a Wild-Type Isolated Strain, Enterotoxigenic *Escherichia coli*

Lytic activity of bacteriophage ΦCJ27 was tested for 99 strains of the wild-type enterotoxigenic *Escherichia coli* isolated by College of Veterinary Medicine, Seoul National University (SNU), College of Veterinary Medicine, Konkuk University and Korea Animal and Plant Quarantine Agency (KAPQA), in addition to enterotoxigenic *Escherichia coli* (UK27) used in the present experiment. The isolated strains consist of 37 strains of F-serotype F4 type, 31 strains of F5 type, 7 strains of F6 type, 19 strains of F18 type and 5 strains of other type.

Specifically, 150 μl of a shaking culture solution of each strain ($OD_{600}$=2) was mixed, and 10 μl of bacteriophage ΦCJ27 solution with $10^9$ pfu/ml titer was cultured by the soft agar overlay method at 30° C. for 18 hours, and then plaque formation was examined.

The results are shown in Table 2.

TABLE 2

| no. | Type | strains | ØCJ27 | no. | Type | Host cell | ØCJ27 |
|---|---|---|---|---|---|---|---|
| 1 | F4 | 345 | | 51 | F5 | UK21 | 0 |
| 2 | | 105 | 0 | 52 | | UK23 | 0 |
| 3 | | 122 | | 53 | | UK24 | 0 |
| 4 | | 0149 | | 54 | | UK25 | 0 |
| 5 | | JG280 | 0 | 55 | | UK26 | 0 |
| 6 | | F4 | 0 | 56 | | 1-1 | 0 |
| 7 | | 162 | 0 | 57 | | 6-1 | 0 |
| 8 | | 160 | 0 | 58 | | 9 | |
| 9 | | 107 | 0 | 59 | | 10 | 0 |
| 10 | | R08 | 0 | 60 | | 14 | |
| 11 | | 193 | | 61 | | 16 | 0 |
| 12 | | 274 | 0 | 62 | | 17 | |
| 13 | | 3220 | 0 | 63 | | 30 | 0 |
| 14 | | UK1 | 0 | 64 | | 31 | |
| 15 | | UK3 | | 65 | | 34 | |
| 16 | | UK4 | | 68 | | 35 | |
| 17 | | UK7 | 0 | 67 | | 21 | 0 |
| 18 | | UK8 | 0 | 68 | | 23 | 0 |
| 19 | | UK9 | 0 | 69 | F6 | F6 | |
| 20 | | UK11 | | 70 | | 626 | 0 |
| 21 | | UK14 | 0 | 71 | | p87 | 0 |
| 22 | | UK15 | 0 | 72 | | S127 | 0 |
| 23 | | UK16 | 0 | 73 | | 132 | |
| 24 | | UK17 | 0 | 74 | | 133 | |
| 25 | | UK18 | 0 | 75 | | 135 | |
| 26 | | UK19 | 0 | 76 | F18 | UK5 | |
| 27 | | UK20 | 0 | 77 | | UK6 | 0 |

TABLE 2-continued

| no. | Type | strains | ØCJ27 | no. | Type | Host cell | ØCJ27 |
|---|---|---|---|---|---|---|---|
| 28 | | 0105 | 0 | 78 | | UK10 | 0 |
| 29 | | UK24 | 0 | 79 | | UK12 | 0 |
| 30 | | UK25 | 0 | 80 | | UK13 | 0 |
| 31 | | UK26 | 0 | 81 | | UK22 | |
| 32 | | UK29 | | 82 | | UK27 | 0 |
| 33 | | UK30 | 0 | 83 | | E2-4 | 0 |
| 34 | | UK31 | 0 | 84 | | 5 | 0 |
| 35 | | 66-1 | 0 | 85 | | 8 | |
| 36 | | KAPQA 43 | 0 | 86 | | 11 | |
| 37 | | KAPQA 45 | | 87 | | 12 | |
| 38 | F5 | 2618 | 0 | 88 | | 23 | |
| 39 | | 2617 | | 89 | | 24 | |
| 40 | | 1 | | 90 | | 25 | |
| 41 | | 2 | | 91 | | 28 | 0 |
| 42 | | 3 | 0 | 92 | | 31 | |
| 43 | | 4 | 0 | 93 | | 35 | |
| 44 | | 5 | 0 | 94 | | 42 | |
| 45 | | 6 | 0 | 95 | | 49 | |
| 46 | | F5041 | 0 | 96 | Other | UK32 | |
| 47 | | 645 | | 97 | | UK33 | |
| 48 | | k99 | | 98 | | UK34 | 0 |
| 49 | | 5192 | | 99 | | UK35 | 0 |
| 50 | | UK2 | | 100 | | UK36 | 0 |

As shown in table 2, the bacteriophage ΦCJ27 exhibits infection ability to F-serotype F4, F5, F6, F18 types, which are major causative bacteria of pig diarrhea in general pig farms, and thus is anticipated to exhibit excellent efficacy.

The invention claimed is:

1. A feed composition comprising a feed and an additive comprising bacteriophage ΦCJ27 deposited as accession number KCCM11465P.

2. A drinking water composition comprising drinking water and an additive comprising bacteriophage ΦCJ27 deposited as accession number KCCM11465P.

3. A method for preventing or treating infectious diseases caused by *Salmonella*, comprising:

administering bacteriophage ΦCJ27 deposited as accession number KCCM11465P to a non-human animal.

4. The method for preventing or treating infectious diseases caused by *Salmonella* according to claim 3, wherein the animal is poultry.

5. A method for preventing or treating infectious diseases caused by *Salmonella*, comprising:

administering a composition comprising bacteriophage ΦCJ27 deposited as accession number KCCM11465P to a non-human animal.

6. A method of preparing an additive composition, the method comprising:

providing bacteriophage ΦCJ27 deposited as accession number KCCM11465P; and mixing the bacteriophage with at least one additional material to provide the additive composition.

7. The method of claim 6, wherein the bacteriophage is in an amount of 0.05 wt % to 10 wt % based on the weight of the additive composition.

8. A method of preparing a feed composition, the method comprising:

preparing an additive composition according to the method of claim 6; and mixing the additive composition with an animal feed to provide the feed composition.

9. A method of feeding, the method comprising:

preparing the feed composition according to the method of claim 8; and providing the feed composition to an animal.

10. A method of preparing a drinking water composition, the method comprising:

preparing an additive composition according to the method of claim 6; and mixing the additive composition with drinking water to provide the drinking water composition.

11. A method of providing drinking water to an animal, the method comprising:

preparing the drinking water composition according to the method of claim 10; and providing the drinking water composition to an animal.

* * * * *

UNITED STATES PATENT AND TRADEMARK OFFICE

CERTIFICATE OF CORRECTION

PATENT NO. : 9,950,018 B2
APPLICATION NO. : 15/304489
DATED : April 24, 2018
INVENTOR(S) : Eun Mi Shin, Gi Duk Bae and Jae Won Kim It is certified that error appears in the above-identified patent and that said Letters Patent is hereby corrected as shown below:

In the Specification

In Column 1 at Line 18, change ""E. coli" to --Escherichia coli--.

In Column 3 at Line 29, change "CJ27." to --ΦCJ27.--.

In Column 8 at Line 55, change "Escherichiac" to --Escherichia--.

In the Claims

In Column 159 at Line 16, in Claim 3, delete "Salmonella," and add --enterotoxigenic Escherichia coli,--.

In Column 159 at Line 20, in Claim 4, delete "Salmonella," and add --enterotoxigenic Escherichia coli,--.

In Column 159 at Line 21, in Claim 4, delete "poultry" and add --porcine--.

In Column 159 at Line 23, in Claim 5, delete "Salmonella," and add --enterotoxigenic *Escherichia coli*,--.

Signed and Sealed this
Fourteenth Day of August, 2018

Andrei Iancu
*Director of the United States Patent and Trademark Office*

SEQUENCE LISTING

<160> NUMBER OF SEQ ID NOS: 1

<210> SEQ ID NO 1
<211> LENGTH: 171637
<212> TYPE: DNA
<213> ORGANISM: Artificial Sequence
<220> FEATURE:
<223> OTHER INFORMATION: Novel Bacteriophage CJ27

<400> SEQUENCE: 1
aacgataatt gcatattggt catcagtttg cgggccatat ccaaacactg ctttagcagt 60
agatgcacga gtaccaccat caggataaat ttttaactgg gctgaagcac ctttgtcata 120
gtctgcttta gatacgattt caatttcgag ctggtcacca agttcaccag gataaagagc 180
aactacgcct ggaacgccat attttttaat agattcttgg aaagttagag aagtaatagc 240
ttcttcagaa gtttcaactt cagttaacag aatacccgaa tcggttacga tagaaccaat 300
tgtaataacg ccagaaagtc cagaagaaga actggcaact tcggcggtcc aattagaacc 360
caatgccgga tattcattaa tttcttttgc acgagcaata attttaccgg ttgggatata 420
aatgttaaga attttaccat cgacatcaac tgaagtgaca taaccatctg cttcaacagt 480
ttcggtcaaa tacttaacga taattttatc accaactgca tagttactac cagcagcaga 540
gattgtgaat tcaatattgc ctgctacagg agatgagttc ttagcagtat cacgatcaac 600
tgcgcgtaca acacgaaggt cattaccata ttgaaggaag ttcatagcag acatgaaata 660
atctgctgta tccgtattag gagtaccaaa catatcaact aatgcaactt catcagtgat 720
ttgtttaatc tggaatgcag gtccccattg gaattttcca gccagggcag cagtaccagt 780
ggagttatta actacagtac tctgtacggt agtttctttg agctcaacgc ccggagagag 840
aagtgacatt ttaattcctc ttaatttgct ttattttatt tataccattg acaggccatg 900

-continued

```
tgctgatgga ttatattcgg ctgaattact tgcgcagtca acaaatataa ccggggcgta    960
gtcgtcattc atatcctgta attctcttga gaatacttct gatgcaagac gcatatcatc   1020
tttatccgca tagtctgcaa atttctgttg cgttgtcaac catccgaaaa taacaaggcc   1080
catcactaag tcgtcatggt aaccttcttc agctgcccaa gatacaccct tttcactaaa   1140
cgttctgaat tcttgaatag tagccctatg gtttattttg agcttgtctt tttcaataag   1200
gtcctttaat gtagagcaac ctacaggctt agttctacgg ctttgcttca tgcctaaatc   1260
attcattgaa tcacaaataa cgttttcata ttcaaggtcc atataaagtg atttagcgac   1320
agaaacacct gttgagttca attcaatata aattggacat tcgttatatt ccattagata   1380
tttaaacaca atatcaggga gtataaggtg tgaaatagta ttagagtgta gaacaccaac   1440
ttgttcccat ttatctgtcg taacatcaat aatatgcatt gcgtgatagt cctgcccacg   1500
accttcagaa cagtctaacg tcgcaatata tttatgtcct tcctcaggct ttttgaaccg   1560
gtgaaatcca tgactatcgg gtgtaacttc aatgtaatcc aatatagcca atttcatacc   1620
tgaaataagt gtgcctgacg tcccctcgaa agctgcagta tgttcttgac gaaactgtga   1680
taatgaagag gctgaaatag tctgtttaga ccactgccat ccatcatcaa aaatatcttc   1740
atcgttgtat agtcgttctt taactgagtt ccaaattgca gtataaggtt caaatcctga   1800
tttaccttca acagctgcag tccaaatatc ataaaagtga tttaatccat ttggtgtggt   1860
tgtaataata atttttgaac gacgacctga agaaataaca ggttgaatag caagccatga   1920
atcaatgaag tttgggataa acgcgcactc atcaatataa atcatagcga acgagttacc   1980
acgaaccgca tccggtgatg aagcgtaagc accgattgag gaaccgttgt ctaactgaat   2040
agaccctttg ttccattcaa caatacctgg ttgtaaaaaa tcagggagta attcaattgc   2100
ttgttttgta cggtctaata cttccgccga cattgagcct ttatgtgcaa gaatacctac   2160
tgctttatct ttgttaaagc aaacaaaatg agcaagaaaa atagctacta cagtcgtttt   2220
gcctagctgg cgtgacaagt tacaaacagt catacgctta gaagacatta ttttaagcat   2280
atcacgttga tagtcacgaa gttgtacttt aattgtaccg tagtcgatat gggtaatagc   2340
acaatatgtc tcagcaaaat atacaatgtc atcacggcat tttttccact cggcgaccat   2400
ttcataggtc cattgagttt ttatatttgc tcttttaagg tttggtaaac ccatataccg   2460
tgtacgctta ttattcttat ctttgtatgt ttgaaataat tcaggcttat ctgagttatt   2520
aggaatttta actattttgt ttatacgtag ataatcacta aatttttccg ggtaccattt   2580
accgtcccat tgggatttaa tccaatggat accatcttct tctttacgtt cagctaaatg   2640
aggtggtaga ataacaactt tgtcaccttc attcaatggg tgattatcat tcaatgcgtt   2700
aactggctgt tccattaatc accttctcac gagcttcttg agcctcgtaa gcatctccta   2760
cttcttccat taattctgtt ggagagccca tgaacactgt agcattttgg atattcatct   2820
gactagatgg agcagcattt ttagtgccaa cctgttcaga tgtgatttct ttcatatctt   2880
tatgaagctt cagtatttct ttgttcgtcg tagtcatttg ccccataaga gttgcaaata   2940
cttccatgtg acgaggagaa tcggcatttt tagccgtctc aagaaaaatc ttggcagcgt   3000
ccattaacat ttgttgttgg aagtgcatat tcttacgaac aacgctatag tcatcttcca   3060
aatccggggt gcggttttga ggattactct gaacttccac caattgtaaa ggagcatata   3120
cctctacttc ctccccagat attccaggga ggtcagagat atctaaaagc ttattaatat   3180
ctagaccttc catatttacc tcttattgtt ttctaggacc aggaggggtt ggtggagtcg   3240
ggattggaat atcatgagta taagtttgtt caacttcacc attccaatct tgggcttcaa   3300
```

-continued

```
cgtctctcgg tttaatttct gtatcaactg attcaaaaac gctggcggct gtttgaaggt   3360
ctcgttcatt agcatgaaaa tcaagataag tcgttttaat aaggccttca gctgcgccta   3420
ccggaggata catccatcca tttacttcaa atgttaatga ccactctaaa cgtcgacggg   3480
ataaattatc accgtctatt tgttcatcca ttgctgctgc catccatacg actttaatat   3540
ccctttcaaa tggaatatcc tgcccatatt gctcaatcat agtcgtatta aaatgcggct   3600
gaaaatatgg aataatttgc tcaacgattt ggaacatatc atcttcataa cgagtaaaga   3660
tgctcagttc aaaaatcatt ttaattggtg atgggttgta ttggtctaca atatccttag   3720
tcgatttact caaaagagag ttattcaata tattcgtttt aaacgtcggg ttataaacga   3780
aatctaccat ttggagattt atacgtggta gaatagtttc gactttagcc acatcttctt   3840
gtgagtttat agaggtccat ttattaagtt tcatcataaa gtgctcttta gatgcatacg   3900
taataggaac tctaattaat ttattgcctg tagacaattg acggttaact tggatatttg   3960
aaaacaaatc gcccatcatt gtgatatatc gcctgaacga cgagttgtaa aaatagccaa   4020
acatcatttc tcctaaccgg cctttcgacc ggtgtttgct ttatcttatc tatttattaa   4080
ttcataaacc catcgtcaaa cggtgaattt tgtctaccac ggttgttaac tactacgtat   4140
ggttcaacgt attcacttgc ctctgaattg atttgctcaa cttcagaata ttcatcgata   4200
ttaatgtcat ggataccgtc aagatttcta acagggttaa gttccaagtc actaaattca   4260
ggtatattga taccttcatt tttctgaagc accggattga tttcttcacc agagtaaata   4320
aacttgcctg cagtaatttt acgaattgca tttttaccta cttgatagaa tgggtcatat   4380
ggttcaaccc agttaatctc aaacaaactg ttgtccattg ggaagtatat taaatcacct   4440
tccttaggct cctgattgtt gacctggtgt ttgaaaagac ctgggttaat agataatgta   4500
acttcgtctt gaacttgcat tccgaagttg ctgaagaacg atttcgctcc ttcataacct   4560
tcaaatgagt tcagatatgc tgcaaatttc catgctttag taaatttatt tttaaggtcc   4620
tcgccaaaga taaggtccac agcaacatat tcacgtggaa cataaaaaca ttcaatacca   4680
cgcatctgta tgctttctgc cactagaaca tcggctaatg tctgactatt ctcatagtta   4740
ttaaaattga caaatggatt gaggatttca gtctcatttg tctgagaata cccaccacga   4800
ttttccagct tggcgaaaag atttttatca taagtagcca tattaaccta ccaaaatacc   4860
tgcaggaggg tccagtaaat ataactcttc tcgtaaagct tctttctcta aacgagcttc   4920
ttcaattaat cgaacaccat caacagtgac gccacccggt aacatcatac cttgatgttt   4980
agcaagaatt tgtccattaa gctctttagc taatgcagtt gcataatctt taacccagcg   5040
gttgttatat gcaccttgtt tagttgcagg atcttcacca actcgacgtc cgaccaaatt   5100
atggtctgga ttatcataac gttcagaaat agaccatgaa tcacgaggac ctacttgtcc   5160
gtaccctact gtatttccta ccatcttatg ggtctcgata taagagcgaa catacgattc   5220
aacgataatg acatctttct gtttaaagtt acccattact tttagttgct cgtttgcaga   5280
gttaaaccaa aaatctggaa gaggagcaat catatcttga agcataccca tataagatac   5340
taattgagaa taatacccga gatcagcgcc aaaagcgttc gggccgtaga atttaccgca   5400
attactaccc ataccacctg aaacaccggc cattcctaaa aggaaatcag tgaaccatgg   5460
ataagttgca ttaccatcca ttgaagtaat agagccaacg tttgttctta taattcttgt   5520
tacagcaaat acgttagaac cacgcatatc aaatacgccg tgacggtatt tttcttcgtc   5580
atcaacaaaa aatacatgga aacctttatt caacccgtca aagtggtatt cgccataaag   5640
```

-continued

```
ttctaacgct cgtgaaatac aatcataaat ttgatctgta gttaattcaa catttacaat   5700
aggagcgcct aaacgacgta atattacgtc ctttaattct ttagggtttt gtgcattata   5760
acctgacata taaatccttt agggcccgaa ggcccttttc attaagctgt aggaagttca   5820
acccatgcac catctttgcg aacatagaat ttaccgtctg aaggagcatc ttcaatatat   5880
ccagcttcct taagagtttg gatttcagct tctgcagcgg ccaaatcagt ttcaagagta   5940
gcaattctag aagttaaacc attaattgtc gtatcgtgac ttttaactgt aggcaatata   6000
ccacgttctt caacagtcga accatttggg ttggtgccgt ttataagagt atttaatgtg   6060
tttacagaac ccttaatccc tgtggtatta gtcccgacat cagtttgaat gttctgaatg   6120
tcattactca tctcaccgat agatccttca agcgctcgag tacgataaag caaagagccg   6180
gctggttccg gtttcccacc tgaagcgtca acaccaacta cgttatttaa ccatgacaca   6240
ttaaaacgca atcctgacga agaatcagag ccgacaacag tgttcaatgc tccgatagca   6300
tcagtattga gtttaatacg tccttggatt gtagtaggca aatcatcggt gccaatggca   6360
gtttctactg tagtcaaacg aggtttaata ccacccgatt gattgagctc aagattaatg   6420
tcgtttattg ctgaactatt cgcattagtt gtagtaataa tagaagtcgt attaggatac   6480
ccaatagact gtttaatgcc atctaagtca gcattttgac gcgacaaagt taaatcaata   6540
ccggaaagac gactaaatac tggagtagtg aaagaagtgc gaggtcccat ttcttcgcgt   6600
aagtgttcga cttcattagt taaagagccg acgtcagaat cagcaaattt agtttctaga   6660
tcagttaatc gaacaccgtg gtcaacaatc acggagctat tagtcataat acggcgtttc   6720
ataccagtgc tatcatttcc tggagtagga accccattaa tatcttgacc agtatattgt   6780
cctaattcat ttttaatcca aagcaggtcg ttacgaacag ttctataaac tgaatctgtt   6840
tcctgattat aaacaccaat atcatcagta ttcgcatcaa tatgtttatt caaatcattc   6900
aattcactag catgggtttg aactgtgact ttaatgacat cgatatcttg ggtgttctgg   6960
ccaatctgtg caagtgcttc gacgtcccca gaaacatcta aaataccttg aataactttg   7020
atatcttcat tggctgtatt caaagaagat gctatagttt taatattaac atctaacgct   7080
tctacgttac gttgaacttc aacaatagga cggttcatta caccttcaga accgtatttt   7140
gtgtcagcac ctgttatttc ttcatcgttt ttaatccatt caatacgact ctgacccgcg   7200
tctggcgggc cgtcaacata tggtaaatct accagagtta tatcagccat tattttacct   7260
taataatata gtttaaagaa atattccatg gacgagtttc atttccaatt aattctggac   7320
gattcatggt atatttagag ttacgctgag acgctggatc aatttcatat ccttcgttag   7380
taaaatatga acggttatcc cagtcaagtc ctttacgagt accaacaaag tttgaacgac   7440
gagtattacc aaatgcaccg gaatcatcgt gttcgccaaa accaccagca tgtttatgat   7500
atgacatctg ttgtttttgc acttcaccga catatccacc agtacaacca actcctaaac   7560
gaggtttacc aaattggtca ttaccattaa cattagggtt agttaaatgt gtaccacgac   7620
ctgagccgcg aacaaataat ccacgcatat caggcaagcc cgggttagaa gagctaccac   7680
catatcgtgt cccaattctg gaagcatata ccggacattc tgaagcagaa acggtcccac   7740
cgtgacagaa gcgccagtca gaactcggta aactatctgc ggcccacatt gtaatagcgc   7800
caactggaag aattcggtct aattcatttt gagtcacaat acgattgcct tgaatataac   7860
caccggtcat attgacatta ccagttatat tagctccacc agaaccaacc gtcaacgtat   7920
tattaatgcg aagcgtgcca ttaatagttt gtccgcctcg ttggtggata acatcagcat   7980
tccaagcaag ggcagaagaa ccatcactac ctgattggct acccgcttgt gtagttaaac   8040
```

-continued

```
gaacaactcc acgtaaagaa gttgtagccc cacgcccgtt taatgttgcg ccggtcacta   8100
caactgaaga gttgttacta tttacttcag tctgtgtccc tagtttaacg acgcctttat   8160
tagtttctga tgctactgaa ttcataaagg tataaggtga aattgcatag ccttcacgca   8220
gggtgccttg ttgtgcttgt gcaactgtag ctaaacgaac aacaccggta atagattcgg   8280
tggcgtcact attatttgga gcaatttgcg aaataagttt aattgctaat tgctgtgttt   8340
ttaacggggt cattgccgtt gtatcgtcag aaccagctaa tgccgcagca gaagttgaaa   8400
ttttaattac accatttgtt gcttctgttg acacttttgt ctgaaataca ttgtctattt   8460
tttgattcaa tttaagcgga gtaattgatg catcgtcaat agctccggtt actgcttcat   8520
cttcagtagc ataacgagtt aaaccatact gagtttcggt tgcattagga tattgtagac   8580
gagcattcag tgttgccgga gtaacagctt tactattatc taatccatca ataacttctt   8640
gtggagtagc tatttgaata attcctggtg tagtagttgt tgcttccggt acgccattaa   8700
cacctgaagg agaaatagca gctaatgcgg cttggacatt agtgactgtc tctggaaaat   8760
tcgaccccgt agggtcgaat tcaacgtaaa tagattcgtt tgaaacgtgt tggtatgtat   8820
tgttattact catgaggctc tcacaaagtg gtagaaaacg gtaggagtac tatggttatc   8880
aagagtaacc gtttgggcac ccaataaatt ccatgttccg tatccggatt ttgcttcaga   8940
caaaatttct tgcgaaattg ttacaccaaa cgaagcatat gttggcaaca catgtcgttg   9000
gttatctaaa tatgtcacct gaagtttatt accttcggtc ggatggtctt tataagaaga   9060
aatagcgatt tgattagaaa tggcttcttg taaagctata cgaacttgtg ccgttaattc   9120
gttatcagtc ataccgattg atgctttaac agcaagtcca aatacgttaa taacgaccgg   9180
cgttccaggg gccaaagtat cgtcgagaac atcaccagaa aaagtccaat aatcaacttg   9240
tgctgtacct tcaggcgata cgcctgaagt gtttgttata acagtaccaa tatcagctcg   9300
tgccatatta tggacatcat ttattgcaga ttctacgtta gcatcataaa aaccgcgagc   9360
taactgagaa atagtcacgg aacctacagc ttggttgttt aaaacatcaa tttgagctgg   9420
attttttctg taatttaaaa aatcagcatg acgggaaata actcccgcct ttgtattaag   9480
tacagtcatt atgcaatcct tacccaacgg tatacagtta tagatggctg aatattagtt   9540
atagaacgcg ctggaacatg agatccatta gtctttgcat ggtcttcacg atatttagtg   9600
taaataggac cttcttcatc cgggtcatat tggcaaccgc ctataattac tgtaccatta   9660
tcatcagaaa taagaacctt ttcatcggtt tgtgtagctg gtaaatcagc attttctaat   9720
gtgatggttg ttacaccaac ggtaccacct gcggtatgag tagggttacc attgacgtca   9780
aggtcattat tatttaatgc aaaattagga tccgacgcgt cgtcattcca acctgctaat   9840
actttgcctt gtccccaaat tttccacgaa ccaaaaccta aataagttgc cggattatta   9900
gggttaaccg cattttcgta aatagtcccg acaggataaa ttgtatcaaa tattgctgag   9960
atagtcgaga attcacgttc atacttagga acaggttcta cattaggcca gccaatttta  10020
tcaaaatcgg ttaatgcaac atcgccagta atttcaatgt tagacccttg agaaacatat  10080
ttctcgtcag tggcatcaag gatttcttcc atttcaagaa gagttcctaa atcgttatta  10140
aaccatgtga tggtaataat gtcttggtct tcaaattgac ggtcaaacag aattgcgcta  10200
gggatattat cagtatactc aatcgcataa tctgtatacg attgagtcca tgtcccacct  10260
agattagcgc atgactcttc agaatcggca tccacacctt cgcaacggaa aataggagtt  10320
ccaacagtac cagctaattc ttggagaata ccattgaagc gaacttctaa cgaattcggg  10380
```

-continued

```
ttaggtggtt ccgtaggatt aataccaaat gctgtaaatg gaatagaccg gaacgtactc  10440
aaatcagtga cgtaaatact tccgtcaata gactttttag cagtcaattt actatctaaa  10500
atgcgaactt ggcgacgagt atatgaacta cgccactgag aaacaccatc taggaatgtc  10560
tcaatttgta cggtgtcgcc aacattacat ggttggcgta atctaatatt aaatccatca  10620
agtgcaacca gttcaccagg attagcgcct ggagaaccaa aatcactatt atcactgaat  10680
acatcaccat aatacaattc gttgccacga tgttttacgc gaatgttgtt aacgttataa  10740
gaggtcccgt taaaaacatc catgaaatcg gtctgacctt gggtttcaac cagatattct  10800
ctacgagcaa cattactaat gtcagagcta actattttat caatttgttt gttcttgatg  10860
tattcccaac gtccaggagc acaataaact aattctaaat cagagaactg aacattaatt  10920
tctaccggag atgaagaacc tttaatcgtg tccccgtttg ccggaattaa agtaacaggg  10980
ttaatgttcc aagttgcaaa tacgtcacga gcacgaataa ctttattata gtctgcaatt  11040
gtccctttag gaagatttac tgaaactcgt ccagaagtag tattaattgc ataagattta  11100
ccccaagcag cattaagatt aagaccatca gccgcatcat aagtcttcca tgcgccagcg  11160
gcataaggaa cttcaccatc acctaattca taatagattt catcaaagtt ctcatttatt  11220
ttttcaccac ctcgacgaag gtaatcgcct tgtccgtcat caacgacgtt accaatttta  11280
atattttgtt tcattattga gcgaccccaa ttttctgagt tgagataatt ttaactgctg  11340
aacgtaatcc aataaatatcg gatgtaatcg tcatagtagc aaagttgtta ataatactaa  11400
agctaatatt agcaatctcg tcggtttcat ctacattacc aactcgcatt actgcaaatt  11460
ctgtagaaag aacttctgag ttaattgtat ctattagaat atttatttcg catgttttta  11520
tttttctacc gtcggcggat tggcatgtaa caagcaattt agccatgtta taatccgtgc  11580
gataaaacag aggaatagaa actgtgtttc ctgtaagact ccaagtccca tcgacaggag  11640
attctttctg cccaaacatg ctatcagtag aataattcca tactgaagtt ggcccattaa  11700
gttcaataca acgaagaaca acatgggtat aaggggtgga aataacaaga ttattaagaa  11760
cacctttaat tgagccatca gttacttgga tacttaaagg attgttaaca gaaatagacc  11820
cattagagtt tatgaattct acagagtcac ctaattcagg acggtcaata ataacaatca  11880
caccaccatc agaagcatca atatcatgca tggtgcctgg tttaatagga gtttgataat  11940
cgacagcctt tcctttttga taatagcctg tggcatgaat agtttgacct gtaggtccgg  12000
ttccatctgc tacggccatt ttacgttgat cgccaaatgc attgtaaata gcgttgatat  12060
cgtcatttat tttattacca ccgtcgaata agatatcacc tgttgaggca ttaccaattt  12120
cgccggtatc gattaattgt ttaggagttt gcttaaaaaa tgccataatt ctgccttttg  12180
ttgtccgata ttatattcta tttatagata caaaaatggg agcccgaagg ctccctaatt  12240
aaaacataaa caaaatgtta atttcttctg tttggtccat tgccataata acaggtggtc  12300
ggttttccat ataaatcatt tcaccggaat gacgctgcag atctctaggg tcgtaataat  12360
ccttttctgc tttaacatta gggtcatttg gatttttctt agcttctaac gggtttgtga  12420
taattgatat ctgtctaaaa cccttgttac caggcaaagc tgcctcaggg aaataaacag  12480
aatcaaaata tgctttaaac cgcatcgtat tagctttaac acggtaaatc aagccgtagt  12540
catcttgttg ccaagttaag ttattttcat atccccaacg ggtggggtct tctttaattt  12600
cttccggcca tggaactaca agatattcgt tagtgcaacg gttaattgac acatcggcag  12660
gaatctcata aagatactcc caaatatatc catcaccggt ttcgataacc ccattagcat  12720
cgcctctgcc ttcaggagga gacatagaac gaacagacgg agtccattta ccacctaatt  12780
```

```
taagacattc atctttatta tctaaagatt ctattgaaca gagccctacg tcagggacat  12840
ctaaacaacg gtaaattaac caaccagctc caacttctgt cgcgttgtac ggagcagtat  12900
tacatgcgac tatatcgtta attctaaacg tgtaagggtc tggatatcgc acatctcccc  12960
aatcacgtct aggaataaca gaatctaaca ttgaaggtaa aactttaact gtacccatca  13020
tatgggtcca catatcagta acaccaagaa cagaatctgt aggataaggc ggggcgaagc  13080
ccacctcatt ttcatttgac gcccaaggct ctgaacgtcc aaacgtaata taaatggagt  13140
tcttatcatc tccatcccca actgaattat aaaaattcag cattttctct gttctaaatt  13200
ttgatgtaac tattgcacga tagataacac ttgaatcatt catctaattt aacctgcggt  13260
ggattcacgg ggtctcttgg atttcctaca ttatcgatta accgctgttc aaccaaatct  13320
ctaaatctag agaatgttgt tccggacgca tcaaataatg ggctcatcag tttacgtcgt  13380
tccgatggaa gttgaccttg aaatattgag ttattgtttt cagcgttata atcttcaggc  13440
aatggataat cttgaccagc catagggcct atttcatata tcgcttcacc tgtaataggg  13500
tcaaactcaa catttccttg tgggtctaat ttagccactc ggtctgcata tttagtcggt  13560
aatccagaat cccacttata gtttttgtat ttattaataa tggtttcaac atgtttaagt  13620
gttaatccag tgttaataaa cattgtgaga agagtaattg cgataaatcc aaatccaacc  13680
ggatgaacaa aacgtaatac gtctgatttc caacgagatg atggaagttt agatttaatc  13740
ttcattacgt agtatgctct accacgattt atgtaatcga tgttgttctg agaaagctcc  13800
ttacctttaa taccacgaac aatttcacct tcaaaaccag ggagtctttc agctttaact  13860
tcctgtcctt gaattaaacg acctaagagg ttgtgaattg ttacagtcca ttgtaattta  13920
cctttagagt aacttctctc gatatacgtc acattacaac gtcctgtagc ggtgtatata  13980
gtttgtccga ccaaatcttc tgtcaacgag tcagattcaa tgatgatatc atattcggtc  14040
ccggaactag attcaatttc aatttcaaca tcttcgttat aaagcacttt aaacaagaat  14100
ttatatgatg cttcagttcc tttagttgaa tagaagtcat aacttcttga ttcaaagaaa  14160
cgagacacta aatcgcgttt ttcggcgttt aagtaaatgt ttcgtttata aatctcagac  14220
cataaatatt cccacgcatg ttcttcgcgc ggatattgat ttttaataag atttaaaagg  14280
ttgttataat gggtcccata gccgtcagaa agatactgaa tataagcctc gcagaatgct  14340
tcgaagtttg tattatctaa aagataagac tctggcatca ttgtagtgag caatggtcgt  14400
aaatctgggt cagcaatacc attctcttcc acaggagtcc atgtggtatc tttttcttgg  14460
ttttgtaatg atgctgttaa gaatatatta gtaggcttcc aaattataga aacattatct  14520
ctaacacggt aactaaaatc ataataagaa ataatctcac ctgatgcttt atagaaaatc  14580
atgccagatg catatttttt aaatccggtg aaatctacgt taggcatcac tattgtacag  14640
tcaccgccat tccaatattc atgaacttca cggtctgaag aactaagtgg atgattctca  14700
ataaccttag tgtaaagtaa atcagaataa attacaacgg ccttgtctga gttattaatc  14760
caacaccgag taccagactt tctagaataa ctaaagaacg gctcagcata gtattccatc  14820
ggttgaggag tgaacgattc ccattgagag tcttcagttg aaataaatgc catcatatga  14880
taatgtttat cagccaacca ttcgcgagga tactcatatt taacagcacc gattaaaccg  14940
tacttgactt gtgtttttgg gtcatcaaca atatctgatt ctaaaaattt aaaattacta  15000
gatgaaatag ataactcaac accatcagta gacatactgg tgtacccggg ttcaatacga  15060
cggcgttctt cttcagtatt accaaacaca cgtttaaatg tgccagcatc atggtctaga  15120
```

```
acgtaaacac ccttatcaac agaatcaaca ataggagtgg tcctcgggtc gtcattaata  15180
ttaacaactt caccgataat cagtgcaaat attttaccac cgacagaatc cattttatag  15240
caaactgcct tagggttacc tgtgatgtta aatgtttctt gttcaaacaa acgttcggaa  15300
tatgtcggag ataatgggtc tgaatcaata ggggcattac tagttttaat aaaacgaact  15360
ttatctcgag cagcaacgta tacataatcg tcattgcaaa cgatagcttc tgcaatacgt  15420
gatacgttag caggtaatga tgcatagtta ccaaatattt ctacatcaaa tcctaaattt  15480
aactggtcac cgattttagc aaatgttata tcttgagaac taaatctcac atcatcagcg  15540
gaccaacgaa cgtctgttga tttacggccg taaaataatt tatcataccc aagaacatat  15600
gtggtgtgat ctgtctggta atacactgtt cttgatacag ggtaccctac acggtcatta  15660
aacaatttaa ccgatttcca ggtttgtccc ttatcattag agactttaac cacaggctga  15720
taccgttcaa acaaataaag aattccttcg gattccatca aataaacacg gtttatatca  15780
tgacacacct gttgaatcga accttgaatt tcatgatact cattttcgcc aataatgaaa  15840
tttttaatag atgaaatatc agcataagca gggctaaatt ggaacgattc attcattaga  15900
gctgccatta tagtgtcgtt attaaaatcg acataagccg tgttgttatt tgtaaatttt  15960
tctctaataa aagtattagc caattgcatt tcaatcatat gttgaaatgt ataagcgttg  16020
gtctgaaatg attcaaatat ttcggtatat acccaatcag atctctcgaa gccttcagcg  16080
gcagttgata cacgaataat ataagaagtt aatgggtcta agctattttc gaaccagtcg  16140
ctattaggag tatatcctaa atttacccat ctgtagctgg caggggggaat tatttccccg  16200
tctgccgttt tagtctcagc gatttctacg aaatagtaga aattagcacc aacgtcatcc  16260
cagcgtattt gaacttggtt agcggacaac ttggatattc tgagacttgt gactgctggc  16320
gcttttactg tcattgtgaa ataggctcca aatctatagt taagtactga ggacgtaagt  16380
cattttcgaa tacgattaaa gaaccatcct ttgtaaaaat aatatcatct gcagggtcgg  16440
aataaagttc aattgtttga acttcaaaac ggtctgaagt gaggtcaatt ttagcaatgt  16500
tccaataaat cgaatcggca ggataattca cttcaccaat tgaatagtat ttgtttcgtc  16560
cgtcagtaac agtaagttta ttaaaatcat tacctgtata aggttgtata ttttcgtttt  16620
caacaacatc accgtctgca aatggaccaa taataacttg acctatgcca cggtcattac  16680
ggtcagaaga tactatgcga acaccatatt taatagtttc gtttgcattt tctggattag  16740
gtctgtgtga atcaaacgag aatatattag attccatcga tctatcttta atctgattat  16800
tgtatttaat accggcctca ggcgttttat agaagttttg tacttcgcga accatttgaa  16860
tagtagctga agaaccaata atagaaatat ctgcgtcatc gacataagtt agcattttag  16920
attttgcaaa cgatgagtta aaaatttcta catcttcaat ataataacgg tctattttat  16980
taataatctg cccttcaaga tattgttctg attcttggag tttattcaac gcgtatgtaa  17040
ctttgatatt cattttgata aacaaataat caggcgaaat aacaacaggt gtaatagtcc  17100
ctaagttata atcatttaaa tagtttttga tatcatcacg ttgaacagaa gtcaaataca  17160
atccagattt aggcttagca gcaatatatg cgtaccctgg tttagatgaa tctgtgaatg  17220
tttgaaccgc ttgaataata gaaccaaacc gctcagagac gaatgtgtca tagtcggaag  17280
cggttacaca acgttgttga gtttcgcgtt taattgtgcc taattcgcgg atacgttcaa  17340
tatcttcagg gtcgccgcca ccatcagccc caacaaagtc cgggttattg ctagggttct  17400
cgttaatatc gattaccgtg atattagcta atgtatcagc ataagaaaat cctacagcac  17460
cgttagcatc tgcgccgtta gtagaaatat actcaattac gattttagaa ccctgaacag  17520
```

```
gtttaaggcc accaatatag ttagatgtta acgcaccttc tgatgtgtta atagaaattt  17580
cgccttcacc aaaataaaat tcggtgttcc catcaactgt ttcacgcata taatagattg  17640
ttgacgtaga accagcgtga accatcgact tacgagtcca gttaatccat tctgctccgt  17700
caacatacaa cttaaccaaa ttacggtcaa tattcttatc gcgaataatg ataggtttta  17760
atctatcaaa tgttaattca gtgcgaacaa tacgtccttg agctaatcga agacgtggaa  17820
aatatcggtt atttttgtct ttaactacaa tgacatcttc agtagaaaca aagttatacg  17880
ggttaacaga agtatcttta gcgtatgcta agaaacgagt gccacgtgga atggtgatat  17940
agtttctatt taatgcatcc gtacatgtga gcataatttc tgtttgtgct gctgatttag  18000
atgaaggcag atatccgtta tcttgagccg cttgtacaac agaactacgc aagtttgcag  18060
tacgcataaa actttcatac actgcactat tactgaactg ttggatgtaa agagtgttat  18120
atgctaaaag gtcacataat acgtttaaac gcgaaccttc aaaatcataa tcaagaaatt  18180
cattctgtcc attgagccat tcgataatgt tctgtttgat ttcggcaaat gtgcccccga  18240
taaaaatctc gggaatagca ttcgctgttc gggttaattg ataatttaca ggagtgtttg  18300
ccattttaat tcctatttta taaagacttt tgacgaggcc tgagaaacag tatccccgca  18360
tgaaattggg tcagccattt gaacagcctt tttaccggtg acgtatactt tagatgtacg  18420
aggttcagta acacctccat gagtctcgta tggtttttta atttctgtat gaggtgttat  18480
ttggtctcct gccacaagaa caggaatacc gccggtgaat actttagatt gggaagcatt  18540
tattacagta ggaggccatg cttcatgacc tgttgtaacg cacttgtcgt aacttaagcc  18600
agacatttc acggcctcac ataaacatag tttcgtaatt gttgtgccca tttgctccaa  18660
tttcctacta tagtttttgt ataaacctta gtaagagttt tttgtactgg agccggtgga  18720
ggttctgtac cagaggcact tctagaatcg cctgatgaac tttcttcttg gtagttataa  18780
atcatttcaa ccgtataact aaacactgta cgaagattct gaggagctct ccacaaatat  18840
aactgtgtgg attcatcttt tggtaaatca tcccatgaag atgcagtttt aaaatcatca  18900
tttaatcgat atttcaatgc atctgaagaa aagctaaaca cactttcata tgttccatat  18960
aaacgatcac catctaccgt aatgccttgt gtcggttcat aatctgttat atttattgac  19020
actaaagttt cggttgtttc taactgtgga gtaaaaagga cgtcaataga cgccccttcc  19080
atgtcttctc ctaagtcggt atttaaagga agtatttgtg ccatatatta cccaatatca  19140
atacgagatc cgtcaacagt gtattgtcct gaagctactg agctcattgt agacattgtt  19200
tctgcccaat ccccggcaac agtcatatca acattaccgt taacagtcca tttaacgttt  19260
ccgttgacgg tgtaatcatg attcccttcg acctgagttt tagcatcacc tttaacaaga  19320
atatctgcat ttccgtcaac aactattttg atattaccct taacgtaaag agttccatcg  19380
ccttcaacag ttttagattg gttaccacga ataaagattg tgtcattgcc gtctatttga  19440
tggaggcggt ctgccatgtt ataatatatt tcattagcac caacgttaac aagtttatca  19500
ccagaaatca agaagttccc atcgccatta gtgatgtcaa aaaggtcttc tacagtttta  19560
cgagtacgtc gcccagacgg agaaacttcc tcatatgacc ctgttggatg aactaagcga  19620
taacgttcat tacctggagt atcgtcaaat tcttggatat gtccgctttc tgtttccata  19680
gcatgaacgt atgggtactc accacgataa cttgattcag gttctttaaa aaggatacgt  19740
gaatctaacg gaacaggcgg acctgctggg tcttctggat cggtatttct agtaactaaa  19800
taagcaccaa ctcctggtga aggtggtgtt ttaacaggaa cgccatatga ttccatgtta  19860
```

```
ccagttaaaa taattgttgt tacacgtgaa gcacgccctt tagtctgttg aaaccataac  19920
gaatcgcgtc cagatttgta tgcggttttc caatcacctg tggccattgc tttaagcata  19980
gtattgaatt ttgctacacc accgacgccc atctggaagc acatgttttc taatgccatt  20040
tggcgagatc tgttcatttt agcataaaca ggacctactt tagaattaga acgaatgtct  20100
ttctgcatct tagcaaggtc cttctcaaat aacgctgttg cttcttctaa tgtaatagtt  20160
cccggatttc ctgttacttc acgccctact tgatcagata acaatttatt aattcgagac  20220
atatctcggg tcttttccat tacgataagg tgtccaatac ctactgtagg atatccgaga  20280
tggtcccaat acactttatc acgaagacct tcgtcacgac gtaacatttc tgttattgta  20340
aaattagggt catcatcttc cggaatattt gctaaatctg tatcatccgg gtttatacca  20400
taatccaagt tgttgtcttg aattacgtta gagttcgaat aataaccagc ttcaccacct  20460
tggtttaata cgttcgtatc attacctaaa cgtcgtggat attgacctgt agggtcggaa  20520
aaaccttcga gtctattagg cttttcacgt acgattccgc cgtatgtacc aagtacaatc  20580
ccgtttgttt tccatttgtc taagaaatga ccatatactc gagttccttc aacaggacct  20640
gtaacagaac caccaatacc tgacattgat gcagacgtaa taggttgaat aacagtcatc  20700
catggaagtt tttctgtagg aataccttgt acatcacctt gtgttctctg cgctggatga  20760
agaccaacga ctcgaactcg aactcgccct tgttttaacg ggtccattct gtcctcgaca  20820
acacccacga accaattaag gctactgcta atcatttcca ttatgcaatc tccatctcac  20880
gaatcaaatc tgtgataaac gagtttatat cttcttttgc aacaattttt attttacgaa  20940
gtttttcatt atctaatact gccgcttcat aagtatctac tgcagctaaa ggtcctttat  21000
attgcggata cttacgagct tcatcacctt tatcgtacca cactaaaggc tcgtctggat  21060
atgaaaccaa attgtaaaat ttctcacgat tttcattaat atgataaaga acttggtcgc  21120
cgccagcatt agcatatttc tgaatagaag cttgatacgc tgcttcctga gatgtaatcc  21180
aaccataata cggatcatag ttgtcattac acatcaaaag gacccagtat aattgagggt  21240
tgccataaat tatatttgct agttcttcag gacgcggaga gcctttaata taataagaac  21300
gtaatctata attggcagca acacgcttaa agtactcttt atagttacga aatatgtctg  21360
tcataggaat agtaggtgcg ttcttattaa ctgttttagc actatatcct attgggtcga  21420
agaatgtaaa taacaagata gtctccttcc aatatgaaat tggtataaat aataatacta  21480
tttataagga ggacaacatg gcctactctg gtaaatgggt cccaaaaaat ttaaaaaaat  21540
accgtggaga ccataccaaa ataacgtatc gttcaaactg ggaaaaattc tttttcgaat  21600
ggttagataa aaatccagaa attattgcat ggggtagtga aacagcagta attccatatt  21660
tctgtaatgc tgaaggtaag aaacgtcgat actatatgga catatggatg aaagatgcat  21720
caggtcaaga gttctttgta gaaataaaac caaagaaaga aactcaacca cctattaagc  21780
ctgcaaatct tacgactgca gcaaagaaac gttatatgaa tgaaatatat acctggtctg  21840
tgaactgtga caaatggaaa gccgcctcag ctgttgctga aaagagaaat ataaaatttc  21900
gagttctaac cgaagatggt cttagaaaac tcggatacaa ggggtaatta tgagcatatt  21960
ccaaattata tctgaaggcg tacaagcccc taagattgct cagtctatga atgaaagaaa  22020
atggattgag ataggattag aatacaagaa agctaaagag aaaggaatca ctgcaaaagc  22080
atttgcagaa tcaaaaggaa taaaatactc gtcgtttaca tctgcaatgt ctagatatgc  22140
atcatctatt aagactgcac agaaaattga aacacttgaa tctaaaccta aaaataaact  22200
caataagcaa gaacgtcaac ttctgatgat aaactcgttt cgcagttcaa tacgagaaaa  22260
```

```
gattagaaat gaaggcgcag cagtaaacaa caaatcatct aagtggtttg ttgaaacaat  22320
taagaaaagt gtaaaaggtc ataaagtagt caagcctacg ccaggcaaaa tttatactta  22380
tgtgtatgat gctaaacata aagatactct gccgtattgg gaccgatatc ctttgattat  22440
ttatttagga ttaggtaaac ataatttgat gtacgggtta aacttgcact atatcccacc  22500
taaagcacgt caacagtttc ttgaagaatt gctgaagcaa tatgctagca caactactat  22560
tactaataac acaaagttga agatagactg gagcaaggtg aaaggatttc aaggtgctga  22620
caaaatgatt aaagcatacc tgccaggcca cattagagga acaataacag aaatagctcc  22680
taaagactgg gctaacataa tcatgttacc tactcaacag tttatgtcaa aaggaaaacg  22740
tttctctgcg aatactgttt ggaaatctta attctattct cttccgttct tctgatattc  22800
tgttgaaccg gattaatgga agagacctaa aaccattata ctgcattttt attaaagcgt  22860
ttttgaggtg cttatgactc gtccagcgag acagattttt aaccaaacaa atataacaaa  22920
ctttgttgtg gatatcccgg atagtacacg aacttcaggt tttgtgctca atgcccaaac  22980
ggctccattg ccaggtgtga gaattcctgt tgttgaaact gtgacaggca caatggggtt  23040
aggacgtgca atgcgtgcag gcaccacatt tgaatatgac ccttttgttg tacgatttat  23100
agttgatgaa gacatgacgt cctggatgaa catgtataaa tggatgctca gcactaataa  23160
ctatataacc ggacataata cggcccactc cgatggtcct gagtttgtta ctttgcacat  23220
tttaaacaac aataagacag aagtagtttt gacggcgaat ttctataaac catggatttc  23280
tgatttgagt gaaatcgaat ttagttacac cgaagactct gaccctgccg ttacgtgcgt  23340
agcaactatt cactacgcgt atatgacgat agaaaaggat ggagaagtca ttgtgtctca  23400
acaaccacgt caagcggtcg aatctaaatc catttctaga cacccttcct tgcgttaatc  23460
gcttctagct ccgtatgtta taatcactca taaattatat gaggaaaacc tatggagcta  23520
atctttttaa gcggcatcaa acgtagtggt aaagacacta ctgctgatta catcaattca  23580
aactttaaat ccgtaaaata ccaattggca tatccgatta aagacgctct agcaatagcc  23640
tggggacgta gacatgccga aaaccctgat gtattcaccg agttgaaata tgaatacttt  23700
gaaggtgttg gatacgaccg tgaaacacca ttaaatatca ataagttgga tgttattgaa  23760
ttaatggaag aagcgctaat ttatttacaa agtcaatatt taccaattaa taatgttaaa  23820
gtattatcat cattagaagg tgggtattca tatctagata ttaaaccata tgaagccctg  23880
cgtgaagcta taaataatat caacgacaca tggtcaatcc gccgtcttat gcaagccctc  23940
ggtacggatg ttgtcgttaa tttatttgac cgtatgtatt gggttaaact tttgcatta  24000
aattatatgg attatattgg aagtgatttc gattactatg ttgtaaccga tacacgccaa  24060
gtccatgaaa tgggaaccgc tagagcgatg ggtgctacag ttattcatgt ggttcgctct  24120
ggtacggaat ccactgataa acatattaca gaagctgggt tgcctattga agaaggcgat  24180
ttagttatta caaacgacgg ctctttagaa gagctttatt ctaaaattga aacaatctta  24240
aggtaataaa atgtctactg aaactatcga aaaactgcag tctgaaatcg ttactctgaa  24300
atctcgcatt cttgatactc aagaccaagc agctgctatc cagcaagaat ctcagcaact  24360
tggtagtgct cttgctaaaa tcgctaatct ggttggtatc actggcgaat cagttaagat  24420
tgatgacctg gtagaagcag tacgtgaact tgttaaagct gaaaccacag aagaagaata  24480
atgaaatttg aggacttttc acaaggcctc tacgtcgcag ctaagttttc agaattaaca  24540
cttgatgcgc tggaagacct ccagcgtaaa ttaagaattc ctaatccagt accacgtgaa  24600
```

```
aagcttcatt caacaatttg ttattcacgt gtaaacatac catatactac atctagtggt  24660
agttattctg ttgccgaatc aggacacttt gaggtatgga aaactgacga cggcgctgta  24720
ctggttttag ttcttgattc tgaatatctt agatgtcgtc atcagtatgc acgagcttta  24780
ggtgctactc atgatttcga cgactacact ccacatataa cgttatcata taacgttggc  24840
caactatcat tcagtggtga tgtagctatt ccggttattc tcgaccgtga atacaaagaa  24900
ccattaaaac tagattgggc cgaagatctg aaataatttt cacaaaacag tttacataag  24960
gatgatggtg tgttactatc atcctatcaa ataaataacc taaaggaaat aaaaatgaaa  25020
acctataaag aatttatatc acctgttgct aacgtttcta ccctgaccga agcaacccctt  25080
acttccgaag ttattaaagc aaacaaaggc cgtgagggta aaccaatgat tagtctggtt  25140
gacggtgaag aagtaaaagg tactgtttac ttaggggatg gatggtctgc taagaaagat  25200
ggcgctacta ttgttatctc tccggctgaa gagactgcac tgtttaaagc taagcatatt  25260
tctgtagctc agcttaaaat tattgcaaaa actcttctgt aagtagttta catgccgata  25320
ggactatgtt atagtagtcc tatcaaaaca aaatgagtaa atggagaaat aaaatgaaac  25380
gcgctgaact gattcgtaat gttgctgtag taattgcttc aatggctttt agtttttcga  25440
tgtttgtagg attcatttgc ggactactga caacaactga aaattctatc tcattggtag  25500
tagcatttct aatcggctta atcgctatcg ttatggataa aattgcaaaa ggtgagtaaa  25560
atgaaatatc acgtatatgc ggattttgaa gcaaatcctt ctaaagaccc tgattgtcgt  25620
ttgatacgca gaccatttga ttcagcagct caagcatggg cttggattaa atctaaatcg  25680
cctggttata tgttctttga agtagtcgat gacaatggta cactgcatcc ggcccctaca  25740
gaaactatta atttccttct gtttgctggt tatgactgtt atcctcttgg tggtattgac  25800
gaccttgttg ctacaggaaa aactgttgag gctcttcgcg aaatttataa aaacgcagaa  25860
gaaaattttg actggtatca tattgttgat gctcatacct ttgaagtggt ggaacactca  25920
tgattcttta tgctaaagta aaatctgtcg agaatggata tgaaagcgat caacgtgcag  25980
ctaaagcact agtcgatgat tatggcattt taacatattt tgaagttgaa aaggtttaca  26040
tcgaccgttc gtcttcgcag gttaaattac tctgcgaaga cgataaattt aacacagtta  26100
actttgattt ctttattgaa acagaaaaag gtcctcttga atatgatatt ttcaagaatc  26160
ctttaaatct tgaatgtatt gaatatactt acattaatat ggtatggtga ttaaatgaat  26220
attcgtttag gcagtacaat tcctaaaggt tacgtaattg atgtcactac ctatgaaaat  26280
gacggcgaca actataaaac caaaacattg tttgaagtgg aagagcatga gctccaacag  26340
tttaaatatc tcttgaagaa atttaagagc cgtcattcta gcaccaaagc tgaacgttac  26400
tgtggtaata caccattcgg tcgttgctcg cttattatct acgaatatct ggttgaagga  26460
ctgttctcag accaactcca accggaattt attaaaaagg tctttggtat cgaagtagac  26520
cttggtgata aatctgaaga agacgaagcc cgtgtattcg acctgttctt tgtgaaaggc  26580
gatgagatat ctcaaggact tattgatatt cttggctatg cttctgaata ctacgactat  26640
gatttcttgc gtgtagttga acgtgttgaa ttcgcttata ttgaagaaga aattgttttg  26700
ccaaccgtta aaatggttga tttgctttaa gaattatgtg ttattattaa ttcataccct  26760
ctattaccaa aggtactcta aagtgccttt cataatagaa agttatttag gccctgtagc  26820
tcaatgggag agctgtcagc tcataactga taggtagctg gatcgaaacc agccagggtc  26880
accaatccga ggcatagctc aattgtatag agcaacggac ttctaatccg taggttgaag  26940
gttagaatcc ttctgtctcg accaacttca agcgaggaaa atatgaaagg caatatttat  27000
```

```
ttggtagttc atgatttaac gttttatttt aacgaacagg atacagttat ttccgaccgg  27060
ttgattaatt cgttatatca acacgctgat tacgtttatt ttaaaaatga attcggacat  27120
tggaagtttc ttaaaaaccg ttccgggtta actagttttg aatactttga ccgtaaagac  27180
cttttaaacg aaattccatt acaacatcgg ttccagaaac gcgaatcact atactattgt  27240
cgccatatac caaatgctga atgtgtttat gaagcgatta atctatggcg tcggcgtcga  27300
gagcaaattg atgatatgcc aaaataagaa gccgggtcgc taccggcaag tcgtcggact  27360
gatgttccct gagtaaggac tggtcttaat aaatctttac gatttgttaa tatcccctta  27420
catcacagca gaaacggcgc acagaattat cgattcgagg aaatatcttt gccgtaagcc  27480
gagtagcgtt tttgacggaa cgttcggata tggtcgagat atggcctttt aaaaatattg  27540
agtagcgtca actgcttaat aaccgggttc gaatcccggc gtttcgtaca aacacttgcc  27600
ttagcaggtg ggaccccgac aaggttgccg caaggcatag ccccttccga aaggttgggg  27660
ctttttgta taaatatagt aaacaataaa cctactttct aaggaccatc aatgtatact  27720
tttaatgaat ttttagcaga aacggaagta atcaccgaag ccggtgtacg tatgacaaaa  27780
gagaaatggc aagctgctta cgatgctatt tctggtacaa aaactagtac agagtttttc  27840
aaaaacgttc aagccatgta cggtatcgac acttccagcc aaaaagaata ttacagagct  27900
tctaaagcat tcaaagatat tgttagtggt ggtgtttctg ctaaatcggg ttcgcctaaa  27960
gtaaaacctg ctcctaccat tcctaaacct gcgaccccta aagcagtagc aaaacctgag  28020
cctaagccgg aagtaaaagc aactcctaaa gctcctgctc ttaagtttga tacttctagc  28080
ctggaaaaaa aatataaaca actatcttcg cttgttcgtg atattgaatc cgatacatct  28140
tcactcgttc gtgaattcaa tattcttcgt aatggccaac atatcaacaa ccttgatacc  28200
ccagaccttt atcgtcttta tttgactatc gaaggtttga agtatactca accacttcat  28260
gatgagatta aagaaaaact tcgtcaggca ggtcgtttgg ctgctgacgc tgctcagtat  28320
gcaaaaactc gtaagtaaag aatggggact tcggtcccct ttagggggtc tataacttac  28380
tgaaaaagtt gtttacttct tccctagatg tgatattata gttctatcac caacatgagg  28440
agaatattat gagtctttac actgaactga ataaaaaatc tgaagaatcc gctgaaacta  28500
tttttaaaaa cgtgcaaaag cgtattttag aaaagatgta taacactgca gctaaaggtg  28560
aaaaatcttg ccggtttccg atgaggtgtt cttccgattt atgcgcaaat actattgaat  28620
ggctggaaag cgaaggtctt acggtagaga aaaacccggc gacttctatt gacagtgaat  28680
catatattag tatttcttgg gataaatcaa gggtagaaga gaaagatggt gattgggttg  28740
tagatgttaa aacttctgat ggcggacgtt ctgttgaagt ttcagctgta gttaaaggta  28800
cccacgaaca aaggacttgg ggttggggtg gtgaagaaaa agaaattgtt cttagtgtga  28860
ttgccaggtc aactagtaat aaaattgcac aaagcatcat tgacgctgca attgctgaag  28920
cagaaaaaat ttgcaaaatt aaaaataaat gatgtacaaa cgccaaggac ggtgttacta  28980
tagacctatc aactacagag gagaaacaaa atggctacag ttagtattga tgtcgttgat  29040
tatgaataca ccgaagaagt tattcgcaac cgtcaccctg aagttcgtat cgattcagtc  29100
caagattcca agttttggac aaccgagctt aatctgagtg gtccttatga agctgttaag  29160
aagttcatgg ttgaagaata ctgcgaaggc atgcacccgg aagacgccga gttttatgtc  29220
aatttgatta aaaaataatt tacaaactct tgagagcaga gtataatgct ctcattggat  29280
aataaaccac caattgaaag gtaataatat gaacacactg aagaaacttg ttgaattcat  29340
```

-continued

```
ccgcactaaa cttggtactg ctatggctaa aaatctgact gtcgaagaac agtataacgc  29400
agctgcagat aagttgatta cccaaatcaa agaactaaaa acggcttctg ttaaatctat  29460
taatgaagaa aaacgtattc gcgaacttgt tattgaaaag aataagcaag ccgcttctaa  29520
ggaacgtgaa attcgtaagc tcttggctga aggacaagat gttaccatgc atgccaagct  29580
tggtcttctg tatcgtcgaa ctgccgaaca acttaataca aaagctgacg ggtacgctgc  29640
tatgcgaatt gaaattgctc gtaaggtggt tgaacttgat gatgctcgtc agaacctggc  29700
aatcaaactt gaatacattc gtgaaactcg agcggccaat gcccttggta tctctacggc  29760
tgatgatgta attgaaatcg ctgcactgac taaggttgat atcgaagaca ctctgactcg  29820
tgttgaaacg ttcaatggca ctccagctgg tgtcgaaacc acttctgctg atgtacaaga  29880
atatattaac tctttgaaat aaaataatac ggaggactcc ggtcctcctt ttggataata  29940
aaggagttaa catgcgaaac caaaataatg atattgactc aatgttcgaa gagttccgag  30000
ataaggtaaa tccacctacg tctttagttg attcattacg atatgttgca actggacgta  30060
aatggtactg gtcgtcttct tatgagacaa ctgaatatgc aaataaccga aaatctttat  30120
tagccccagg tattatgatt catgatatcg gagctattgc taaactagtt gcagtccatg  30180
atattagatt cactgatttc gttgctccta cgtggtctgt ttgttgttta aacactgaat  30240
gggaatatat cagcgaacgc tctgaagatt attatggttt tagagacaag cttttaaggt  30300
ctaacatgtt ttatattgat acagaagttc tggtcaataa taaaaaatat tactttacgt  30360
taatcgtcga ttctgaaact atgtatgaag gcaagccttt gcttaaaaga gttgatgctt  30420
taagtgctat tgatgcgctt tatgaaacca tggttgttag tcctaatttc actaacaatt  30480
taatccttga gcaatttatt atggaatgta gagaatatgt caaagccaac cctgtacatg  30540
ccaattaagc cctgggcgta tgaatacaag cgtaaattaa tcccaaatga agtactattt  30600
ggccctattt tagctttagc gtttttaatc tttatgatta taggagctgt tttagattcc  30660
aataaagtta tatcgtctga tgcagcgttt tcattaatgt tcgtcgcacc acttatggta  30720
ccatttttat taatgcctat taactgggtg ggatattggt accaaggccg tcatcacagg  30780
gctcgagttc gtgagtggaa agttcagtgc gcaaaagccc aagctcagta tgatgaagct  30840
gttaaaaagt atgaatatga agaagctatg gaattcgtta aggaaataag atgcaaaaac  30900
ctcaactctt aaccatatgg ccttctcttg gtgagaacat tctaattttt attatgagta  30960
ttggcatggg atttgccttt ggattagttg gatttcttat tgacggagtt gtgttaggat  31020
ttatagggaa tacaggtgga ttcacagacc aatggcagga cctaagatat acccaagctt  31080
ttgcatctat cgcatccttt tgtactgtag tctattttta ctatgacttt ataaaccata  31140
acaagaaaaa taaaaaggtt tacgcttctc aaatgattag ttataatgaa ctcctagcta  31200
gacgtgaaaa tgaaacaata gaaaacttta ttaaggaatg tagaaaatga gtaagattat  31260
tgaaattaaa gtaccagagt ttaatgatgc caaatccgct tcagatgcaa tttataaact  31320
tctgaatcaa gctgaacgta tcgaagaaga agcaacaaag atcgcagacc aatatgccgt  31380
atcattttct gtaggtgatt atggtagtgg tcgtacttat tatcctaagg gtgaaattgt  31440
atcccagtgg atgaaagatg aaattgaaaa taatggtggt gatgttaaac gtgaaggtaa  31500
tggttacgtt attactgaag gtgcttgggt ttcgtcttct gcgatgtgct aaggaatcat  31560
tatgtctaaa gaacaaaccg aactggctga agccgtagca aaaatctatg cagctattga  31620
ggctgccaaa gaaattgctg ataaacaaaa cacaacattc gacttgtatc cagcttatgg  31680
tatgggtgga acatatcatt cacccggaca gcttaaagcc gatcttgaac gttgtacaaa  31740
```

aaacggctat gctgaatggg ccgacgttta ccaatatgac tacaacctga gcctcgaaac 31800
tggtggttgg attgcatctt ctcacacttg ttaaggaaac catatgtctc gtgaattaga 31860
ttgtgctata cgtacggcag tagctgccct agaaaacctg ttccaaattg caacagaaga 31920
acgcgaagaa gttacattgt ggattgaaga taacgcaggt ctgaatctcc aggacgcgat 31980
ctcattatcc cacaatagta tcactgttca aggctgggta tcgtctagtt attcttgcta 32040
aaacagttta caacaagata gggctatgtt atagtagtcc tatcaaatta aatggagtcc 32100
acaatgattt attatgaaag tattggaacc aaagtggttg ctaaaaccat tactcgtgaa 32160
aagtttgcaa agatattcga tatgcgttat aaaaaatctg aacacaaagg catccgcttc 32220
gaagatgcac actgtacaat ttgcccttat aatgaagaca taaatggtac aatcgttcca 32280
ttggtagagg cttcacacga tgacctctgg gatgaatata atatcgcatg tcgtgaaatt 32340
taagttaatg aattaatctg aggaaaatat tatgatgtta gttattggtt ctcgtgcact 32400
tcactatcat ggccttattg attctaacgc tatcaaaaat agtgattggg actttattgc 32460
ggaccaatgt tcttggaatg cattcaaaaa tcaaatgatg ggtgtatatg ttcaccaaga 32520
taaccctgat gtccaagttt tcaaatgctt ccacaacgga cgcgaaactc attttgaagc 32580
atatattgtt ccggcaatca ctaatgtccg tgaattagta ggtgaactca ctcctgaaga 32640
tttcacgtct tcttatgacc ttttaaaata cgccaagaaa aatttgacta aagaccgttt 32700
gaacgggttt tactgggcaa ctcctgagat atgtcttgca attaagatgt ctcatcgttt 32760
caagaaaaat aatccattct ttttaaagac tatgaaccat attcagtatc ttcgtggtaa 32820
aggtgttaca ctgaacgatg aacttactga aattatgctg aaacgccaga aagaaacctt 32880
gaactatgct cacccggttc ttgacacttc taaaagtgcg ttctttaaag atgacatcta 32940
tacatatgac catgatacta ttcatgaagc cattgcacta acagaccgcc cagcgtatac 33000
attttatatg aaagatggtt ctgaagtcat gacctcacgc gagaagttcg aatcattacc 33060
ggaaatggtc aaattggccg gtgtatatga agaatcatgt gtactagcgt tagaacgttc 33120
tcagattcct aataactttg aaattaaccc tgaagccagt ttcatgatgg cattagaaaa 33180
agtctgcaca agcatcacct ccggttggtt ccgtgaatac gcctgggaaa actacagcaa 33240
agttgtaagt atgtaccaaa gcttaggaca cgacgattac gtaaaacgtt tcaaacaaaa 33300
tttccatatg gtaaaacctt tcaaataact tcacaaaaac tgtttacaca attatagggc 33360
tatgttatag tagtcctatt aaaacatgag gagaatatta tgaaattagg cgaaaccaac 33420
cgaattggtc tttttacaat atttgcatca ctttttttacg cagctctttc tgttgcagta 33480
ttacaaaagg cttacagtat ggatggtgtt cctggttgta tatttttatc gccgttttta 33540
ttattcgtcg gagctttggt attatatgcc acaactggtt tagaccataa tgtctgggtc 33600
agttataaac gtaaattgtc cgaagaagaa cacgcagaag ctcgtaaaaa agctattgaa 33660
tctaccaatc tagaaaattt cattaaagaa tgtcgaggaa aataatatga atagttctaa 33720
agtgtttaat agtcaagctc gtgcagtagg tggttttgct catgcgatta aaaatgacca 33780
gattaaaaac gagcctatgt tcttcaactg tagtttagaa tttgcttata ataacggcgg 33840
tcctattact cgcagcttca tcatgaactt gccagatgat tggaacactg accaggttgt 33900
atttgattca cgagtccaca tgctgatgcc tggttggtat cctgctattc ctggatatca 33960
ccatgatgac gtaccacgcc ctgatattcc agttggtcaa cactttatta ctgcaggaca 34020
acctgattat gacaatcctc gctatttgtc tgaacatatt cttggtcttg ttaacgctga 34080

```
cgtgtgtcct actcattttg caacaggaac tgcagagttc agtcagattc ctgatggcga  34140
acttatctat cgtcagtggc acaaagaagt cctcgaaaaa attgaaaaag gtgaactaga  34200
gaaatgggaa gctccagatc gtactcttct tcagtttgat tggcaaacat ggcacactgg  34260
ttctcgtgca attagtaatg gatggcgttg gttcggacgt gtatctcgta atacagatcg  34320
agttaaaaag attaccaatg aaattcgtgt caacgcccaa gtttatctgg aattccctat  34380
ggaaggctgg taatgattaa caaaacatat tggtctaata tagacgacgg caatgaaggt  34440
atttcatact attcggtaga ttggacagga tgtccatcct acttagtgaa aaatatttgc  34500
caagaattta aaatcgacca gccagcaggt attatcgtga acagatacat taatggatat  34560
caacctatcg atgaagtaat acgaacaact caagctgagc ttgaaaagtt tttcaataag  34620
tgccaatgga tagcaggatg gattatattt gtaccgtcta tatggttttt cagtactaag  34680
gtgagttctt tcggttttgt tgatattatt gctatcttat tagcatctag tatcataagt  34740
gttgttggtg gcatcattgg cggcggtacc gccgccatca ttattaatct tgttaaaagt  34800
agtttacagg aacgtaaaga caagataaag gccaagaata atgaagttga acgttttatt  34860
accgaatgca ggaatttgag atgagtatag caatttacat taaatcagaa tcatgtgata  34920
gttatctgta cacatacgat aaagatgtgt cagaagaaaa aatcaaagac gaccttaata  34980
tggaccttga tatgttctgt cctattgcag attacaaact tgcggtctct aatagtgaaa  35040
gtccatctaa agaaacgcgc attgaagaat ttatgtccga attaatggct aaatcatggg  35100
accgagatga tgagtaagaa aaataaagtg aaagaactat cagccggtat tattttcctt  35160
accgaagata aagaattatt catggggcgt gtaactggtt ctcgtcctaa aggttcttta  35220
tctcatcggt gggatattcc taaaggtcgt gtcgagcccg gtgaatctcc tatcgaagcc  35280
gctattcgtg aatgcgaaga agaaactggg tttacacaat atgaccctgc cttcctgaaa  35340
gacctaggtg aacatcatta ctcagacaat aagaatattc atctgttcct atataccatc  35400
cctgtagagc acgagcaatt cagaaacagt gtttgtaatt cctatcatac attcccagac  35460
ggacgacaga ttcctgaatt tgatgcattc gctttaatta aaccttctca gtgggaatat  35520
gtaatgggca aatcattata taaggtgctc actaccatcc tataagtaat aaatacctcc  35580
tataaacgtg ggaggtatta tgaatatatt tgaaatgctt cgtaatgacg aaggtcttag  35640
actgtcttta tacaaagaca ctgaaggctt ttggacgatt ggcataggtc atttagtaac  35700
aaagaacccg tctttagctg tagctaaagc tgaacttgac agaatgatcg ggcgtaaatg  35760
caacggtaca attacccttg atgaggctga aaagttattt aatgaagacg ttgataaagc  35820
tgttcgcgga atcttgggta atgctaaact taaaccggta tatgattctt tagatgcggt  35880
tcgtcgatgt gcattggtca atatggtctt ccaaatgggt gtagcaggcg tcgctggttt  35940
tactaattct cttcatatgc ttcaacagaa acgttgggat gaagcggcag taaatctagc  36000
acaatctaaa tggtatcgtc agacacctaa tcgcgcgaaa cgcgtaatct caacatttaa  36060
aacaggaact tggaaagcgt atatatgaaa acatatagtg aatttttatc agaatctatt  36120
cttaacgaag ctactgacac atttgcaact aagctaggtg cagctttggt tgaagccgaa  36180
agtctattag cacgtatttc tgaacttgct agtaagatag atactcgcaa atttgaacgt  36240
accagtgata tcgttaagct tgaagccttg ttgcgtatgt gcgataaacc ggaagaaatc  36300
gctaagaacg gctcgctgat gaaacaacgt cttgaaaaat atatttcagg cgcttcagaa  36360
aaatagtgtt tacttcctcc aagggttttg atactataca ttcatcaact acttggagga  36420
aattatgact cgtatcaatt taacacttgt ttctgaactg accgaccaac atcttatggc  36480
```

```
tgagtatcgt gaattaccac gcgtatttgg tgcagtccgt aaacatgttc aaaatggtaa  36540
acgtgtaaag gattttaaaa tctctccaac atttatctta ggcacaggtc atgtaacatt  36600
cttttacgac aaactcgaat ttttacgttt acgtcaaatc aagctaatcg ccgaatgctt  36660
gaaacgtggt ttcaaaatca aggacacgac tgtccaagat atttccgaca tccctgccga  36720
atttcgtaat aattatgtcc cgtccgaagt gtccattgca ataagtcaag cacgcttaga  36780
tgaaaaaatt gctcagcgcc cgacttggta caaatactat ggtaaatcaa tttactaagg  36840
aaaaatgaaa atgtatcaag aatttatcaa tgaagcagat gccaaagacc ctaaatttaa  36900
agttaaagct ttcattggtg atgcggaaga ctttggctca ttaaaacgta atgagtattc  36960
tttcttaggt ggcgatggta aagaaatcaa cacctatgca aaacgtagtg aaattgctta  37020
tgttgtagca agccctaaag tagatgttga cgatattgga tacgatttta acaacttcgg  37080
aattatttct ggcagtaaag cttaaattgt ttacgcttaa gtattaatat ggtataatta  37140
ctctatcaaa acaaacaagg aaacaaaaat gaaaacatat caagagttta tcactgaagt  37200
tacattatcc gcggaacaga aagctgctat cgaagaaggt aaaaatccca aagtaacata  37260
taaagtaaat agtaaaggcg tttttgatgg cttggttcaa gaccctgaat tgaaaaaagc  37320
tctttctaaa actaatgcgt actttgctcc taaatttaac acagccggtg tacttattgg  37380
attggatgta ttcaactcta aaggtgttct atctaatgcc tttggttatg ccgctaacaa  37440
aattaccaaa gctgcatggg aatccaatac caaacaagct caaaagccta gagtataatt  37500
cttgcctaat aaagggaaac gcaacctctc ctcatgaacg tcgagtcctc tgagtgatgt  37560
acctttttcca acctgtaata aggtcgagcg caatgcggta atgggtttac atagcgagtc  37620
gaaggacata acatgtgcca cggaatggcc caaaccttaa gagaaataat atgagaacat  37680
ttttaactgg accttatcta tccctgatga atgcttttac acaccattct gatgctagag  37740
tagaagaaat ttgtaagaac ggttatatcc cgccatttga agacgtactc aagcagtact  37800
gtacacttcg tttagacggc ggcagacaat caggtaaatc gaccgcagta actaattttg  37860
ctgttaattg gctgtatgac ggtggaacag ttattgttct ttctaatact tcagcttacg  37920
ctaaaatttc tgctggcaac attgaaaaag aattttctcg ttattctagc gacgatattc  37980
gattccgttt atttactgat tctgtccgta gttttattgg caatgaaggt tctaaattcc  38040
gtggattaac actttctcgt attctgtata taattgatga gcctattaaa gctcctgata  38100
tggataagat ttacaatgtc catattaaaa cagtccaaca ctgttgcaaa agcaaatatt  38160
gcatcggcgg taatgctcgt cctcaatttt ttgtgattgg aatgcaatga tgacaactat  38220
tgaagttttt gagtattgtt ataacagccc agtatgcaat aaaagggctc ttgtagaaaa  38280
ttatgagatt tatcatttta aacctaaacg atatcgtttg actaaaggac cgttcgcagg  38340
gcagcaggtt ctttgtactg ctcctaatgc acggttgatg actagtattc cgcatttcaa  38400
aatggaattt attgatgggc catttaaggg attaatcact caaagtctaa tggcgtttaa  38460
ttccgaccca tttttgatta aagaaaaaac ttggataaat ttattttcta attgaggtta  38520
tatgaaagca tatcaaattc ttgaaggcac acataaaggc actatttatt ttgaagacgg  38580
tactcaagcc cggattattg tctctaagac ttttaaagaa gacgctattg tagacccgga  38640
aattttctac ggtttgaatg cccgtgaaat tgaaattgaa catcaaccta aagttaaaat  38700
tgaaggtggt caacacctga acgtaaacgt tctgcgtcgt gaaactctgg aagatgcagt  38760
taagcatccg gaaaaatatc cgcagctgac catccgtgta tcaggttatg cagttcgctt  38820
```

-continued

```
taactctctg actccagaac agcagcgcga cgttattgct cgtaccttta ctgagagtct  38880
ataatggcta aattgattat agaagggtct gaagatgttt taaaatgttt tgccgcctgg  38940
tttagttgct caggcgagca atcatttatt gaagcattta gaatgggtga tattactgga  39000
aactatccga caactgatat cactgtacgt ggatatggta ttaatgagcc tatccaattg  39060
gtcgaatatg accttgccac cgatgaggaa attccttatg tcgattgaag acatcaaagg  39120
ctacaaaccg cataccgatg ataaaatcgg taaagtgaac gctattaaag atgccgaagt  39180
tcgtttagga cttattctag acgccctggc agaagaagca ttatcagcaa atactcctga  39240
agctctgact gctttgtccc aattgaactg tgctaaagaa cgcctaaagg aagctagtat  39300
gtgggcttgt cgtgcggtat ttcaaccaga ggaaaaatac taatggctca aatcctatca  39360
ggctttggaa ctcattatga agcatctcga cgcataactg aaagcaatcc ttttggcctt  39420
gttccgaagc acaagaaaat tcaaagcctt gatgactttg agaatcgcct atgggccctc  39480
tttaatgagt acaaggcata tctgaaagaa gacgctgacg attgtcttga agaagatgag  39540
attgcgtatt acgaacaacg ccttgaacag ctcaagaact tccaccaggt tcgtgacgaa  39600
gtatctaaag cagttaaaaa gttaattcct ttcaaagagt agtttacttc tcctctagtt  39660
gtgttactat agacctgtca actagaggag aaatcaaaat gactatcaat tcagacgttt  39720
ttatccgccg caataaactc cgtcgaatct ttgaaacgga gttccgcaaa ataaatgccg  39780
gtataaaaga tgctgcaaag tctcttggac taccaggctt tcatatcaag tattctcaac  39840
atctcttaga tcgtgctatc cagagagaaa tagatgagaa ctacgttttt gaattatttc  39900
gtaaagtaaa aaatcatgtt aaagaagttg cagaattttt atcaatgccg gcccgtccag  39960
atgttgatga agattttgtt gaaggtgttg aatatcgccc aggccgttta gaaataactg  40020
acggaaatct ttggttagga cttacagttt gtcgcgaaaa tccagcattc aaaatgaaga  40080
ctcttcaatg cagaatggct attattaaca gtaaacgact accaggaaaa gcttctaaag  40140
cagtgattaa aatctagagg taaacatgag aaaagcacta ctcgctggtc tatttgctct  40200
ttcattatca gcacatagct ccgagcatac ttttagtaat gtccaactcg ataacttgaa  40260
ttatgcttat cagtttgggg aacagttttc taaggacgga aaatttaaaa cgcatgaaaa  40320
tatgcataag aaaggacttg gatacataat ggccgcaata ctatggcagg aatcatctgc  40380
cggtattaat cttaaagata agaaaggtca ccatgcgtat ggaatgttcc aaaattatct  40440
accaacaatg agggcaagaa ttaaccagct tggttataat atgactgatg cccaaattaa  40500
gaaaatgcta tctaagcggt ctaattcagc tagatgggct tatatcgaat tttcttattg  40560
gttaaatata cataatgggg atataagaaa agctatatcc tcatataacg cgggatggaa  40620
gacaagtgct ggaagtaaat atgcttctga agtcctagaa aaggctaatt accttaaatc  40680
aaataaacta ctggaaataa aagaatgacc aaaatgttgg ctttaatagt tggcttggtt  40740
tcatttaacg ctcttgctaa tactacatat actgatgtaa cggagtatac aaacagaaca  40800
gcgtctgatt attgtggtaa aagccaagag tgtaaagtag atttttcaca aaaattgtta  40860
tatgcgtata aagacggaga aaaagatggg gcgtctagta ggttcaaggc gtctacctta  40920
attaaaagat actataaaaa atggcaaata ttagaatgct cggtggcgga acctaaagat  40980
aaggcagcat gcaattctat ggtggaccgt ctagttgact cttatactag aggacttgca  41040
gcaagtgatt aaaaactata tcaagggcga tattgtcgct ctgttttcta aaggtaataa  41100
tattgctcat gggtgtaatt gttttcatac aatgggcgct ggtgtggcag gacaattagc  41160
aaaggcttat ccaaaaattc tggaagccga taaacttcaa accgaattcg gagacgaatc  41220
```

taaactcggg tcttattctg tttatgaaaa atattttaag acccataaag cttattgctt 41280
taatctttat acacagtttg agccgggacc taattttgag tactttgctt taatgaattg 41340
tataatagaa ttaaatgaat tcggaaagaa taagataaca aagcctgtaa tttatatgcc 41400
aagaattggt gcaggtatcg gtggtggaaa ctgggatgtc atcgaagaga ttttagatac 41460
gtattccact aaactagaaa ttgtgattgt tgattgggaa ccattattat gaatatacat 41520
tatccacatc catacgaccc aaagaataag gcagtaatta ttcgtcaatg ggaacgcatt 41580
tgtcgtacta aatgcccaat taatagtcca catgatgtag ataaagacta cattggaaca 41640
ttcgttgaat ataccttat tgataagaaa ggtcgtaaac aacatgtaga agaatactgc 41700
ttaaaggtga catggctatg agtcaaacaa aaattcttac aggtgctaaa tgcgaaaaat 41760
gcgaatggcc tgtagttttt gctttatgca atgacgaaat ggcttgtgat tttgattatt 41820
ggtgttactg ttcgaacaaa ggttgtagca atcataaagg tgaagggttt tactcaggat 41880
tttaccctta cccagatttc gttaaagaag gtgaacctaa atgaaattaa ctaaagaaga 41940
gaaagctaaa ctgttcgaac ttatccatga cctattggat gaacaagcag ccaccaatgc 42000
gtatgatgaa tatgctcctt taacagatga agaatatcaa gcattgttgg aatcatttga 42060
caggaaagaa caagaactca ttgactacgt gaattcacta taaggggctc ttatggctag 42120
tttaattttt acatatgccg ctatgaacgc tggtaagtct gcttcattac ttactgccgc 42180
acataactat aaagaacgtg gcatgggtgt attagttctt aaaccggcta ttgatactcg 42240
cgattcaaaa ggtgaaatag tctctcgtat tggtattcgt caggacgcca atataattac 42300
aaaagacatg gatatctttg aattctataa atgggctgca gcacaaaagg atattcattg 42360
tgtatttgtt gacgaagctc aattcttaac tactgaaaag gtgtatcaac ttagtcgtat 42420
tgttgacgta tacaatgtgc cggtaatggc atatggacta cgaacagatt ttaaaggtaa 42480
tctatttgaa ggttctcaag cattaatggc tattgctgat aagcttgttg aacttaaagg 42540
tgtctgtcat tgtggtaaaa aggccacaat ggtagctaga gtcacggaag acggacttcc 42600
aattacagat ggcagtcaaa ttgaaattgg tgatactgat agatatgtgt cattatgccg 42660
gaagcattgg aatgatttga cagggttgtt ataaatacta atatctaacc aagaggtata 42720
tatgcagcaa ttaaacgaaa gacaacttcg taatcttact gtaacccaat tggatgaaat 42780
ccgaagagaa ttaggacatt ctatttctca tttaaacgag gatatccgtc aaactggttc 42840
taaagctgat tatacacgca agcgcaagct ggaaaaatac ctcacagatg ttaaggccgt 42900
ccaaaggcga aaaataaata ctggccaaaa ttaacaggag gcctatatgg ccttaagagc 42960
gatagctgtc atggcgatgc tggggttttt tgcagcaaca actcctatcg ttggtactgc 43020
gtatactgac ccatatttg ataactttat ggaatcaggg attaaaaacg tatatacttt 43080
gtttgaaatt caaaatgtcg agaattctga aaaattctat aagtatatgg taaagcatta 43140
caaaaatagc ccctgtgatg atgcatttga atgtcatgaa caaggcataa aaactgccag 43200
acaatttgcc gagttcatga aaataaaatt agagcctaca tctatctaat ttactagccc 43260
cttccttatg gttggggctt tttggcatct atcagtttac ttctcctcag gttgtgttat 43320
agtagtcctt acttactaga ggagaacgtt atgtcacgta aagaaaaaat ttctaagtta 43380
atgtttttga ttgaagagta cgctaacgcg gtatccgatt gggaaaatgc tcatggttgc 43440
gaagatggag acatcgacat taacagagct atgaaaaaga tggccgatgc ccacaccgaa 43500
ttgcaaatgt atgttaacga gattatgtga ggatattatg ctttacgatt atactggaaa 43560

```
atctgaagac ggtgtacttg aacttttacc tgaaagcgct gaagatgata tggttgtgat  43620
atattgtgtt ggttgtcaat caatgcatga tgaaattttt aaacgtgaac caagaaactg  43680
ttggcacagg agcatgagat gatttattat cttgaacctt gggcttggtt aacaatggct  43740
gtaggacctg ttttaattgg tttattcttt tcatggttag cgaggaaact gtaatgttat  43800
atgacccaag cggttgttct gaagatggtg tgattgttct ggagcctgag catccagttg  43860
gtgatgtata tcgcaccgtt gaagtatgcg aatgtaattt cgttgaaggt aatactggtg  43920
gaatttccat tgagcaagat gatgatgtta tttacctgga tgcaagccaa gtagaagctc  43980
tttatagcat tttaaaacat aatcggtagt ttacgtcttg gtaggactat gatatagtaa  44040
tcctaccaaa acaaatggag aacaaaatga aacttttgct tatcacttat gttgtagtac  44100
aatacaatta tccgatgttt acttataaca tggtaaacgg catagtgaat cttattgaaa  44160
cgagtatggt aaaatgaccc gtgaacaagc taataaattg atggacctta tccgtgactt  44220
acgtgaagct gattcagatt tgaatgatgt agcttatcat gctgtaaatg ataacggaga  44280
tttttatgaa aatcaggttg atgcttgcca gaatgctttg gtgaattttg ttgaaacttt  44340
aattggtgaa taatatgaaa actgtaattg aaacaaccga gttgtttggt gatttatgta  44400
tcgaaaaacg tggttatgtg tatgttctga cacaagaaga tgatgctgct actattcttc  44460
ctatggaact ggacaagatt ttgaaactca atccaccagg tcatgcatct gtaattaaca  44520
tcggtgaaga cctccaagtt cgtttttatc atggacttta tagtggggtt aatatcgaaa  44580
ctgaagacga atgtttttct attaataatt ggaaacattc gtagctaaag tgaaagaatt  44640
catggaatct gaaacagcca aaaaggccaa acttcaatgg gctaaatgcc gtaatgcttt  44700
tattacaaat caggaccgcc ctgactatac aacagtccta ggcgttaatc cttcttatga  44760
agatggtgat gtcgtagtta ttcgtcaaat tgatgacctt cgtcaacata acattacatt  44820
agacaaagat gaagcagttg ctcttaaagc ttatcttgat tctattatcc cgactttgaa  44880
ataaggaatt attatgatta tcaatgaaaa ctcttggcac tttaaaattt atgccgcgtt  44940
caatagtaca tggaatcgtc cgaaaacgtt gtgtgcttat ttttggaaaa cgttaatccc  45000
ggtattggct gcttcaatta ttggatttgc tattttagca gcagccgtta tcattggcca  45060
ggaaatttta actaaattct ttgtttttaa cagtctatgg acattagttc cagcctcaat  45120
cggcgtaggc attttaatgg tagcagtcat ggctcttatt gatgtcgggt tggtaattgg  45180
tccgtcttgg ttgttagaca aatataacga cagaaaatat tataaagaaa ttgagctcat  45240
tgcacaaaac caagaacgaa ttaaaaatgg acttgagcct attgaacgta agaaatcatt  45300
aataggtgaa taccttaaag ctcgtaaaga aaaaatctgt cctactcttg aatataaggc  45360
taaatgatga aaacaattgt gaaaggctac tttggtagtc acctttatgg aacgtctact  45420
cctgaatctg acgtcgattt taaagaaatt tatgtccctc atgctcgtga tatcttgacc  45480
ggtaacgtta aagaacatat gagcaagaac acgaataaca catcttctaa gaacacaaaa  45540
gacgacgtgg accatgagtt gtatagtctc aaatatttct ttaaactagc ttcggatggt  45600
gaaaccgtcg cattagatat gcttcacact ccaccaagtt tagtagttaa atctgatttg  45660
cctgatgtat ggaagtatat tcaagacaac aggtctcgtt tctatactac taacatgaaa  45720
tcttatttag ggtatgtccg taagcaagct tctaaatatg gtgtcaaggg ttctcgactg  45780
gctgttctta gacaagccct taaacgttct aatgaatggg gacaatactt tgataatggt  45840
gcagtaattc gtttatcaca tatgaagaat gttctgcctg taggtgaatt tgcttcatgg  45900
gttgaaaccg aaaacgagaa aacaggtaag caaacattct ataatctgtt ggaccgtaaa  45960
```

```
ttccaagaca cattaaccaa taaagagttc aatgccatcc ttgttaaact agaagagaac  46020

tatggtgaac gtgctcgtaa ggcagaagct aacgaaggta ttgactggaa agcattgagt  46080

catgcatgtc gtggtggact tcaattattg gaaatttaca aaacaggcga cctggtttac  46140

ccacttcagg atgctccatt tattctcgat gttaagcttg gtaaacatac gtttaaaact  46200

gtacaagaat tcctagaaga tatcgttgac caagttgaac atgcgtcaga acaagctgcc  46260

aagaacggta tgcaacaaaa agtagatatg agtttctggg atgacttcct tgagcaagtc  46320

tacttagaaa accacaattc atactataaa tgataagggc tttcgggccc tttagggggt  46380

caaaatattt ttaaaaagta gtgtacatgc ttttaggata ttgttattat agacctatca  46440

aaacaagagg agaacaaaat gaaaaccaaa atgttagaaa tgattcgtga agctggtgat  46500

aaaggtctta tggttaacac tcgtgatgca gaccaacgtc aagcattcgg tgagctgaaa  46560

gctaaaggtc tagttaaagc atccttggga atcggtaatg cattacgagt taccttaacc  46620

ccagccggta aagcagtgtt ctttcaacct cttaccaaaa aatctcgtcg caaataattg  46680

tttacttttg ctttaaacat gttattatag acctatcgaa acgaaatgag taaattggag  46740

aataaaatgt tcaacgttca aatcaaaaaa ggtatctatc gtaataacga aatctctggt  46800

tcttatgttg ccacaaagac atggttcccg gcaaagctta atcctgaatg ttcccactta  46860

ggtgacggta aaattttcgt tatgattgat ggttctgaac gtggagtatg ggtcttcaaa  46920

tcagacatcg taatggaagg agttgagacg tcgccagttg cagttgttga aagcactgaa  46980

gatatgaaaa ctcgtatcaa caaacgcttt aaagtaatga acatgatgac gaatggcatt  47040

atcgatggca aaattcgttc actcattatt tcaggtgcag ctggtattgg taagacgtat  47100

tctctggata aagcacttaa taatgctaat gataacggtt tcatcaaata caaaagcatt  47160

aatggtaaaa tctctggtat cggcctttac gaacaacttt ggctcaaccg tgatgcagac  47220

agcgttctct taatcgacga cgttgacgta ttctcagata tggacatctt gaaccttctt  47280

aaagccgcat tagataccgg agataaacgc aaagtttgtt ggagcactgc gtcatcttat  47340

ctcgatgata agggtattga taaagaattt gagtttgaag gtactatcgt tttcattaca  47400

aacgttgata tcgataaaga gttagaacgc ggttcgaaac ttgccccaca ccttcaagct  47460

ttagtatctc gttcagtgta tctcgacctt ggagtacact ctaatgaaga gattatggtt  47520

cgagttgaag atgtaatatt atctactgac atgatgcaga aacgtggtct gacagatgca  47580

gaaacgtata aagcattgtc ctggatgaag gctaacgtat ctcgtcttcg caatgtatca  47640

ttacgtacgg ctctttacgt agcagatttt atttcaactg ataaagatgg ttgggaggaa  47700

atctctgaag ttactttact gaaataagct tataggaagt tctgaggtaa caaaagccat  47760

aaagatgaat aatcatatgg cttacctcaa agaaggacac caggaaccta ctgagggcat  47820

agaaatattt aaaaataatg ttgtacaaat caaagaggat atgttatgga ttttatgcaa  47880

aaaattaaag ccgcagtcga actgtatgct catcgtatgg ttagttctac aatgcaatat  47940

agcgaggagg ttcgccagga ctcttccttg aaaggaaaaa ctaaagcctt aattacctta  48000

gaccgtctac aaaagaatgc cctagagttg ttccagtacg acaaggatgc atataagaaa  48060

gaacaggaag agaaacttaa atctgaaaaa ttacagaaaa ttccgaaatc agtttggttc  48120

agtggaaaaa ataccgaaaa aagtttcttt tagttgttta caaggtctat ggttatgtta  48180

ttatagacct atcaactact ggaggtaaaa catgaacgct aaagatattt tcaacctggt  48240

aaattataac gacggtaaat ttaaatctga agcacaaagc aagttcttta atgacgttgc  48300
```

```
ttatggtaat gagattaccg tggacggagg tcagattttc aaatctcgct ggaattggat  48360
tgctatcatc gattcagttg gaattgtgga agtctacaaa aacactaaca aaaaacgtac  48420
attattctgg tctcgtgaaa ctaacgagca atacaaaaag gataaagcat ctcgtttatc  48480
caaagtaacc aaggaagata tcgagtttat caagaaagat atcgagatgt acgaaaattt  48540
aatcgctgaa gaccaggcag tactcgacaa gtttgacgaa attaaagctt ctcgtgaaat  48600
ccctgacttc atgaaagaaa cagtaaatga acgatacgct ctcacttcag aacgtattgc  48660
aaactataca aaacagaaag cagaacgtat tagtactctt cggaaatttg aagaacgttt  48720
aaagacggtt cacgcataaa cgctttaccc aaggacgggt tataatggtt ttgagttcca  48780
attcaatctg aggaaatagt tatgagcatt acatctgatg cggtaaaaca tgaaattaac  48840
ggtttatgtg cttcacagat taaagtgtgg tttaaagacc ataatgatcg cagagcactt  48900
aattatgaac gaattgctat ccaagttcat caattactga ctagtaaatt tgattttcat  48960
atgccgtctg aaatctatac taatctaccg cgagcgctta ttaaagcgtg taaaggttac  49020
ggaaaatcaa tggccgatgg aatcttcagc gcgctgaata aacttaacgt tctgtcgatg  49080
attaactcta acaacatcct gcgtaatcta ggacgtactg atttgttcgg tcgtgaacag  49140
tgtaaaatgc ctttgaaatg gattgttgct catcttaacg agaaccaaac acgttttatg  49200
gccgtatcag cacgcttaca aatgggccta gatcgtcaga tgaactttaa aactcatcca  49260
cgttattcag gttcaacaga cttttataaa tgtgagcttc aaaaggttgc aggtaaaact  49320
gtcttagtag ttcgtgtaac gtttgaagga cgacgtcaag gatattttga cgtaatcggc  49380
tctggactta aacattgtgg atttatcgac gaagttgata tcaagcgaga cagcattgga  49440
taccgtattg gatatgtttg tactcttaaa gaagagattt caggaccagc accaggacta  49500
aaagacgtta gatataaaga cgagctcgtt gaagaaataa aagaagttga atatgatatc  49560
aaccaagaag atgctcttaa agaccttatt gatgaactaa accaagacgt tattccggtt  49620
cagaaatttg aatcaaaaca tgctgagcaa atcaaatact ttgaagcttt gattaacgaa  49680
cttaatgtaa ctattcaaca aactgacgat gaaatctcac gattagcagg cttaaacagt  49740
aaaaataaaa cagaacgagc taatcttatt caggtagtaa aacttcttaa ggaatgatgt  49800
acaaccaagg atggttggag tataatgaaa tctatcttaa caagaggaat ataaaatggc  49860
ttctattaca cgtagagaac ttatcaaaga atttacctcg aacgcatata ccccaggacc  49920
taatcctatc cgtatgcctg taaagactcc tgaagagatt gaggaaatct gttcatatta  49980
tgggattaat tctcgtaagt ttactcaatt tgaatgcgtt actaacacac ccgttaaaga  50040
gttcattaaa aatggtgagt tcagccgttt attggccaaa cagaaacttc gtaatttttg  50100
tatcggcggc tacggacaat attttgctaa acagttcaga aataacctta acaatctgat  50160
ggccattgct tctcgtattc gtcctcaagc aattaacatg aaacatttga aatatactta  50220
cgataagtta gaaatcatgg ttatcagtga gaacgagttc actcttacgt ataaacctaa  50280
gaatgataac gttgctcgtg tattccacca agcgttggaa gttttaggtg ataatatcca  50340
ccagattaaa gcaatttatt ctcgtgagct taatattatc aaccctatca agaataaggg  50400
ccatatcgct atccaggctc gtgtatctgt tggtaaaaag gttcctgcgc catggtggca  50460
caaagactct gaatactatc aaaatcttaa aaaggaaaat gcaacgttcg aagcgtcaat  50520
tactgcaacc ccaattggca atgctgaagt tctaggtgca tattctactt ctccatctat  50580
atacacttca ccgtcgacta aactggaaat ctctaacggt cttcttcctg cagaagatta  50640
ctattataat caaatcaaag ccactgtaga ccaactgtct gttgaacttg acaaagcaca  50700
```

```
agctaagctt cgtgatgctc aacaagtagt taccaagctc cagttgcagt attctaaact  50760
ttttaacgca atgaatgcat taaaatcata aatcagttta caaccaagga tggttggagt  50820
ataatctttc tatcttaaca agaggaaaat attatgacac gttcacatta cgttgattat  50880
tttgcaggtc ttatcgctaa cgttcatgcc caacgtgctt ccggttcatt aggatttgat  50940
gttccacacc gagttgtagt aagtggcatt cttcgagatt ttggtacata cacaggtcaa  51000
gaaaatcata tctgtaaaga tactcagaat gcgtattctc attcattagg gacgctgctt  51060
caatggttca aacgttctcg tttattatct tctactgtag ctcgcgataa cattaaaaac  51120
tttatgaagc cgagctttat taaatctgtg acatctaaaa ctgatttggt tgaatttact  51180
attattaacg atgttaaaaa gactcattta gctgattggt tatctaccat tcctgaaact  51240
aaatttgctg ataaatttgc ttgtgaattc aataaccaag ttaatatgct ttttaaacat  51300
tctcgtaaat tattcactgg cggtgatggt cgtacaaata aagttcatgt taaagattgg  51360
gttactgcag tattcaaacc aaccggtaat ggtaacgcat cattatcaat tgatatccag  51420
gttccttatt actactcacg taatctcggt accatgaaag ctgaagaaat taataagcat  51480
aacaaaaccg ttcgttcatt gtcttataaa cttattacgt tgttagagac tatggatgtt  51540
gttgaaactt tcgacgaatc tgaagataac ggttcaatgt tatacagttc tcgtacccga  51600
attaagctga agaaccctaa tacgtataaa cctaagctta ttaaagaacc taaagcagaa  51660
aaggttgata tcatggctga agaacgtgaa tacctcaaat ctcgtctgaa agaagtcgaa  51720
gcccagattg cagaacaaac taaatcatta aaagctctga atgcaaaagc tgatggttta  51780
cgaaatgcca ttgaggtgtt ataatgaaac tacgtctttt agaggatatt gatatgagca  51840
ctaatcatgg cttggttaag tttattgacg atagttcaaa gattgaattt gttcagcgag  51900
ataaaatcca cggtgaagaa gagttcgttc ctccggcatg gaacgaaata atgaaaatgg  51960
ttgaacgacg tgaaaatgct gccaaatcgg cagcaaaaca tccgtgcccg gaatgtggaa  52020
ctatccaagt ccaactggtt aactggacca ctgataactt gaaattgaaa tgccgtaaat  52080
gcttccacaa atttgagaga acattataat gagatatagc cttcgtttgt ttattgcagc  52140
tttagttttt gccatcattc cattcatttg gaacagtcag aatacttaca tggaaactaa  52200
agtaattcct gtggaggtag tggaattaat ctcaggccaa tctacaggaa aatattctaa  52260
attggaattt attgcagttt ataaagatga acaaggccgt gtttttgaca ggcgtgtatc  52320
gccatcgttt tatacgcttc tgaataaagg tgatacgata gctatagaaa ttcgtgagat  52380
ggatatcaaa caaactacta aagataactt gatttggttc tttggtacag tgttgttggt  52440
ttctatctgt atcacaggtt ttattacatg tattgtattt ggcgttgcat atttaattga  52500
tgaaaggaaa aataatgttt aaagtatatg ggtatgactc tactattcat aaatgcattt  52560
attgcgataa tgcgaaacga ttgctgactg ttaagaaacg gccattcgaa ttcattaatg  52620
ttatgccaga aaaaggtgtg ttcgatgatg agaaaattgc tgaacttctg gttaagcttg  52680
gacgtgaatc acaagtcgga ttgactatgc ctcaagtgtt tgctcctgat ggaagtcaca  52740
ttggtggatt tgatcaactg cgagaatatt ttaaatgaca tattcattaa atcttaaaga  52800
tttccaagat gtatacgaag tttgtgccaa tgaacttggt cctgatgctc caactattat  52860
tgaagtttta aatgtgctcc cttcatcatt agcttacgaa gccaaatcat ggggttggaa  52920
cgacactgtc gttcgtgatg acctttacgt cctgatgaac gatatgatgg ttaaaaaggc  52980
agaaccggtt gcaccaatgg ttaccattac cgttgaagaa tataatcgcc tgcaagccat  53040
```

tgaagagctt ctgtggaaca ttgaatgtga cctgccgtca gggctagaat cctggattga 53100
ttatgaagag ctcaataaac tccggggtta aaccgtggta ttcggctcga tgggagacag 53160
tcgagccaga cgtcgaaaca gtttacaatg acgaagaaac gtgttatgat gaaccttcaa 53220
tgaatgaatt aattgatatg gaaatgggaa gagattatta tgcaagttaa attattgtac 53280
cgtttattaa aaaatggcaa gcatgattgg tatttgctta ttaaaaccga tccgaatttt 53340
ttctctggac aaccatttac agttcgtcct actaaacgtc agcttcgcaa agctaaacgt 53400
tctcatcgta acttttatag aggatattga tatgaatatt tctgaaactc gcggtaaatg 53460
gttcaagatt gttaaagaag acgaagaact acaagtcaag tttcctgaat taaagaaagg 53520
aacaatcatc aaggtaattg gtatttcaac aacggctggc tggggcagtg gcatcgttga 53580
agtgatgttg actaccggtg agaaactttg catccacgac cgtgatatcg gtttttggtg 53640
tttctgggaa tcccattcaa tagatgaact cgaagaaatt gaccaagtag tttgtgatgg 53700
tgaacttggc gaattcgaag gtgaacgtat ttcttatgct ttagctaaat tagccgccca 53760
agaaaataat gacggttatg aaggtaatct gatgcaagcc gcagcggaat acattgaata 53820
tttagaaaga cgtttaagtt aagggcttat tatgaaaact gcattatttt ttggcgaaag 53880
aacaaacggc caaaaatctt ggaaatttgt tataattggt gctccaaaca atccgaacat 53940
gaggacttca atcatttcgg taacacgtcc tactaaaaga atgattcgac agtataagcg 54000
ttttcatcga gacttttata acgtttacta aattataaat acccttatct atttaaggta 54060
agggtttatc atgttattat caggcgcaaa atataaagaa gaaaaacaaa aattttatga 54120
tgcacagaac ggtaagtgtc ctatttgcca ccgtgaatta gaccctgatg ttcaaggtaa 54180
ccatcttgac cacgaccacg aattaaacgg gccaaaagcc ggtagagttc gtggattact 54240
ctgtaatctg tgcaacgcag cagaaggtca aatgaagcat aagttcaacc gttccggttt 54300
gaaaggtcaa aacgttgact acttagaatg gcttgaagct cttcttactt atttgaaaca 54360
agattattct gataataata tccatcctaa ttttgttcca gacaaaacta aagagttctc 54420
aagactaggt aaagaggaaa tgatggctga gatgcttcaa agaggatttg aatataatga 54480
atctgatact aaaacacaat taatagtttc attcaaaaag cagcttagaa agagtttaaa 54540
atgaaaattg aaaaagaaat tgaaggatta atttataaaa ctaataaaga tcttttgaac 54600
gagaatgcta ataaagattc tcgtgttttt ccaactcaac gggaccttat ggctggtatt 54660
gtgtctaagc acattgccaa aaatatggtc ccgtctttta ttatgaatgc gcatgaaagc 54720
ggaatcattc acatgcatga tattgattat tctcctgctc ttccgtttac taattgctgt 54780
ttagtcgatt taaaggggat gcttgagaac ggatttaaat taggcaatgc tcaaattgaa 54840
actcctaaat caatcggcgt tgctactgca attatggcac aaattactgc acaggttgct 54900
tcccatcaat atggcggaac gacttttgcg aatgtcgata aagtactttc tccttatgtt 54960
aaacgcacct atgcaaaaca tattgaggat gcagaaaaat ggcaaatcgc tgatgcgttg 55020
aattatgccc aatctaaaac agaaaaagat gtatacgacg cgtttcaggc gtatgagtta 55080
atttaattca ggctcatgta aaaccggtct aaacggggaa cctctctagt agacaatccc 55140
gtgctaaatg ttcttgtgaa ctaaatgcct aacgactaac cgtgatgaat gtagcggtgt 55200
agaatagaag ctaatgctat tcgaaacggc cggcatcgaa agatgaagat atagtctaat 55260
ctgcatggcg acatgcagca gtcatcttgt ataaataaga ttatcttatg aatacgaggt 55320
gaaacaatga aatggataaa aagacgttgt actaaaataa aagataaaga cgcatttaca 55380
tacttagtta agttttctaa tggcgacatt tatatcggtt ataaaaaatt tagaacaatt 55440

```
aaaaacaagc ccacaaactg gaaaacttac acaacgtcat ctaagtatat aaatgaacgc  55500
ttaaaaactg atacacctac taaatggata attttaaaaa catttgatag ttataaagat  55560
gcattaaaac atgaagaaga ggtcatacgt aaatattttt atagcaaaaa atgtttaaat  55620
aaatccatag gcggtaaaaa gttttataag catccggata ctgaagaaca tattcaaaaa  55680
ttaagagatg ctcataaggg taaagtgtta tccgaatctc ataaaaacaa tataaaatct  55740
tctgtagctg aatattatgc taaaaacgga agatctaagg aacatgtgca aaataatatc  55800
aatagtcgaa aaagtaaaaa acaagtatcg ataaagctta aaaataaaac ttttagaagt  55860
tttaaaaaag cagcggaata tttaaattgc actgaaagtg aagtcgaaac tcatcctctt  55920
gttttgagta ttaagactgc tattcataaa gttcctgaat atgtggttgt tgacggtatt  55980
aagtatacgt cttatataga agcagctaaa gcgctaaatt ttcatcctag cactataaaa  56040
gaacgttgca tatctatgga ctatccaaat tttgttgttt catataaacg ggcatgaatt  56100
tgcgactcat gctgaatata atgatgaagt aaatacactt ttcagctcta atggacaaac  56160
gccttttgtg acaatttcat ttggtactgg aactgactgg actgaacgaa ttattcagaa  56220
ggcaattctt aaaaaccgca ttaaaggtct tggacgtgat ggaataactc ctattttccc  56280
taaacttgtt atgttcgttg aagaaggtgt taatctttat aaagatgatc cgaactatga  56340
tattaaacaa cttgcgttag aatgtgcaag caaaagaatg tatcctgaca ttatttcggt  56400
taagaataat aaagctatta ccggttcttc agttccagtt tctccaatgg gttgccgtag  56460
tttcttgagc gtatggaaag attcgactgg aaatgaaatt cttgatggac gtaataatct  56520
cggtgttgta acactgaatc ttcctcgtat tgcattagat tcttatattg gaacacagtt  56580
caatgaacag aaatttattg aactgttcaa tgaacgaatg gatttgtgtt ttgaagcttt  56640
gatgtgtaga attagttcct taaaaggagt taaagcgact gttgctccta ttctttacca  56700
agaaggtgca tttggggttc gtcttaaacc tgatgatgat ataattgagc tatttaaaaa  56760
cggtagaagt tcagtgtccc taggatacat cggtattcac gaattgaata ttcttgtcgg  56820
tcgtgatatt ggacaggaaa ttttaactaa aatgaatgct cgtcttaagc agtggactga  56880
aagaactggt tttgctttta gcttgtattc tactcccgct gaaaaccttt gttatcgctt  56940
ctgtaaactt gataccgaaa aatatggaag tgtaaaggat gttactgata aaggctggta  57000
cactaatagt ttccatgttt cagtagaaga aaatatcact ccgtttgaaa agatttctcg  57060
cgaagcacca tatcatttca ttgcgacagg cggtcacatt tcttatgttg aacttcctga  57120
tatgaaaaat aacttaaaag gacttgaggc cgtctgggat tatgccgcgc aacatttaga  57180
ttattttggt gttaacatgc cagtagataa atgttttacg tgtggaagta cccatgaaat  57240
gactcctact gaaaccggat ttgtttgttc agtttgtgga gaaactgatc ctaaaaagat  57300
gaacacaata agaagaacat gcggatatct tggaactcct agcgttgttc catggaattt  57360
aggtaaaatg aaagaaatgg taaaacgagt aaaacatgca taggtattat ataatttata  57420
aaataacaaa tataattaat tcaaaggaat atatcggtgc gcatagcacc gataacataa  57480
atgacggtta tatggggtca ggaacattga ttcgtgccgc tttattaaaa tatggtagaa  57540
aaaattttaa taaagaaatt ttacatgttt ttgataatga aaaacaaatg tatgataaag  57600
aagctgaact tgtaaccgaa gagtattgtc taaaagaaaa tacatataat attaaacctg  57660
gtggaaaagg tggaactgcc tatgaacaga cacttgaaca tcgccgcaaa aatagtttag  57720
caaataaagg taaaaagaga acagaagaaa ctaaaatagc tatttcacgt gctttaaaga  57780
```

```
aatataaacg tacgccagag catcaagcaa atttaaataa agccgtaagc atagctatga  57840
agcgaaaaga tgttagaagt aaattagctg gagagcggtc tgagaaagat aaattatcta  57900
tatcaaacgg tgttaaaaaa tattacaatt ctttgagtga agaagaacgc gaacttcatc  57960
gcaagcgaat tattgaaggt aaaaagaatt ctcccatgtc attggaatct agacaaaagc  58020
tttcaaaagc tttaaaagga cttcaagttg gttcaaaaaa tccaatgtat ggaaaaattt  58080
ctccaactag caaaaccgtt tcagttgacg gtattaaata tgattcaatt aaaaagtgct  58140
caaatgccat aaaagtttct agacatctta tactaaaacg ctgtaattct actgatgaag  58200
cttggaaaaa ttggatatta ttatgaatta tgatagattt tatccttgcg attttgtgaa  58260
tggccctgga tgcagggtcg ttcttttcgt tacaggttgt ttgcataaat gtgaagggtg  58320
ttataataaa tcaacatgga atgctagaaa tggtattcca ttcaccggtg aaacactaga  58380
acaattaatt gaatgtttga ataatgatta tatagaagga ttaactataa ctggaggaga  58440
ccctctctat cctgataacc gagatgttgt tcattgcatt gctcaaacag taaaaaatct  58500
ttatcctaat aaaagcattt ggttgtggac aggatataag tttgaagata ttaaacaact  58560
agaaatgctt aaatatgttg atgttattat tgatgggaag tatgagaaaa atcttccgac  58620
caaaaaactg tggcgaggat cagataatca gcgactttgg tcaaataccg atggggtgtg  58680
gaaacatgat taaattgaat tacattatgg atactataaa tgatatgatt tttcattttg  58740
gtccagaatt ttattcccaa tatagcttag tgtttatcaa tgtttggtta atcaattaag  58800
ggtaaatatg tataaatttc gtaaaggttt agctgatttt cttacaactg taacgttctt  58860
tttgtttatg gcagttggag ctattattct tattcctttt actgttgtat tttcgtgat   58920
tagtttaatt tctcctgaaa agggtttatc ctccagcgaa ttcaatgaac gtttggacaa  58980
aattactaat aaactgaatt ctgttcttga taaaaaggct taattatgat tagttttgag  59040
cggtatgtag tagagagttg gaatggtttt gatatgttcg gtaatgacta ttatttctat  59100
gaatgtagtc taaatcctag tttttgggct ggacgtgaac aagacctcga agaaatcaac  59160
gctcgtgccg atttgttagg tgaactgcct actacttatt tcacctttga tgaatccggc  59220
ttcgttatcc aggtttattt tcctgaagaa aactctggtg aggattctgt taacccgcca  59280
tactgggctt accaaggaat tatttctcgt ggaacaaaac tcgaacttaa agaacaagat  59340
tgaaatctat ggcatccctg aagaagttgg acgttgtccg ggatgttata ctgttacaaa  59400
acttttaaag gagctcaatg ctccttatac attttataaa gtcctcacta ataatggtaa  59460
gattgaatat gaccgtcctt taatcgtatc tcttgctaaa cgtgcaggat tcacttcact  59520
caatattcgt tatcctgtca tatttttaaa tgataagaaa caaaagaata ttgcagagtt  59580
taaaaagtcc ttgatttcat taggatacga ctctgatatc atagaagatt gaccaggtgc  59640
cgcctggtct tctttatctc atttctaata taatccattg gaatcttcac ttcactatct  59700
ccttgtgccc tctcaaatcg aaaatatttt cataaaacag tttacatcct caatagatgt  59760
gttaagatta aaccatctac tatagaggaa aacaaaatga ttagtctgaa ttcgaagaaa  59820
gttgttctaa ctcttaatgt aaacaacgaa cgtctgatat tcattaccat ttccgatttg  59880
aacgttgaaa ttgctaatgg cgtccgtact tatcaaacgt ctaaaacaca ttgggactat  59940
atcccaacgt tgacttttat tcagcgttta gaatcaatcg gtcttaaaga cctttcaaca  60000
agtgaagtga attttatcaa acgcattgta tcaatcaacc tctgaggtac ttatgggtaa  60060
aacgtatcgt cgtaaagatt tgaaagttcg tgattacgac tattttggta aacgtaaagc  60120
tcctgacggt gttagccaca aagacatggt tgaaaacatt ttccgctcag ataaatggaa  60180
```

```
acgtatgaaa ggcgttgatt ctgaagtcaa gaatgaaatg aatcgacaac tccgcaaaga  60240
agttcgtaag ttgaaaaaag atgtttacag taaagaagat tatgattata atacttctca  60300
tactgaagcc aaacgtaaag ctaatgaatg ttatcgttac agttgaggaa attatgaata  60360
tcaaacgaat gctttttaag cagggattat atactttaaa tgttaatcca aagggtgata  60420
caactaaatg gtctgtaaac gactggatta agttcatcga tgaaaatggg gcgtggaaca  60480
caaaatgaat cctgaaaata ttgtgtcatg gcaacttcgt gaagaacgtg ccgaattctt  60540
tgccaacatg aaactcaacg gtgttgagga tgaagacttt ttacgttggt tctggattta  60600
caaatacaaa gaatgccaac atgctgtgct attgacttgc gcagttatgt acgaaggctg  60660
gaaaggcgct aaaaagttcg gttaatagtt tacaacgata ggaagataac atgtcttcct  60720
atcaacttga ggagaatatc atggaacaag aattagacat tattacatcg aaaaaacgcc  60780
ttgaagtcgt agtgaatggc tcaactatta agtttgtata tgacacttta actgatgcta  60840
ttaccgttag ttgtggtgga aatgctttta gtctagattc tactgaaaac aaatacccgt  60900
tctataaagg tatctttgat atggatgttg atatcagtgt tcgtcaagca aactatttac  60960
attatcttat cacgaaataa tgcacaaact cttgagagca gagtataatg ctctcattgg  61020
ataataaaat aaccgaggaa aataatatgt ctactaaaat caaaaacgta gttaattctt  61080
tcgctttcga taaagttgtt gctcttctgg aatccggcaa tattgttact cctcaagttc  61140
ttgacgcgtg ggaattccgt ctttatgaaa tcatgcaaaa acacgaccag aaaattggac  61200
gcaattctat tcgtgaaatt ctagtacaat atattctttc tgaatttgac gttgctgcat  61260
ttggtgttga atctaaagct tatcagaaac atgaaatctc tgaaaagact atccgtcgta  61320
tgaaaaatca acgtaagaaa aaattcgttg acctgaaaat tgttaaggcg gtaaaatgag  61380
cgtattaaca gaagctttga ttaatgacct gcgtctagct ggttacgaag ttggtacaaa  61440
tagcctaggt ctttctcaga ttgaagggct tggatttatc ctagaatatg aattcaaaca  61500
atggtggtta tatgctacgg ttgacgatgc gttgaatatc gatttcgtcg accaatttga  61560
ttcgttggat gctgctcttg aagcagcaaa ggaactagaa tgaaattaac tcgaatcagt  61620
ataactgaag aaaagctggg cgaattttat gttgacgaat acatgaaagt cacgtatttt  61680
ccattcgtta aaggtgttgg tttttgggaa actcatgtat ctcaattaaa tgaaggcgac  61740
tataacgaaa cacatgagaa ctttttagat tttctttata atgccggtct tactgagctt  61800
tatatcgata tccatgagtt caaacgttta atggaaaaag tgtttcaggc ttattgtttg  61860
ctccgatagt atctcgtgct ttaagatagg tctctaaata ttatgatata atagacctat  61920
gaattgagct aagaggtact tatgactgaa caaaaaccta aaaataacta tgtgaataat  61980
aaagagcttc tcgccgctat aatcgagtgg aaaaaggagc tcttaaataa taaagaccca  62040
aacaaaatta ttcgtcagaa tgataccatc ggtttagcaa ttatgcttat cgccgaaggc  62100
ctgtccaaac gtttcaactt ttcaggatat acccagtctt ggaagcagga gatgattgca  62160
gatgggattg aagcctctat taagggactt cataatttcg acgaaactaa gtacaataac  62220
ccacatgcat acataactcg agcttgtttt aatgctttcg tccaacgtat caaaaaagaa  62280
cgtaaggaag ttgcaaagaa atatagttac ttcgttcata atgtctacga cagtcatgac  62340
gatgatatgg tagcgttggt agatgaaacg tttattcaag acatctacga taaaatgacg  62400
cattatgaag aatccgctta taaagctcct ggggctgaaa agaaggaagt tgttagcgat  62460
tcgcctagtt tggatttttt atatgaggat gacaattgac atctctaact acttagaaga  62520
```

-continued

```
acctttttgac gaagcaatcc cttatttggt aaaactgttg ggtcgtgaat ttaaaattaa  62580
ttttgacata gaccctttga acccacatga cgtgtcattt tcgataaatg ggactccggt  62640
tgagtatgag ttctgtattg aagaggatgg acgtttttat tttaatttaa tgagataata  62700
tgactaccga gattattgaa aataaagaag cagaagatgc agtagctaaa atgctacaag  62760
aaatccaaaa gaaaaatgaa gctgaagcac gtaaaaaatc cgaaaagatt cttaaaaaga  62820
atcgttttga actaaaccgt ctttatgcac atgctcaaga agcagcaatt caaaacaact  62880
tcgaagctta tgaatatgct attaagaaat ctcgggatat tctacgacaa ccatataatg  62940
acaagttaat taaaatccag tggattacta ctcgtcaggc tattgaggac atcattaatg  63000
gcgctagttc aaacaaagtt taaacgtctg aagctgaacg cagggttcac cattaaattg  63060
ggtggtcctc tttgtgttaa aatttctgaa aaggaatatc acgacggttc tattacagaa  63120
atttgtccgc ctattgtaaa ggcagaccaa aaacaactcg tgtgggtcga ttcatttcaa  63180
gttaagaaat ggtggaaacg atgagagaaa tcgatttagg tattttctga gaggtgatta  63240
tgcatgacga acatcccgac ttctgaaaat tttgataaaa tccgtaaagg caaagcagaa  63300
agaatgagac gttttaaaga gtcttatgat aaagctaaag ccgaaggaac tattacgtac  63360
aagccaattc gatttaaaag ttcaaatgag cctctgtacg gtgtactatg tggataggaa  63420
ctcttcggag ttcctttttt gctttataaa cggatgatag aatgaattaa ctaatgagga  63480
aataatatga aaattttgca cttaggcgac ttccatatcg gagtcaaaca agatgaccca  63540
tgggttcaag atattcaacg tgatggtatt cgacaagcaa ttgaatactc taagaatcac  63600
gggattaaaa cttggattca gtacggtgat tggtttgacg tccgtaaagc aataacacat  63660
cgtacaatgg aattcaatcg tgaaatcgtt gatatgattt ctaaagcagg cattcacgtt  63720
catgtcacga taggaaacca tgacatggcg tttaagaata caataacacc taacactgtt  63780
tctgaattgt taactcaatt tgaaaacttt actatttacg agcatccgac tactgtagat  63840
tttgacggat gtctgattga tatcgttcca tggatgtgtg aagaaaatac aggtgaaatc  63900
ttagagcaca tcaagacttc ttctgctgcg tattgtgttg ggcactggga actgaacggc  63960
ttttatttct ataaaggaat gaagtctcat gggcttgaac ctgatttctt aaagacctat  64020
aaacaagtct ggtccggcca cttccacaca atctctgaag ctgctaacgt caaatatatt  64080
gggacaccat ggaccccttac tgcaggtgat gagaatgacc ctcgaggatt ctgggtattt  64140
gacactgatg ttgaacgtat ggaatttatt cctaatgaaa caacatggca tcgacgaatc  64200
acttatccat ttaaaggcaa aatcaattat tctgattata ctaatctagc cgtacgtgtt  64260
atagtatcag aaattgattc agggttgact aagtttgaat ctgaacttga aaaagtagtt  64320
cactctcttc gtatggtttc taaagttgat aacagtgttg aatctgatga cgaccaggaa  64380
atcgagatta aatcacttca agatatcatt aaagaatata ttgacgcgat tccagatatc  64440
tcagacgaag acagagaagc gctggtcaaa tattccaacg aactttatat tgaggcaaca  64500
caatgacttt agatgaattt aacaatgctg gactcaggct tgaagttgaa atggacgtta  64560
aagatgatga tggattcgag aacactatca agtattggat tgagccatta cgcgttgaag  64620
gcaatgaagt taaagcagtt catgtctgca ccgactgggc tattgaattt agctttaata  64680
taatggacaa cgatactcct ggctctattc ttaaaatggc tgaagcgtgt attgaggatg  64740
cgtataatga cgaagactga ctatgaaatc catcgtcatg aatttagtat tggcgacggt  64800
tatattggta tcgttgaatg gactgagaat tacgaggaat caactcctcg tttctttgga  64860
acaatgtatg ttacctgtga gtacgcaccg ggtgttgtta tgtatgcaga actagatgaa  64920
```

```
tattttgctg atagagatga catgttaaaa tatgtagagg acttcattcg aagagaatac  64980
atatgaaatc atttaaatta aatcgtgttc gttatcaaaa catcatgtcg gtaggtggga  65040
atcctattga catccaatta gataaagtcc aaaagacatt aatcactggt aaaaatggtg  65100
gcggtaaatc tacgatgtta gaagccatta ctttcggact tttcggtaaa ccatttcgtg  65160
atgttaagaa agggcaaatc attaatagca cgaacaagaa agagctctta gttgagcttt  65220
ggatggaatt cgatggtaaa aaatacttca ttaaacgtgg ccaaaagccc aatattttcg  65280
aaatctccgt tgacggtgtt cgtcttgatg aatctgccag cagtcgtgac ttccaagaag  65340
aatttgaacg tagcatcgga atgtcatacg cgtcttttaa acaaatcgtt gtgcttggga  65400
cggcagggta taccccttc atggctctta gcacccctgc tcgtagaaaa cttgtcgaag  65460
acctttaga agtcggcaca ctcgctgaaa tggataaaat caataagtct ctagttcgag  65520
aacttaattc ccaaggacaa gttctcgatg ccaagaaaga tggtgttatc caacaaatta  65580
agatttataa cgagaatatc gaacgtcaaa agaaattatc tggtgataat gtagcgcgtc  65640
tacagaatat gtatgacgac ctagccaaag aagctcgttc attaaaagca gaaatcgaag  65700
aagctaatga gcgactactt aatatcgttc ttgatgaaga ccctactgag gcattcaaca  65760
agataggaca agaagcattc ttgattaaat ctaaaatcga ctcatataac aaagttatta  65820
agatgtatca tgatggtggc acatgtccta cttgtgcatc acagttgcac cagggtgatc  65880
ctattgtctc taagattacc gataagcttc atgaatgtaa tcactcattc gaacaactta  65940
catgtcacag agataatctg agtgtcctag tggacgaata tagagctaat gttaagacta  66000
aacaggacct tgcatctgat attcgtacta agaaacaagc aatgattgcc actattgata  66060
aagctaagaa agttaaagct gcaatagaac aagcctcagc tgaatttatc gaccatgccg  66120
atgagatagc tttgcttcaa aaagaacttg ataaaatcat taaaacaaaa tcagatatcg  66180
ttcttgaaaa ataccatcgt ggtattatca cagatatgtt aaaagattct ggtattaaag  66240
gtgctatcat taaaaaatat gtgcctctgt tcaacaagca gattaaccat tatcttaaaa  66300
tcatggaagc tgattacgtg ttttctattg acgaagaatt caatgaatct ataaaatcac  66360
gtggtcgtga agattttagt tatgcttcat ttagtcaagg tgaaaaggca cgtatcgata  66420
tcgcattgtt gtttacatgg cgagatattg ctgaaaaggt ctctggtgtt aaaatcaaca  66480
ctctgattct tgatgaggtt tttgatggtg ctgtcgattc tgaggctgtt aaggctatag  66540
ataccattct tggaagttta caaaatacta atgtgtttat tatctctcat cgtgaccatg  66600
accctcaaca ttatggacaa catcttcaga tgagcaaagt tggacgattt acggtaatga  66660
ctgtttcata aacgctttaa catgatgtgg ttataatgac cacatcaaat taaatggaga  66720
acatcatgga gtattcaacc ggtcaacatc ttctcgttgt ccctgaaatt aaaaaatatg  66780
ttttgaccaa tacgttttca ggtgaagaac atattgttac tgaacaaatg ctcaaatctg  66840
cttttaaaga tgagtataat aaaataatgt ctaatcgcaa ttccgcatgg acagttaccg  66900
acttctacga ataagagaga aataatatgt ttactactgc taaaggtttc actgctgctg  66960
atctgaaagt tacttctatc cgtactgacg ctaacccaca taaccataat cgtgttcgta  67020
aagcatgggt cctgcattgt gatgacgcaa gtgctaaaaa actccaatct ttgccacaag  67080
aaactcgttt tatgatttat ggttttattg ataacgatgt atctgatatg tggattcatc  67140
tgatgcgtaa gcactataaa gattctattg aagccggcgg aaaaaatcgtt cttgataaag  67200
atggttctga gcgtctagaa gatctctact gtgttgatgc cgacgaacaa ctaattgcag  67260
```

```
ctggcgaaat tgttgcttct aaaattccag aatatattga atcactgcct gaagctatta  67320
aaaagcagat ggttgctgca taataaattt gttataaact ttgaattgtc ttgaaaggaa  67380
ataaaatgaa actgtctaaa gatactatcg ctattctgaa aaactttgcc tctattaact  67440
ctggcattct gctgagtcaa ggtaaattta ttatgactcg tgcagttaat ggcaccactt  67500
atgcggaagc aaatatctct gatgaaattg attttgacgt agcactttat gatttgaata  67560
gcttcttaag cattttgagt ctagtgtctg atgatgctga aatttcaatg cacactgatg  67620
gcaatattaa aattgcagat acacgttcca cagtttattg gcctgccgct gacaagagca  67680
ccattgtttt tcctaataag ccaattcaat tcccagtggc ttctgtgatt actgaaatta  67740
aagctgaaga ccttcaacaa ttgcttcgag tttcacgtgg tcttcagatt gatacaattg  67800
ctattacaaa taaagatggt aaaattgtta tcaatggcta taataaagtt gaagattctg  67860
gactaactcg tcctaagtat tctttgactc ttaccgatta tgatggttct aacaacttta  67920
acttcgtaat caatatggct aatatgaaaa tccagccagg taactataaa gtaatgttgt  67980
ggggagctgg tgataaagtt gcagccaagt ttgaaagctc tcaagtaagt tatgttattg  68040
cgatggaagc cgattctact cacgacttct aagtcaaagc tttacgttta atgtagtacg  68100
attatggagg agaaatcctc cagtttaatg ataatgagga aaattacatg attactatca  68160
attccaaaga acacattcta gaacagaaat atcgtccttc ttccattgac gaatgtattc  68220
tgcctgcgta tgaccatgaa acattcaagt ctttagtatc taaaggaaaa cttcctcata  68280
ttattttgca ctctccttct cctggtacag gtaaaacaac cgtagcaaaa gcattatgta  68340
atgatatcaa tgccgaaatg atgttcgtca acggttctga ttgtaagatt gattttgtac  68400
gcggtccatt aactgcattt gctcgttcag tctcaatgga aggcaagccg aaagttattg  68460
ttatcgatga atttgaccgt agtggcctcg ccgaatcaca acgtcacctt cgtacattca  68520
tggaagaatt ctctagtaac tgctctattg ttattactgc taacaacatc gatggaatta  68580
ttgaaccatt acgtagtcgt tgtcgagtta tcgaattcgg acgtccaacc gaagaagata  68640
aaatctcgat gatgaagaaa atgattcatc gtatggttga aatctgtaag aatgaaaata  68700
tcgaaatcgc tgatatgaaa gttgttgcag ctctggttaa aaagaacttc ccggactttc  68760
gtcgtacaat tggccaatta gatcagtact cgtctaaagg tgttcttgat gcgggtattt  68820
tgtctatcgt aactaatgac cgtggcacag tctctgatgt tatcgaagca atgaagaaca  68880
aagatatcaa acagcttcgt gcattagctc caaaatatgc cgcagattat tcatggttca  68940
tcgataaatt agtttcagaa tgttatgacc aagttgcacc tggtaaaagt attatttcgc  69000
tttatgaaat tgcaggcgaa aacaataagt ttcatggatt agcaagtaat attgaattac  69060
acgtcatgta tatgcttctt caactgacct gcgaactgac ttggaaataa tatgaactta  69120
ttcgatgatg gcgtccagct taacgagcac caaattgcat ggaagtctaa tgacgctgat  69180
gcgattcaaa aatgtgccga tatgtttaaa gaaaaacctg agaatgaatt ctttaaaatc  69240
attaatgcta ttaatgaaaa gaaacctatg tcaattgctc aggtcgacta ctcaaaattt  69300
atggttgaga actcattatc ccagttcccg gaatgtatgc cagctgttta catgatgaac  69360
ttagtcggtt ctgaattaag tgatgaagcg cacttcaact atatgatggc ggcaattccg  69420
cgtggccgtc gattctctaa atgggctaaa ctagtcgaag acacttcaga gttactagtt  69480
atcaaactgt tgatgaaacg ttacacaatc aacatgaatg atgctaccga gtataagcgg  69540
ctccttgaaa aaaataacaa gttgccaata gtccttaaag aactgaaggc catggtcact  69600
gatgagtttc tcaaagaagt tacaaaaaat gtgaaagaac aaaaacaatt taaaaaatta  69660
```

```
gcattggaat ggtaaaaatg attgaaatta aattgaagaa ccctgaagat tttctgaaag  69720
tcaaagagac tttgacccgt atgggcatca ctaataacaa ggataaagtc ctttaccagt  69780
cttgtcatat cctccaaaag caaggtaagt actatatcgt ccacttcaaa gaaatgctgc  69840
gtatggacgg acgtcaggtt gatattgatg gtgaagacta tcagcgacgt gattcgattg  69900
ctcagttgct tgaagactgg ggattgattg ttattgaaga ctctgctcgt gaagatctgt  69960
ttggcctgac taataacttc cgtgttatct cttttaaaca gaaagatgac tggactttga  70020
aagcaaaata tacaattggt aattaaagca atgggacttc ggtcccattt ggagtataat  70080
aagttcatca acaaacaaaa gacaataact cgtctaaagg aaattaaatg aaagaatttt  70140
acttaacggt tgaacagatt ggtgattcaa tttttgaacg ttacatcgat tctaatggtc  70200
gtgaacgtac tcgtgaagta gaatataaac catcactgtt tgctcattgt ccagaaagtc  70260
aggctacgaa atatttcgat atctacggta agccgtgtac tcgtaagttg ttcgctaata  70320
tgcgtgatgc ctcccaatgg attaaacgca tggaagatat cggacttgaa gcacttggca  70380
tggacgattt caaattggcg tatttgtctg acacttataa ctatgaaatc aaatacgacc  70440
atacaaaaat tcgtgtggct aacttcgaca tcgaagtaac atctcctgac gggttccctg  70500
agccgtcaca agcaaaacat ccgattgatg ctatcactca ttatgactca attgacgaca  70560
ggttctacgt atttgatcta ttgaattctc catatggtaa tgtagaagaa tggtctatcg  70620
aaattgcggc taagcttcaa gaacaaggtg gtgatgaagt tccatccgaa attatcgata  70680
aaatcattta tatgccgttc gataacgaaa aagaattgtt gatggaatat ctcaacttct  70740
ggcaacagaa aactcctgtc attttgactg gatggaacgt tgagtcattt gatattccat  70800
atgtgtataa ccgaatcaag aatatttttg gcgaatctac tgcgaaacgt ttatcaccac  70860
atcgtaaaac tcgtgttaaa gttatcgaaa acatgtatgg ttctcgtgaa atcattacat  70920
tgttcggtat ctctgttctt gattacattg acctttacaa aaaattctct ttcacaaacc  70980
aaccgtcgta ttctctggat tacatttcag aatttgaatt gaacgttggt aaactgaaat  71040
atgacggccc tatttctaag cttcgtgaaa gcaatcacca acgatatatt tcttataaca  71100
ttatcgacgt gtatcgtgta ttgcaaattg atgctaagcg tcagttcatc aacttgagtt  71160
tggacatggg ttattatgct aagatacaga ttcaatctgt gtttagccca attaaaacat  71220
gggatgctat tatttttaat agccttaaag agcagaacaa ggtgattcca caaggtcgtt  71280
ctcatccggt tcaaccttat cctggcgctt ttgttaagga acctattcca aatcgataca  71340
aatatgtaat gagtttcgac cttacatctc tgtatccaag tattattcgc caagtgaata  71400
ttagcccaga aacaatagca ggaacgttta aagtagctcc attgcatgat tatattaacg  71460
ctgttgctga acgtccttct gatgtgtaca gttgttctcc taacggcatg atgtattata  71520
aagaccgtga cggtgttgtt ccaactgaaa tcactaaggt ctttaatcaa cgtaaagaac  71580
ataaaggtta tatgcttgcg gctcaacgta atggtgaaat aattaaagag gcattgcata  71640
atcctaatct ttctgttgac gaaccattag atgttgatta tcgtttcgac ttcagtgatg  71700
agattaaaga aaagattaaa aagttgtctg ctaaatctct taatgaaatg ttgtttagag  71760
ctcaacgtac tgaagttgca ggtatgactg cacagattaa ccgtaaattg cttatcaact  71820
cactttatgg tgcacttggc aacgtttggt tccgttatta cgatttgcgt aatgctactg  71880
caatcacaac atttggtcaa atggctttac agtggattga acgtaaagtt aatgaatatc  71940
tgaatgaagt ttgtggtaca gaaggtgaag ctttcgttct ttatggtgat acagactcta  72000
```

```
tttacgtatc tgctgataaa attatcgata aggttggtga atctaaattc cgtgatacca  72060
accattgggt agacttctta gataagtttg cacgtgaacg tatggaacca gctattgata  72120
gaggtttccg tgaaatgtgt gaatacatga acaataaaca acacttaatg ttcatggacc  72180
gagaagctat cgctggtcct ccgctcggtt ctaaaggtat tggtggattc tggactggta  72240
agaaacgtta tgcattaaac gtgtgggata tggaaggaac cagatacgct gagcctaaac  72300
tcaaaatcat aggtctcgaa acacagaaat cttcgactcc taaagcagta cagaaagctc  72360
ttaaggaatg tattcgtcgt atgcttcaag aaggtgaaga atcattacaa gaatatttta  72420
aagagtttga aaaagaattc cgtcaattga attatattag catcgcgtcg gtatcttctg  72480
ctaataacat cgctaaatat gatgttggtg gattccctgg tcccaaatgc ccgttccata  72540
ttcgtggaat tctgacgtat aaccgggcta tcaaaggtaa tatcgatgca ccgcaagttg  72600
tagaaggtga aaaagtatat gttctgcctt tacgtgaagg aaacccattc ggtgataaat  72660
gtatcgcatg gccttctggt actgaaatca cagatttaat taaagacgac gtacttcatt  72720
ggatggacta cactgttctc cttgagaaga catttattaa accacttgaa ggattcacat  72780
cagcagcgaa actcgattac gagaagaaag catctctgtt cgatatgttc gatttttgat  72840
ataatgacat ggacggtaaa ctaattaaat gagagaaata tgaaaactac tcctattact  72900
atcgctatta acgcaatcat aaaacaagct tcttctttgg ccgctatggc caaagtaatt  72960
agtcaaaacc ctgctcgtta taatgctatt ctagaaactc ttcgacgccc aggacttagt  73020
aattatgaaa gccgagtaat tattacaggt gttggtaaga atgctaatat tgcaactaaa  73080
gcttctgaga catttgcttc actcggtatc ccgagtatgt acttgaacac tgggcattat  73140
tctcacggtg atgcgggatt cattgcgcct aatgatgtgt tgattcatat tagtcgttct  73200
ggtaaaactg aagaaatgat aggcgtggct aagcatctta aaatgattcg tccgaacgtc  73260
aaacagattc tgttgcattg taacccagac attccacaag aaaatgaagc cctttttgat  73320
tactctttct gtacaggcat cgcagtagag gttgatgaga attctctggc tccgactatg  73380
tccactacat tgttgttagc gcttatcgat acgtttgcta tcaatctttc gtctgaacgc  73440
ggatttacct ctaatgattt ccttaagttc catccaggcg gtgcactagg tgccatgtta  73500
cgaggcgagc aatgaaagca ataacaatag gacttttact attgatgctt gtcatgacta  73560
tctactggag cttaacggct ccagtaatga ttccaacact tgtaattgga tggattatga  73620
ttggactaca agcgaagtat gaatgcttta actagaatag tgtacaatac tcctacttac  73680
caatgaggac ttcaacatga aaaaagctgt tattcttggt gctggactgg caactcgttt  73740
atatccaata acgcatcata ttcctaaggt gcttgttaac tataaacaag acactattct  73800
gagcaatttg tatacaattt attctgacct tggcgcagat gaaattattg tagtagttca  73860
ttcaaaattt gctgaaactg ttcgagctta ttgtgagcaa gaagggttca atgtgactat  73920
tcgtacagtt gatgaagcgt atggttctgc ttatgctctt gctaaattac acaaagattt  73980
agacggccat aacgtaattg ttaactggtg tgatattatt cctgattttg gttcatggtc  74040
ttggaatgtt aacgcaatct atgttaaggg tgacgaatgt cgatataatt tcgatggtga  74100
aaatatcact aatgtaggtg caacaggtgg taatgttgta ggaatttatc agttcaaaga  74160
ctgggaattc tacatgggtt ctaccgatga ggaaattcat gaatactgca aaggacgtga  74220
tttcgtagaa ttcctttacg ctagcgcatt caataaatca gagcttatga atataattga  74280
tttaggtgat atgcctaaac ttgaaaaagc tcatgaagtt cgtgaactta atcgtagttt  74340
taatgcagtt gaaattggtg aagaaactgt aactaaattc gcattaaccg aacagggtcg  74400
```

```
agctcttcag aaagatgaga tttcgtggta tttgaaagtg aaatcagatt cagttcctca  74460
gttagtttct gttaatgaaa ataactttga aatggaacgc attaaaggta agccggcatt  74520
tgaatatatt aaatccaaat caagtcttgc tcgtccacaa attgttgatg caattttaga  74580
tgcactgaaa ttcagcacag acacttattt tgtaagtcct gaaactgttc gtcgtgattt  74640
cactaaagaa ttctatacga aagttattga tcgttgtgaa agcattcaac ctttgattga  74700
ttcatttggt aaaatcacac atgtgaacta cactaagatt ggacgtctga agccaatgct  74760
gaaacaagct ttagaacacc ttattcgtta tcataaccgt tctcagggac agtactctgt  74820
tattcacggt gacccgaact tcagtaatac tatgattact gataacggtg aagtcaagtt  74880
tatcgaccct cgtggatatt ttggtgaaac caagatttat gggccaaaat tgtacgatga  74940
agctaaagtg ctttacgctg tttcaggtta tgatgaattc aatgctaatc cgacctgggg  75000
gcagtttact attgatgaaa caacttgtaa tgtgactatt aacatcaatc cattagttta  75060
caaatatgga aagatgagtt cgtttaacga gtatcatcat ttggcagtgg caataatctg  75120
gattgcatta ggtggttatt tcaaaaataa tccacttaaa gcggtagcag catattataa  75180
aggtatggaa cttctgacta agcaattacg taacatgggc cgtgtacttc aagacggctc  75240
tattagttat gacgtagcag aacctgtaac ggctactctg attacaaaaa atcctggtaa  75300
atgggtacta actgataaag aaactggtgt ttcctatcgt ccaatcggtg gcgatatcac  75360
tcatcaatgg gaacgaatct aatgcaccgt gtagaaaaca tgcttaatct ttgttttgat  75420
gtcgatgatt gtataacaga gtggaataac aatcgtgatt acgtgaactt caaaccagac  75480
gtcgaaatgg tgtctgccat taatgccctg tatgatgcag ggcataccat aacgctttac  75540
actgctcgcg gtatgaagtc agtaggtcct ggtcgtatag caattgacat tctcccaagt  75600
ctgattcaga acttggcaaa cattggtttg aagtaccata atttgctaac acataaacca  75660
gtatatgatt ggattatcga cgacaaagct atgcgtcctg atgaatttaa agctcttatg  75720
aataaaggcg aattcgaaac atttaaatca tataaaccga atctataata atttaagtaa  75780
gacctgcaaa aaccatcgcg tcaattaacg tgagatgcaa aaaaaaatga atacttttaa  75840
aatcggaacg aattttgatt tagctcttct tgataaaatc gtagagctca ataaaactta  75900
tcctaatagc ttgataaacg aagtatacgg ctctacaaga gaaatggctt ttgtagcagc  75960
cagacctgat tttaggcttc ctgacgttga caaaaagatg ttagaagatt acgttaaacg  76020
ttgtaacgaa ttaggtattt gctttaacta tacactcaac acgataaatc ctggttcaaa  76080
aagagaacta gttgagtgga agaagaaagc tattcaggat tatgttcagt atctttggtc  76140
aataggcgta tggcgtatta ctatcgctaa ccctgttgtt atggaaattg ttcgtgaagt  76200
caataaagac attgagattg aagtttcaac aattctacat gtcgatgctg taactcaaat  76260
caaatacttg catgaccaat ataatatcaa aaaggtctgc tgtggaattc ataagaaccg  76320
ttcagtttct ttcctgaagc gtgcagcaga gttttgtaat aagaacaata taatatttga  76380
agttctcgta aatgaattct gctctaatgc gggtaaaggg tatacaacac attgtagcta  76440
tcgtgactct tgctatattt tccatagcac cgatgttaca gtagatgatg ccaaatcctt  76500
aaatggatat ccaatgcaac actgtattaa agctcgtgat acagatccat ttaactggtt  76560
gagaactcgt tttgttcgtc ctcaagattt gaaactttat aatgatattg gtatcactca  76620
attcaaagtt tcaggacgta caggtagcac agactacatt ttgaaagttc ttgaagcata  76680
cgcttctgaa aagtttgaag gtaatttgtt agaactgtgg aagcctttag agaccatttt  76740
```

```
cactcttgaa aatgagaccg agttttcaca tacggtaaat attgaaacct ctttgttaga  76800
cggcttttta gaaaaaaggt ggttcagaca tccagatttc gattgtgcta atgaaatctg  76860
cgggacgacg tgtacatatt gtgaaagata ttataaacgt cagttatcta aaaatgggtt  76920
atcagaaaat tctatatcta ttattgatat aactaactct gacgacgctt tgaggtaccc  76980
agaatgattt ctagaaaaac ttttaaccac caacttaatg aagagatttt gactataaaa  77040
attaacagca acgaacaaat tcttaaaaag gccctaatgg gcctttttga aactaaagcg  77100
gctaaagtga ttaaagaacc tgttcaacta gaatactagg ccgacgcgtt ccttcatagt  77160
gtccttggaa gtatcgatgc cgaagctcta cgttatatca acatcgctaa gaaattcaaa  77220
taagctttat gaattgagta tataataact gtattgaggt aaacatggga aaacataaca  77280
caatgaaata tattaaagcc gcagattttc aatccgcatt taaagctgtc aatcgtgaaa  77340
ttttagaaaa tccacagttc gttactgatt ctcgtattgg acgttgtaat gaaattgggt  77400
ctatgacagt agttgttgat accccttcat cattcaaaat gaccgaccca cggattaacc  77460
gcatctctta tgaatatgcc gaagacttct ggaaatttat gatttctggt ggtactgatg  77520
cagaagaagc atttaaggca tatcctaatg tcgctaaatt tatttctaaa ccaaaatcag  77580
atgctttgcc tgagaacttc aacactttct atggtcctcg cattgcggcc caattaccaa  77640
ctcttctaaa agaacttaaa gagaaaccta actctcgaag agttgtgttc caaattctag  77700
aaagttctga tcaggctttg cttgattcgg atgaaacgct tgaatatcca tgtactgact  77760
cagtgactta ttatattcgt gatggtaagc tttataccca ctgtcatatg cgttctcaga  77820
actgtgctgt tgttatgcag ttggattttt atctccaagg aaaattactt cattatatcg  77880
ctaacgaatg tggcgtagaa gttggtgatt atactcatac catggtaagt gcccatgtgt  77940
ttgaacgtga ttttgattat gttaaaggat tccttgacta atggctattt tccgcgtacc  78000
tatcttgagt atgcggtctt atgaaactgg acagtatgct atccttaagg atggcaactt  78060
ccaacttcat ttgcaccgtg ctaatccagg tgatgtgatt acatatccac gtaatgcatc  78120
tgatattaaa gaatgtgaac gtctttttcc ggaatttaag tttgttccat tatggtataa  78180
agataacgcg tataacactc gtaaatattt ctggtctgaa aatgaatttg tggttgattc  78240
attaattgat tattatgatt gtgattttct aatcacagat atcactggat atgacggtac  78300
ttttgacgta gaattcaatt tcaatatcac tgcagaccct aataaaccac gtttttatat  78360
tgacgaattc ttaaaaaccg acatgttgtc ggttaatcgt tcacttcaaa ctactgtgtt  78420
gaatgaacgt caaaaggaag tgctggttaa cgctggtgcg gatggtaata agattatcgt  78480
aacgcagaaa gttatacgtc cttccatcat gcagcgtctt gtaggtgatt tggctcctat  78540
tcatctagat ggtatttttc atccatttcg aattagtgac ccgtgctatc gttttgaaca  78600
agtggttgaa tgtgcaattc aattaggcca accgctttat ataaccgatc caaataatag  78660
cttcgacaga aataagtatc ctgaagaagc gctgattcga atttttaatc caactaaaac  78720
tgagtactat caaattctta aaggacggcc gaagattcaa tatttcgaaa atcctgaaga  78780
agtattccat ccaggtcttg gtgagttcat ctactttaat gctttaattt cttcaccgta  78840
taatatacct aaatatgaag atgtcgtaat cgaggaataa aatggctaaa attattttag  78900
tagatggccc ggataatgct ggtaaaacaa ctttcattaa tgacataatg gaaattagtg  78960
aaagatatgt aaagattgat ttccctaaac gaacagttga tggacgtttc gatgttaagt  79020
ctcgaaatga agttggctgt ttcgaaacga tgttgaatta tttagatcct actaagattt  79080
atctgttaga ccgtggatat attagtaact gggtttatgg acgtattcgt caagatgctg  79140
```

```
actcggttct tgacgtttat gaacaggatt atgttcgtct ttgccaaaac catgatgtgt  79200
tcacaattat tttaacacgt aacgaaatga ctgaaagttt tgaagacgac cttattactt  79260
tatcttcatt cggttttaat acagtcattt catattttga agagtttgca attcataacg  79320
aaatccaaac gtatcaatta cttaatcatg atggtgctaa caaagttata ggatttaatg  79380
caagcgaacg taataatttg attacagaaa ttatcaaatg ggctcgttaa gagcctgttt  79440
aaagttttaa acgctgtata acccttagta tataatcgtc ttatctttta aacatgagta  79500
aaatataatg atgcctatgg aaaaatacaa tgtctgattt aaaatctcgt ctgattaaag  79560
cttctacttc taaaatgact gcagacttga ctaagtctaa gctgtttaat aatcgtgatg  79620
aagtccctac tcgtattccg atgttgaata ttgcattagg tggtgcactg aatgccggat  79680
tgcaatcagg cttaactatt tttgctgctc cttctaaaca ctttaaaacg ttgtttggac  79740
tgaccatggt tgcagcatat atgaagaaat ataaagatgc aatctgtttg ttttatgact  79800
cagaattcgg tgcttcagaa tcttacttcc gttcaatggg tgttgatttg gaccgtgtag  79860
ttcatactcc gattcaatct gtagaacaac ttaaagttga tatgactaat cagcttgacg  79920
cgattgaacg cggtgataaa gttattatct ttatcgattc aatcggtaat actgcatcta  79980
agaaagaaac cgaagatgcg ttgaacgaga aagttgtagg tgatatgtct cgtgctaagg  80040
cacttaaatc tctgttccgc attgtgactc cttatctgac tattaaagat attccatgtg  80100
ttgcaatcaa ccatacagca atggaaatcg gcggtctata tcctaaagag attatgggtg  80160
gtggtacagg tattctttac tctgctaaca ctgtattctt tatctctaaa cgtcaggtta  80220
aagaaggtac agaattgacc ggttatgact tcacgttgaa agcagaaaaa tctcgtacag  80280
ttaaagagaa atctactttc ccaatcacgg ttaattttga tggcggtatt gacccattca  80340
gtggcttgtt agaaatggca actgaaattg gttttgtagt taagcctaaa gccgggtggt  80400
atgctcgtga attccttgac gaagaaacag gtgaaatgat tcgtgaagaa aaatcatggc  80460
gtgctaaagc tactgattgt gtagaattct ggggaccttt gtttaaacac aaaccttttcc  80520
gagatgcaat tgaaactaaa tataaactag gtgctatctc ttctattaaa gaagttgatg  80580
atgctgttaa cgaccttatt aattgcaaag caacaactaa agttccggtt aaaacttctg  80640
atgctccgtc tgcagcagat atagaaaacg accttgacga aatggaagat ttcgatgaat  80700
aatctcgatg atttaaatct agaaatcgtt gatgaatccc cttcttcgga aggggaagac  80760
attcgcaaag aacgagtgtt taatgaatct cttaaaattg tccgttcagc aatggaaaat  80820
gtcattcaag agattctgat tacacttgaa gatggttctc atcatatagt ctatatcaca  80880
aaactagact gggttgatgg taaaatcgta atggactttg cagttcttga ccaggataga  80940
aaagcagaac ttgcaccaca tgttgaaaaa tgtgttacaa tgcaagtaca acaagctttt  81000
aatgaacggg ccaagaaaaa atttaaattc ttttaaggag ttatcgtggt agaaattatt  81060
ttgtctcatc tagtatatga ccaggcttat ttttctaagg tctggcctta tatggattct  81120
gagtattttg agcgtggacc ggcaaaaaat gtctttaaaa ttataaagag ccacgttaac  81180
gaatataacg caatgccgtc tatcaatgca ttaaaggtgg ctttagataa cagttcttta  81240
actgaagcag aatataaagg aacttcagac ctaattgaaa aattggctga tactcctgaa  81300
gaccacgaat ggttggttaa agaaactgag aaatatgtcc agcaaaaagc gatgtataat  81360
gctacatcca aaatcattga gattcagtct aatgctgaac tacctccaga acaacgtaac  81420
aagaaaatgc ctgacgtagg agctattcct gatattatgc gtcaagcact ttcaatttcg  81480
```

```
ttcgatagtt atgttggaca tgactggatg gaagactacg aagcacgctg gctttcttat  81540
ctgaacaaag cacgtaaggt cccgttcaaa ttaaacattc tgaataaaat cactaaaggt  81600
ggtgctgaaa ccggtacact gaatgtttta atggccggtg ttaacgttgg taaatcttta  81660
ggcctttgtt cacttgctgc agattatctt caaacaggtc ataatgttct ttatatttcc  81720
atggaaatgg ccgaagaagt ttgtgctaag cgtatagatg caaacatgct tgacgtatca  81780
cttgatgata tcgatgatgg taacgtatct tatgctgaat ataaagccaa gatggaaaaa  81840
tggcgttcaa aatccacatt aggacgttta gtagttaaac agtatcctac cggtggagct  81900
aatgctaata cattccgtgc attgcttaat gaattgaaac tcaagaagaa ctttgtgcca  81960
tctgtaatca tggttgatta cttaggtatt tgtgggtctt gtcgtatcag agtttacact  82020
gaaaatagtt acacgttagt taaagctatc gcagaagaac ttcgtgcatt agcagtagaa  82080
tctgaaacag ttctatggac tgcagctcaa gtaggacgtg cagcatggga tgcttcggat  82140
atgaacatga gcgatattgc agaatcagca ggtttaccag caacagcaga tttcatgttg  82200
gccgtaattg aaacagaaga acttgcacaa gctgaacaac aacttatcaa acaaatcaaa  82260
tcacgatacg gtgataagaa taagtggaat aaattcctga tgggtgtacg caaaggcaac  82320
cagaaatgga ttgagattga gcaagaaggc atgaacacac ctaacacagt aaatgaaaac  82380
gcaggtgctc agatgcggca ggcagaggtg aatcgcacgg aacgcgtagg taaagccaaa  82440
gcaacacgtg ctgacctaga tagcttagcc aatgagttaa aattttaata aaaaggagcc  82500
ttcgggctcc tttcggggtt tacatcttcc tctaggcatg atatgatgta cttacacaaa  82560
ccaagaggaa aacactatga atatgtctca agcaattttt actgcaatca ccgaaaacac  82620
aactgttgaa gtagtttctc cgctggcaac ctacgttatt cttgctccta aaactattgt  82680
atctcgtatg gaaaacatgg gcaaacgtat cgtacaaata gttggagctg gaaatcaaaa  82740
acttgattat ctacgaacca tcaaagctta tgaacatttc caactcgaaa aaggttctcc  82800
tatccaggta gaactcgtaa atggtgatat cgttcgagca atgttccatc atttctatgc  82860
gttgaatgac ccatctaaag cagttcgttt aattgcatac gacgcaaacc aaagcgaaat  82920
caacgcagat gtatctaaat tacgttttta agtttacttc tccagtagtt gtgttattat  82980
agacctatca actactggag aacaaaatga aaaccatcga ttgtaaagca gaatttaaga  83040
ttttttatca cggttcaagt agttcagcta acatcgaaaa catgctttgt cctcctgagg  83100
aaacaggagt tttgtctgaa actggacgca agaaaaactt ggaccgtgta ttctttactg  83160
aagatatcgg tttagcaaag atttatgcag gacgagcagc acgctcttat ggaggtgaac  83220
cacgtctcta tcgagtaatt tctccggtag atgtagttca aatgaataat actaaaggtg  83280
ctacagttta tcacgctgaa tggcatttt gcgaggaaat atgagcaaat taactaaagt  83340
tacttttatt ggctggttta aaaatgataa tacgttcact aaagatatca tgttatcagg  83400
tgaccgtgaa gaaatcgagt gggttgcggt acaacttgct gaagtgaaca aagcattagt  83460
taaagcattt gttaatgacg agaaagtttt tgaagctgat ttcagaggat aatatgtatt  83520
caactgtgtt taaaccatca acatacgaat ttgcatcaac tacacaatgg aaagctctta  83580
ttccggaagg atgggaacta atgatggact gtgaagcatc tgaaaagttt cctcacggca  83640
aagtggactt cgttaaattt gctgtacgtc cgactaaacg acagattcgt caagaaaaac  83700
gcaaatttcg caaaagttta aaataactgt ttacaagcac cacatactgt gttactatct  83760
ttctatcaac tacagaggaa attgaaatga aaaaattaat cgctttagca atggtatttg  83820
gattaaccgg atgtggtgcc catggcttta tccctaataa cgttggccaa ctgatttaca  83880
```

```
atccgaatgt taaacagtat gaccgaccta aagttgaagt ggaagacccg gttactgtag  83940

gtaatcgaat gattcaagct gatgctcatg ctcaacgtta tcgtgattct gatactgtag  84000

ctatgtcaaa agaacagcgc gttaaagaac attgcttaca ggctactgaa atcgcattca  84060

ttcgctatgt tgaaacaact ggtaaagagc ctacccagaa acaaatcgcg aataactaca  84120

tccagtgtat tgaacgttta aacaaattta attaattggt ttacactaaa gttaaaccaa  84180

gatactataa acataacaaa tcaagaggaa attaacatgg aattattcgt agctagttca  84240

gtagcagttt taatcgcagg tattggttca atcatcattt acatgttgcc ttgggtaatc  84300

gcacttattc gtggcacaaa aagcacaaca gcaatcttct tcgtatcttt actctttaac  84360

tggacgatgg ttggttggat tggaacttta atttggtcta tcgttgccga aaagaaatct  84420

gctctacagc ctcaacaagt aattattatt cgcgaaaaag aataaacttg tttacattat  84480

agatggacta tagtatagta gtcctatcaa atcaactaag gagttaaaat gaaaaagtta  84540

tcattggcag caatcttact tgcagtatca tgtgcaccgg ctccagttac ggcaggttat  84600

gataaagacc tctgtgagtg gtcaatgact gcaaatcaag aagatgttga acaacaaatc  84660

ttctctgata tcgtgaacat cactaaacga gaccgtccta atatggttaa taaagttgtt  84720

gaacaactta agtccggtgg tatcatgcag tacaattatg ttttgtattg tgaccctaat  84780

ttcgataaca aagatatcgt aaccgaaatc acaggtgaat aatatgattt attacatgca  84840

caaaaacgcg ccatttaaat atggtaaatt tcctaatgca caatgttata atataacgcc  84900

taacgaaaat aataacggat accatattgg tgtaattttt gtaattgtta aagataacga  84960

aatcgttgcc tgggcagatt ttaaaggtac aacgtatgat gttaatccgg tgcctttcac  85020

atattacaat ataatggatt tggcatatga ttataattgg tttaatcacg acgcgttggc  85080

tcatattgaa ggtgtaggat ttgacatctc ttattctagt tattcattat gtcctatgag  85140

ccgagctcac ggtaaagatg tatcatatct ttcaattcgg aaacgtgtaa acttcaaacg  85200

tagtacagag tatgttggtg gactctttgt taaagataat aaaataaccc gtattagtta  85260

tcctttaagt gtaggtcaaa aagatgttga tgttgattta gacttaaccg aaaataacat  85320

taatcgtatt gcttctgtat attttgatat cgatgaaaaa attgtagtgt gtggatacga  85380

attaccacct gaagaaaagg ctgaagcaat tgaagtcgaa ttagaaattt ctgtcgatga  85440

ccaaatattt aatgcattta tgaatcgagg ttaaaatgac tactgcaatt tgcactggtt  85500

ctaaaattag tgtttttaca agttttgaag attatgaagt tgtttcaaaa caccaatgcc  85560

atattagcgt aaaagctaat gatggtgtaa tttggaatat tccacagtat gaaggcacta  85620

cgtatgaagt cacagatata aatggtgaca aagcgatctt tgtaattgat taaatatact  85680

caggaggtac ctatgggtat tattaacact gcaatagatt ctgtttatgc atataagttt  85740

attcgactaa tgcaaaaacc ttttaccgaa tggaaagcat acgaagccaa aatcatcgat  85800

gaacgtggaa gtgttcttaa acgtccttct actcctgaag agaaagcggc gtatacacct  85860

tttcatgctt cagttcgttc aatgaagcga atgatgagca ctgttccagg tcttaatgga  85920

atggcctcaa tgatgtctgc ctggagtgct gtagcttcac gctataacat tacggaagaa  85980

caacagaaag aaatatttaa agaactccct ttatttgagg atatggttgc tggtgattca  86040

ggcggcagtc ctcaagctat tgcatcagga acaactacgg gtgcagtcgt aaataaaggt  86100

ccagaacaaa ttccttccaa gaaaagaaag cgaattaaag taaatattaa taagttgtga  86160

taagatggcc ttaaattaat aaggcctctg gagaatacta tggctgaatg gatagataat  86220
```

```
gaatttgctt atcgtgcgtt ttctcaccta cctcgtttta gacaaatcaa taattcaagc  86280
acatttaaat taacatttcg ttgtccagtt tgtggcgact cacagacaga tgcaatgaaa  86340
gctcgcggat ggtattacgg cggtactcct ggtaatgtac attgctataa ttgtcaatac  86400
cacaatacaa tttccggata cttaaaagag tatgatgaag agctttatcg cgaatatcta  86460
atggaagttc gtaaagaaaa agctagaatg gaaccaaaga ttgaaaaggt tcctgaacat  86520
aaaccagaac cggagaaaaa gactataaat tctttgcctt cttgttctcg tctggacaag  86580
ctgcctgaag agcatcctat tgtgaaatat gttaagtctc gatgcattcc taaagaatca  86640
tggaacagat tatggttcac attagaatgg cctaaattgg tcaacaagat tcaacctggt  86700
acgtataaga aagagattcc cgaaccacgt ttagtgattc ctatttttaa taaagacggg  86760
aaggctgagt cattccaagg acgtgcactt cgtaaagatg ctcctcagaa atatatcact  86820
attaaagcgt ttgagtctgc aacaaaaatt tatggtgttg aacgtgttaa ggaaggagac  86880
gtctgggtaa tggaaggccc tattgatagt ttattcatac ccaatgcaat cgctattaca  86940
ggcggctcaa tagatttaga tgtggtacca tttaaagaac gtcgggtatg ggtaatggat  87000
aatgaaccta ggcatccgga tactatagct cgcatgaagc gattagttga tgcaggcgaa  87060
cgtgtcatgt tctgggaccg agctccatgg agatcaaagg atgtgaatga tatggtaatg  87120
aaagaaaatg caacaccaca agaaatttta gaatatatga aacagaatat ttcaagtggg  87180
ttgcatgcta aaatgagatt atctcgttat tcgaagattt aaacaagccc tataatagca  87240
aaggccaaat caactacagt atccaacgga acagaaggaa ctataacacc atgggcaact  87300
aacaatggtg caatcccgaa gttccatgaa ataatgccac ctacaactat tgcagcgata  87360
gcagttttct ttttattgcc tttaatagct ttgattaacg acggaagttt aaacataata  87420
tctccttagt tacctattat ttattacgct ttataaaatt aatgttagaa ttaactctct  87480
tatactgaat tgaaaggaaa aataatggca cactttaacg aatgttcaca acttatttct  87540
ggtgttgata aagcagaaga agcttatttt aatgctctga ttcacgaaga taaagaccca  87600
ctgcaggtaa tgcttgatat gcagaaatct ttacaggttc gtctggcaaa tgacaagcct  87660
gaacataaca aacatcctga tgaattggct actgccggtg atgttgttga ttggctgcgt  87720
aatcagaaag attatattga tgatgaattc cgtgaactgc tgacttcact cggtggtatg  87780
tccaacggtg aaaaagccgc tagctctgta tggaagccat ggaaagcaca acatgctgaa  87840
tatcgaaatc gtcgtatcga tgaactgtct cctgaagacc agcttgaaat taaatttgag  87900
atgattgata tcctccactt tgttctgaat atgttccaag gtctgggtct ttccgctgaa  87960
gaaatcttta aactttacta cttgaaaaac caacacaact ttgaacgcca ggataatggt  88020
tactgattaa gttataaata cacctgtaat taaacaacaa aggagttaat tatgggtggt  88080
tatgtaaaca tcaaaacctt tacgcatcct gctggtgaag gtaaagaagt taaaggtatg  88140
gaagtttctg taccgtttga gatttattca aacgaacatc ggattgcgga ttctcattat  88200
caaatctttc cgtcagaaaa ggcagcttat tctactgtag tttctgatgc agctgactgg  88260
aaaactaaga acgctgcaat gtttacccct acaccagtaa gtggttaaat aatttaagga  88320
atccttcggg attccttttt tgtttctaca gtttacaacc actaaaaact gtgttaagat  88380
attcttactt actcaagagg agaacaatat gttaaatcgt tggattaaac ctaataacac  88440
attaggtgct ttgattgctc aagaagtttc gttgaaatat ggtcttggat attacgatga  88500
tgtagtcgta cactcattca tgatggatgg tgaagacgtc aaatttaatg ccgaaatccg  88560
ttgggatgat ggtggtgttc gttttgttcg aggaacaatt aatgcttacg atgctgaaga  88620
```

```
agttgtttgc tgttaaacca ggcgaaggta tgatgcctat tcctgataca cacgaaaaaa  88680
gttgggaata cattggtgac ggcatgatgg aagaagttat tcgtccaaaa acaaaacagg  88740
ttaacgcttc aagctcttca agttataatc attcatacgt atcgtcttgg cctggtgatt  88800
ctgggtcaag ttattcttat tgtggttcaa gctcagggag ctgcgaatga acaagatagt  88860
taaatggttt aaaagctggg acgatggtgt cggaccagaa gattggctgg atgttcttga  88920
agagaatatg gctaaagaat tccagaaaca tgaagaaaaa ctcgtcgaag atgaaggcga  88980
acgtattgtg aaactttata tgggtgaacc atcgaggaaa ttataatgga cgctatgtta  89040
tttaaaatgt atttgcttga agccaagtcg tttaaacata taccagtaga agataagact  89100
ccactagaaa tagctattct cattaacaaa agtctaaata atccgcaata tatcgtagaa  89160
gaattctgca aattgcagat tcctaaaggt tacaaaattc gtgtagagcg agttggagct  89220
attactcatt ctaaaaattc cccgtttagt cttgaagaag gcataaagga cttaggttat  89280
gaatctacgg aaaatgcagt ttatgtgaat cctgaaaagc gtttagactt atttgaaaag  89340
cgagactata agtattttgc caaaaaatac tttattacat cattagcaga tttaatccat  89400
ttgcaacgag ctatttggaa attttttaag acaaaaggcg tagcactaga aacattctct  89460
gaacctgcta gtttttatct cggtgaataa tatggacttg atgagtatgt ttgatgagcc  89520
tcaacttcag gctcctaaag tgcatcgtag tgaacttgtt gatgaactag atagtattat  89580
acaacgtcac ggctttagtt tacctgttga agccctgaaa gaccttgcct cttattacga  89640
cgaccctcca ccatggagtc cttggaaatg aaagagaaat ttaaagagaa attcttacta  89700
gaaatcaagg aaaaagactt tgagacatgg tatcgaatgg tgaaagggtt gacattgctt  89760
tttaaagcgt ccttattcat gttagaacaa cctggccctg atggaccttt agtaggaaag  89820
cttaaaaaat agtttacatt ccctcctctc gtgttatgat aggcttatct ttaaatggag  89880
gtctatcatg acatgtcaat ctgaacttca agaacgtgaa tacctaacaa atctgattga  89940
tagcaaattc acccgccaag aacaaaacat tctctgggct tgcaccgatt ctaaggaaga  90000
cccggatttc cactatgaat tagaccatct tgttcgtaag catatgactt ctacagtacc  90060
agtagaactc taccgtggtg taactccaga agaagtagaa cgtctttctc ttctttctgt  90120
tggatgccat tggtctcctg gacgagtaac atcgttcaca actgatttca gtacggctcg  90180
tcaattctct gggagatggg aatatcagac gtacactatt cttagtctca ggaatgctcc  90240
attcattttt gattactacc aaaacatggt taacattgta cttgccggaa agaaccctaa  90300
gcatgttatg gaagaaacac gtgttgacgt cctagatatg attgaatctg aacaagagta  90360
catggtctca ggtatctcta gatttgagat tgtggaaatt gaagacttag aatatgaccc  90420
tttatctcga ttatacaaaa tcattcattt aaaaatgttg aatttttagt gtacaaactc  90480
ttccgacgat gatactatac ttttatcaac cacaggagaa acctaaatgt ttatgccgta  90540
taacgagtgt gaaattgaag aaatggttcg acgtgctcaa tgcccggatt atcaagatat  90600
gcttcagtac aaaatcgatg agcaattcag cgacattgaa caaagtgtac tatggcagtg  90660
tatggaaaac aagccagact gtattcaaca ggagttaagt gcaattgttc gtagaaattg  90720
gtcgtcttct gttcctgaga caatgtatcg tggaatctct aagaaaacta tggccacact  90780
cgatgataaa ggcattggta gtattattaa atttgacaga gtaatgagct tcagcccagt  90840
gttcggtgta gcacgtaact ttgcttcgta taatttttac ggaacattta atatgttctg  90900
catcaaagat gcaccatttg ctttcaactt ccgtgaacat atgcttaata tgattctggc  90960
```

```
tgcaccatct tgcgagttca atggagcttt ccctgaagcg acaagacggt ctaatgctag  91020
acttatatct gacgaatgtg aatttatgct ccctataggg actacactgc gtgtagattc  91080
tattattcaa gatggacgtt atacaatctg gaatctgtct attgtcagtt actgactgga  91140
ttggaataac cggatggaac tcagaaccat tataacacat aaaaaattaa agcattttat  91200
gaaaaaagag tgtacactac ctgagggcat gatattatag gacatatcag ctaaatgacc  91260
taacgtccgt aagacagagg aaaatattat gttatcaaat aataaaatta acaaaatcaa  91320
tcgtcgtctt gaccacacca gagcttctgc gaagagacgc tctaaggatt ttaacttaga  91380
ctttaattac cttaaaaaca ttcttgatca aaaggtctgc gcttactcag gtgaatcttt  91440
caataactct gttgaaggtg agaaattatc cttagaacgt tttaataatg atataggcta  91500
cattaaaggt aatgtcatcc cagttaagaa aaaatataac acggctcgtt ctgatttaac  91560
attagaagaa cttattgaga aacgtgacgc tattgcaaga cgtattgcta atccttctgc  91620
ccgtaaagta gagaaactta atctcgacga gaagaaatgg gcccaaatta aaaaggttta  91680
tggtactatt ttaaaaatcc gagcaaaacg tgaaaatcgt gttaagcata tggcgaacat  91740
gatgaaaaat caacctttat ctaacgaatc taaacttaga attgttgctt tgaaagcacg  91800
cattaatggc tcacatcaag cagaaggcca tgaacttact aaactcaacg ttcttcttaa  91860
aggctctgac tggaaaacta aaactaaatt aactgacgct gaatcgcttt tcgatacata  91920
tgataaagtt atccaaggtc tgcaacgttt tgaaaagatc ggtttcattg gtaaattaaa  91980
attgaaacgt ggcttaccac ttagcgcatc attattccaa ctgattaaag gttaattatg  92040
gtttatgtat atgcaatagt ttatcgagat atggaaggat ttactgtccc ggttccactt  92100
gatgagcatc gtcctgcagt attttttaga aaggatattg cagataaagt tttcgatact  92160
ttgaaaacac agtataaaac agatttaaaa atgggagttc taagaatggt cgaaactccg  92220
cgtaagttct ggtttaataa gcttgaaatg aaacgcatta aactagatgc ggagacgcaa  92280
aaattatatc aacgaatcct ggacacaggc cgtattgtta gtattccaat tgcagggact  92340
ttacgatgac atttgatgat ttgactgaag gccagaaaaa cgccttcaac gttgttatga  92400
acgctattaa agaaaagaaa catcacgtaa ctattaatgg gcctgctggt acaggtaaaa  92460
caacccttac tagattcatc gttgaagccc ttatttcttc tggagaatca ggtattattt  92520
tagcagcccc tacacatgct gctaaaaagg ttctaagcaa actcgcaggt caagaagcat  92580
cgactattca tagcattctt aaaatcaacc caactacata cgaagaaaac gtattgtttg  92640
aacagaaaaa ggttcccgac ttagccttgt gtcgtgtact gttatttgat gaagcatcaa  92700
tgtgcgaccg ttctctgttt aaaataatgt tagctagtat ccctaaatgg tgtacagtaa  92760
ttggaatcgg cgaccgatgc cagattcgtc cggtagaccc aggcgaatca actgcgtatc  92820
taagtccttt cttcactcac aaagacttcg tgcaatgcaa ccttacagaa gttaaacgta  92880
gcaatgcacc aattattgat gttgcgactg atattcgtaa cggcaaatgg atttacgata  92940
aagtagttga tgggcacggt gttcatggat atacagacct taaatcgtat atgatgaact  93000
attttaacgt cgttaaaact cctgaagacc ttttcgaaaa tcgaatgatg gcattcacaa  93060
ataagtcggt agacaagtta aattcaatta ttcgccgaaa acttcttgaa acagaaaaac  93120
catttattaa agacgaagtc attgttctac aagagccatt tactaagaca tataagctag  93180
atggtaaaaa tatgaccgaa atgcttttca ataacggcca attcgttcgt attcgagatg  93240
ctgtagaaac gtctacattc gttaaagcgc gtggtgtttc aggcgaatat atgatacgat  93300
actggaatct tacagtagaa acatatgggg atgatgaaga atacatccgc gaagatataa  93360
```

```
aggttatttc ttctgaagaa gagctttata aattcaattt gtttttggct aaaaccgcag  93420
aaacatacaa attttggaat aaaggtggta aagctccgtg gagcgaattc tgggatgcta  93480
aacgtatgtt cactaaggtg aaggcactac cagtatcaac cttccataag gcccagggta  93540
tgtctgttga cacggccttt gtttatacac cgtgtatcca ttatgccgat tcagaattag  93600
ctaaacagtt attgtatgtt ggcacaactc gtggtcggtt tgacgtccat tttatttgag  93660
agaaaattat gagcactgat gttattatag attttgaaac attcggcaat acatcaaaag  93720
cggctgttat tgaccttgcg gttattgcat ataattccga ccctgaagtt gttgaatcat  93780
ttgaagagct tgttcaacga ggtaagcgaa ttaaatttaa tttagcttct cagaaaggga  93840
agcgagtttt cgctaaatcc actatgaaat ggtggaaaga acaatcggct gaagcgcgta  93900
aaaacttggc tccgtctgaa gacgatgtca ctacgcttga aggcattaaa atctttttag  93960
attattgccg agctaataaa gttgaccaat ggaaatcaca gatgtggtgc cgtggtatga  94020
gctttgactt cccgatattg gtcgatttga ttcgtgacct ctatcgtgat gaaggtgttc  94080
ttgaaccaga gattgatact gataaattag aaccggttaa attctgggct caacgcgata  94140
ttcgtacggc aatcgaagct tactcgttga cacgaggatt aagtatgtgc ccattaccga  94200
tgggtacgct aaaaggattc gttgcccatg atagtattca tgattgtgct aaagatattt  94260
tgatgttaaa atatgctcag cgttatgcgc ttggccttga agatgtccct gagaatcctg  94320
acccgttaag tgtaaaacag cgataaaacc agtttacaac caaggatggt tggagtataa  94380
tctttctatc ttaaccaaac aggaaaaaca ttatgaatat caatactacg gctacttaca  94440
tcctgaaaga cgaaaaacaa atcaactggt acggtgcttc agtgcgagct tatgaaaagt  94500
tttgtgaaat tttaggtgcc actcaaggta atagtttcac tattgttaac ttcatcaaac  94560
aagctgaagg cccttggtta ttcttagaaa ttaaaaattc acacggtaca atttctacta  94620
ccgccattcc aagcactgac tttgaactgc tgattgaaga agcacctgtt aaagatggtc  94680
tccactttga tatggatatc gcttgtatgt acggtactct gattaagcct attgagccta  94740
ctgatttgtt gtgtaaagct gtttcaattc gacgtccgtt cgcaggtcca gtgagtggat  94800
gggtaactga tcagtggatt gaagacggtg ttgaacttct gaacgttgtt catgccggtg  94860
attttagtgt tgttccacgt agtgcagtag ttaatatcct taattaatga tgtacatcca  94920
aggatggatg gagtatagtg aattcaattt aaacaaagag agagaaatta tgattactat  94980
tggtgaaatc cttcgtgtat ctcctgcttc tcgttctaaa gctgcaggtc gtctggttga  95040
agtagcaggg cttcgtacta acggcatggg acgtgttaaa gaagttaaag ttcgaatcat  95100
gcccagtttt ggcggacaag atgcccagta tgcttacgta agtcctaaat tcctggaaaa  95160
acatatacga gtccaatttg cttcaagcga agaagttgca cctgcacact ttgcttcaaa  95220
cgatatcgtt gagcctacta cacagtttaa atgggccctt tgcaaaggcg ttgaattcca  95280
gaccgataaa gaatttgatt acatcgacga atacggatat ccaagcaaaa ctgatattat  95340
gtgtggcttc attagtgacc aatgggttga agatggtgaa aagttataca atatcgtatt  95400
cttaggtgac ttccgagttg ttaaagaatc tgaaatcact cgctatgtgt ctcctcgtaa  95460
agcttaagga attattatga atattgtaaa tctctctaca ggtgattacg tatatgtatc  95520
tgttgcttct cgctctaaag ttgccgggaa gttggttgaa gttctttctg tgagtgatcc  95580
ggtttttggt cgtaaccaag ttaaagttcg tgacgccgat ggtaacattg gttacgttaa  95640
aagccaattc attgaaccag aagaaaaagc gttcaaatgg ggactatgca gatcagtttc  95700
```

tgttgaaaaa gaccatgaat tcactattgc tgcggcaact gatggaacac cgtggaaaac 95760
taagcaaatc gccggattta ttagcgaccg ttgggtagaa gatggtgtta agctttataa 95820
catcgttttc gctggacagt tcatggtagt tcctgaattc caaattaaaa aatatagccc 95880
agctgctttc gcataaagtt gtttacttct cctctggttt tgatattata accatatcaa 95940
ctagaggaga ataatatgtt agtttaccgc gtagaacgta gtttttgtac tcaacgtgaa 96000
tcattaccgg gaattgctat cgaagacggt aaagccgtca gaatttggga aacctcttgg 96060
aataaagaac ctcgctcgcc atacggttgg tcgggcaccg acaactctga agaaacatgg 96120
gagttccttg ataagcatgg aatactctca ggtaacttct accatcacgg cgacaactat 96180
aatgtcccta atcgtcctac agtaaatgaa gacaaactcc ttgaacaaaa tatcttaaga 96240
tactatagaa ttgagcacac atttgaattg agtgaagatt gggctaaagg gttctatttt 96300
ggatttgaaa gtgttgacgc ggtttatgca tggtttgatg accaggtgga tgttgaactc 96360
ttgaaagcta aaggatacta catcgcggtc tatgaagcac ctgatttcat cctcggaagt 96420
tgtcaattaa tgtttagacg ttcattggca gaacaagttg attttatttt gctaaaatga 96480
tgtacaacaa ctatggtcta tgatactata gacctatcaa aacaagagga gaatattatg 96540
aaacgtcaaa tcattaaaaa cgtaactact gattcaaaca tcgatgagtt tgaagatgtt 96600
ctgtttaatc ctgatttagt tgttgtacag aaaagctgga ccgaattttt atgctacacc 96660
gaagtggttt acgtttacga aaaactcggt gatgaaatgc ctatctatgg tatcttccgt 96720
gaaatcactg aaaacggtac aacttattgg aaggaaactt actaatggct aataaattcc 96780
gcgttaactc atggtaccaa tttatagata aacgtgccca agaagagttt attaaggacc 96840
acaccgataa tgggatttac gcacgacgtc ttggcatgga accatttaaa gtattagatg 96900
ttgaccatct tggacgtcct actaaaattt taacatctac tggcacggtt ggatacgcaa 96960
caggcggtga tattcttgat gaaaacttta tctggctctc tactagtgaa gcagagtttt 97020
ttgatgaagt gggaaatcca tatcaagcgt ccgaagagca agattctgat gaacttgacg 97080
aattgtctga atttccggtg atgacgatta ctatcgaaaa taacgaccag gcatggtctt 97140
tgtatcaaat gttgaaagcc cattttaagg aataataatg ccgttatacg actataaatg 97200
ccaatctgaa gattgcggtc atgaatatga aaaaattaaa agaatttctg aacgagaaaa 97260
cgatgtttgc cctgaatgtc atcgtttgtc tactcgtcgg gtttctgctc ctaaacatgt 97320
gaacggtggc ttttacgact tacttaagaa gggttaatta tggcttttaa aggttttgaa 97380
gttggtaaga aatatcgtat tatcaaagga caggaagata atttcttgag aattcttaat 97440
acgactggta aacgtcttaa tactaatctg catactactt tattgtccaa agattttatt 97500
gtagaagaga tgattggtta cggtgtttca atgattgctg tagaagccgt aggcgattat 97560
ggtcgaacta ttcatagtat gcaaggtgat attctgcttt atggtgcaga atttaaattc 97620
tttgaagaag ttccggaacc agatacagat gtcgatttca aaaaaggctc tatagaattt 97680
gttgatggtt cggtgatcgt atcaggcgat gtggtcatta cagttaaaag tgaacaaggg 97740
cgtttggcca caattgatgc acttcagaaa attaaattta aataagggct tcggcccttt 97800
ttgctttaga tttcggatgg tagaatacct ttatgaaata cataacatac ttaacaatat 97860
acacaggcga taggttgtca ccgttttata tagggtctac ttatcttgat aaacatgcaa 97920
acaattacta tcatggtacg gtaaagtcga aaaaatataa acaaatttat gataaagaga 97980
taaaagataa tcctcattta tttgattcat gtattattgg cgaatttgat acacgggaag 98040
aagcgacgtt ttgtgagttg tattatcaga aattgcataa tgtggttaaa tctgaaaaat 98100

```
ttttcaacat gtcttatgcc acagtcgacg ggtgctttgg tatggatgtt tcaaaagagt  98160
taaatccatt ttatggacac aatcactctg aagaaactat tgaactacaa tccgttatca  98220
agaaaggcga tcttaatccg atgtatggaa ttaagcgccc ggaacattct aaagcaatga  98280
gtggcaaaaa caacccattt tataataaga aacatacaaa ggaagcgctt ataaagtgtg  98340
ggcttaaaaa tcgtaaaagt cctgtatggg aatatgaatc tgctttatat aaattatggt  98400
tagaattgga taaaccaaag gttgggaaat ttgctaaaga aagcattaaa cgtggatttc  98460
cggaaggttc atacaaaaat atagtcatgc aatttgagag aaaatctaat gattgataat  98520
aaaattgaaa tgctatctga taaagagcat tgtttgaagc gtcctggcat gtatattgga  98580
agtgttgcca atgaagaaca agaacgtttc ctattcggtg aatttaaaaa ggttaaatat  98640
gttgcaggtg ttctcaaatt aattgatgaa attattgaca actcagtaga cgaagctatt  98700
cgaaccaatt tcaaatatgc taataaaatt tccgttagta ttgatttaaa ttctaataaa  98760
gtgactgttg aagataatgg tcgaggtatt cctcaagaaa cagttattac tcctgaagga  98820
gaagaaattc caggaccagt tgcggcgtgg acacgtacaa aagccggtgg caactttggt  98880
gacgacaaag aacgtgttac gggtggacaa aacggtgtcg gttcttcatt aacaaatatt  98940
ttttctgtct cttttgttgg cactacttca gatggtaaaa atgaattgac cgttaattgt  99000
tctaataacg ctgataatat ttcttggaaa tctaagccgt ctaaaaacaa cggtactaag  99060
gtcgagttta ttcctgattt ctcacatttt gaaatgaatc aatttgaaaa aatataccaa  99120
gatattacta tagaccggct ccaaacattg gcggtcgttt atcctggtat tgaatttaaa  99180
tttaatggca aaaagattca aggtaacttt aagaagtttg ctaaacaatt tgatgaagag  99240
accatcattc aagaacaaga cggatgctct attgccattg gacggtcacc agatggcttc  99300
cgtcatttaa cttatgtgaa taacatccat accaaaaacg gtggtcatca cattgaatgt  99360
gtgatggacg acatttgcga agaattaatt ccggctatta aacgcaaata taaaatcgac  99420
gtgactaaag cgcgcatcaa ggaatgtctc actctcttaa tgttcgttcg tggaatgaag  99480
aaccttcgtt ttgattccca aacaaaagag cgtttaacaa gtccttatgg cgaaattcgg  99540
acgcatatta aattagatac aaaaaaattg gcaaaaaata ttttgaattc tgaagcagtt  99600
ttaatgccta taattgaagc agcattagct cgtaaattgg cagcagaaaa ggctgcagaa  99660
actaaagcag ctaaaaaggc aactaaagct aaggttcata agcatattaa agctaaccaa  99720
tgtggtaaag atgcagatac gacattgttc ttaacagaag gtgattcggc aattggttat  99780
ctcattgatg ttcgtgaccg tgaactacac ggcggattcc cattacgtgg taaggtgatg  99840
aatagctggg gtatgtcata tgctgatatg atgaagaaca aagagctctt tgatatctgt  99900
gctatcacag gtcttattct tggtgaaaag gcagagaaca cgaactatcg taatattgca  99960
attatgaccg atgccgatca tgacggtctt ggaagtattt atccggcttt gcttgctttc 100020
tttagtaatt ggcctgaatt gtttgaacaa ggacgtattc gctttgttaa aacgcctgta 100080
attattgcac aaattggcaa aactcaaaaa tggttttata ctgtagctga gtatgaagaa 100140
gttaaagata cactgcctaa gcatagtatt cgatacatca agggattagg ctcccttgaa 100200
aagtcagaat atcgtgaaat gattcagaac cctgtgtacg acgtagttaa acttcctgaa 100260
aattggaaag aactctttga aatgttgatg ggtgatgatt cagaacttcg taaagaatgg 100320
atgtcctaag ctccttcggg agcttcattt taattttaat aaggcttaat tatgaaagtt 100380
atgtttatcc catctcgtgc agtcccattt aacccagaac gtgtacaagg tggtcttgaa 100440
```

gcagtacatt taaatgtgtt gaaatattta gtttctatcg gtgccgatat tgattatatt 100500
ggttttgaca atgacacgtt tggtgattgg aaggttaatc atcatcctgt tggtcatctg 100560
acaaaattca gtctaggtat gagttatact atggctcgta agattgttga actagccggc 100620
atccatgaat acgattttgt tgttactatg gaaccgacta aactaaccgt tcaggcaatt 100680
aaagacgcag gtctctctaa agttcataag aattttatgg caacaccatt tgaaccggta 100740
tctcgcggca ttgttcaaat ttgggaccag actattcaaa ttcataagaa tggtggtaag 100800
agttatgctc ctactaaagc cttccgtgaa tttgaacgta aatattgtta tatgacttca 100860
ggtctgactg acaaaattga ttatgattat tggcgagcaa atccgttgtt tgaagccgaa 100920
gattatccgg ttatttgttt gaatgagaaa cctgaagttc ttccggcgac tgatctgatt 100980
attagtgcac aacgttatga cactaaaatg cgtcgtactg atgttgctct tgaagcgatt 101040
aaagcactag gcgaaaatgg tattggttat tgtccaagca aatgggcacc accagctaaa 101100
tatcctgtta ttattgatgc tccacacagt gaaatcatgg aacgtcttaa aacagctaaa 101160
gcacttatta atacgtgtcc tgacacaggt acggtagaga atagttctat tgaagccgtc 101220
tctaaaggcg tccctgtaat ccagttagtt tttaaggatt atcctcatgc gacattcgaa 101280
tacgacccag atactgtgcg tgtagaaatt gattcctcta ctcctaagaa agaagtagtt 101340
gcgctttaca caaaagctgt attagaattc actgacacat acgaagctcg agttaaacgt 101400
gctgaagcag tatggaagaa gtataatcga gatgcagttg ttgcgatgtg ggataaaatc 101460
tttacagcgt aaatcctgaa tagcctgagg cactattaca cacaagatga tagattatat 101520
ggtctttagt aatagtgccc taggaatcta ctgaagagaa tattatgaga atatataacg 101580
tggacttgga actttttgat aaagcagtgc tccgggaatt ccggcttatc caaagatttt 101640
ttgatatcga gtcagcagag tcctttaaag aacgctttaa agaaattcga tataaaatac 101700
aaaccgatac agctactaaa gaagaacttc ttgaagtagc agaaattttt aaacgtaact 101760
tgtgatgaga gaaaaatatg attattgaaa cggctaaaga aacgattatt ggttcaggcg 101820
gtaagagcac agcatttact attcaaggca atagcaaagt ttataagatt ttgtctaatg 101880
acctttatac aaacaaagaa ttggcttgtg tacgtgaatt aatcacaaac tgtattgatg 101940
gacaaattct taatggttgc actgataagt ttattgttca ggctccaggt cgtttagacc 102000
cacgttttgt agttcgagac tttggccctg gtatgagtga tttcaccatt cgaggtaatg 102060
accaagagcc aggaatttat aactcatatt ttgcttcaac taaaacatcg agtaacgatt 102120
tcattggtgg attcggactc ggttctaaag ctccattagc atatactgat acgtttaaca 102180
ttacttctta tcataatggt gaagttcgtg gttatgtaat ttatcaagat gacagtggtc 102240
cacagattaa gccaaccttc gtagataaga tgggtcctga tgaccggacc ggcgttgaag 102300
tagttgtacc ggttaaccca gaagattttg aaaagttcgc atccgaaatt gcttatgtta 102360
tgcgtcctct cggcgatatt gcagaagttc gcggtgttaa agatatcaaa tacttcccgg 102420
aattcgatga tgtttatttg gccaaggaag ctccatgggg tgaacgtggt aatatcatgg 102480
ctgtttatgg tggtattgta tatccaatcg gaagtgttat taaagaacaa acatggatga 102540
tgacgcgatg cactacagct tatattaaat tccctatggg tgaactagat gtagccccgt 102600
ctcgtgaagc attgtcattt gataaacgta cagtagcaaa tatccataaa cgtgttgcag 102660
aaatcgatgc aaaattattt gctgaagatt ctaagaaatg gattgattgt gaatatccac 102720
gtcatgtatt ccgtgaaatc gattctcttg gttactctgc tcgtaaatac atggaaaaag 102780
ctggttctaa tattgaatca ctgaaatatt ctaaagaaca gctaacttat tctgagttgt 102840
acaaacgttt taaaatggga cctgaatggt gcaaccttgg cgttgtatat gatatcgttt 102900
cagacccacg acttcgtcgt attcgtgaaa gcggaagctc gtcttcaact atttcaatta 102960
atagcctgct aggtattagt cgtaagcata ttgatattgt tattgacgat gtgaaaggcc 103020
gcgtaccaat gatgcgtgct ctgaatgatg ctttgacttc caccgatgca tcaacactcg 103080
ttgataaggt tccttccgga tggggtagta gcgtattatt cgttaacccg gaagatgaag 103140
ttgcaatgaa acttctggaa cgattaaagg ttattttcgc tggtgatagc cttaaatttt 103200
ataagacctc tgaaattctt gcattagtta aaccgtggat tgaagttaaa gaacgttcat 103260
cgcagcctcg tcctaaatcc ccaagtgctc atcggttctt taagaatgaa aacgatgttt 103320
gggtatcaga agatctcttt attccagccg gtaaagctga tgagattcaa ggttatgttg 103380
taattcgtaa tcgttctaac gctgaatgtc ttgacgcaga taaaggttgg ttgaactatg 103440
actccaattt cttgacccgt attgctgatt tgtcaggtat taaagagttc actgtagtcc 103500
gtccacagat tgctaagaaa gttcgtaaac ttggtgaagt agaatgcttg ttcgaaaaat 103560
caattaatga ctatattacg ctaattgata aagtggatta tgatgagtat gtatcaccaa 103620
gtcgtagagc acagccttat ttgaatcata ttactcgtaa tgaagagctt aacttcctta 103680
gtaagtattt tagctctaag aacaaagaaa tcagtaaaga ttttgcaaaa ctttcaacag 103740
taaataatcg ttggggatgg aatcgattcg caggtgctac taatacagac ctgaataaga 103800
agttagaatt gtgtgctaaa attttcgata agcttaaaga taatgcttac gataatgatg 103860
ataaaatggt tattgaattc gaaaccaatt atcatattgt gtcagaatac atgggacgac 103920
gtggtactct ttcaaaagaa caggtcgctc aaatcgttaa attcatgaag gccgtggaag 103980
cggccaaata aggaaacatt atgtacaata tcaaatgctt gtcccaagaa gaacagttag 104040
aagcttacgg cctggttgaa tcaggcaaat ggactcgtaa agaaattgcc gattacttcg 104100
acatttcaac agatactctt cgtaagattg ttaagaattt taaagcagaa ggcgttgtcc 104160
ctgaagcaaa cgatgcctct tatgtaatcg aagaagttcc agaaaatgat gaacctatta 104220
tcggcggaca tcgtccagaa atcgtatgga acgcgtcatc taaatttatc tcaatcattg 104280
aaggacgcgt agcatacaat gcgactccat caagtcatgc aaattttgaa gaaattaaag 104340
ctaatttggt tgcaggaaac cttagtaaag ctgtcgaact tattaacatc aagaaagcta 104400
ttactaagtt tgttgatggt aatgttacta ttgaaggtgg tagtttattt tatcaaggta 104460
tagaaattcg ttcaggactg gttaatcgta ttattgattc tatggaaaaa ggcgaagact 104520
ttaaattcta tctgccattc cttgaaaacc tgttagaaaa cccaagcgaa aaagctgtac 104580
aacgtttatt cgacttcttg gttgcaaacg atattgaaat cactgaagac ggtcatttct 104640
atgcgtggaa agtagttcgt aaggactatt tagactgcta tagtggtaca tttgataact 104700
cacctggtaa agttgtttca atgcctcgta ctcgtgttaa cgatgatgat acacaaactt 104760
gttcccgtgg tctacatgtt tgtgctaaat catatattcg ttactttggt tctagctcag 104820
ataaagttgt taaggttaaa gttcatccac gtgatgttgt gtccatccca gttgactatg 104880
gtgatgctaa gatgcgtact tgtcgttatg aagtaatttc agacgttact gaattatttg 104940
cagaataata attggggact taggtcccct tttttcttta gaggtaaaca tgattcatcc 105000
atttgacgta tcagaatcca aaattgctaa tcttcgtggt catcataagt gtaaatcagt 105060
ttattgcgct aaattggtaa aacatcctgg cgatgcacac tacggctggt tagaatgtga 105120
cgaagttgtt attgaaattc cgcctgtaga tgcagaatat cttgaagaag gtgaccgcat 105180
ttattttggc gaactacaca tcagaggtgt atatggtaaa gacgaacttg ggactgttga 105240
gactgaagaa tcttccgaca tttatcctgt cgaatgagtt tttgactagt gaaatgaagg 105300
tgaagattgc tgacactgct cggtattccc tgagccaaaa tcctgaccaa aacaaagaag 105360
atgtagttcg acgttgtaag gttgcggtct ttgcagagta tgtagtagca aattggctag 105420
acggatatgt taataaaggt attgaagacg tagaagaccc gtacacgtat gcatgggacg 105480
tgttagccca tcccaagtat tgtggaattc gtgtagaagt caagacacac cagatagatt 105540
ctaaatggat ttctgttacc acaggataca gtggtgatta tccaggtggc aacggaatca 105600
acatagggcc cttcttgaac catcgagtcg cagattgcat tattatatta gatgtcaaag 105660
aaacctcacc tgacgtcttc tcttattcta taaagttcgt gggagaccat gaagacctaa 105720
agaaaatcgt ccgcaagagc aactacaacg ggtggtatct tcaactttaa tttcataaaa 105780
gtgtttacaa ctaagtagga ctatgatata gtagtcctat ctaaaagagg ataacatcat 105840
gaaatttaaa tttttctacg caaaacacaa agtaacaggc gaatttgttt caatgtacaa 105900
cactgcagat gacgaaggga tgatttatac tcatttgggt ctatctcatt gggactcaga 105960
cgtgccttat atgtcatctg aagccgaaat aactcgtctg gttaatggac atatgaacga 106020
ccattttagt gttattcttt ctaaagacct taaagaggtt atcaacaaag gatatatgga 106080
actcgcggaa gttgagatat gagctctaaa atgtggatcg gaatatggtt gcttagtatc 106140
ccaatgattt gtatagtatt ttcaattgta ttgaggtact tatgaaaaat gcacttatta 106200
ttgtactaag aacaatttgt gatacgggtt tttacatcgc atgttcgttc actggaacat 106260
ggttggcttt aacatatttt aatgtaattt aactgtttac atcaaggtag gattatggta 106320
tagtagtcct actgaaacac gaggaacaca aaatggctaa gctttttaaa gatgttgaaa 106380
ttggtgaaaa atttgttctg aataatggtc agcagcttat tcgtgtagct tctatcgccg 106440
gacaaactca taactgtatc gccccaacgt gttggactcg attctttatt gaagatgaca 106500
ctgaatgttt aactgttgaa gagctttttg aacgttctga tataaccgaa taaaattgta 106560
caaactcttg agagcagagt ataatgctct catggattac aaaaacatta atcaattgag 106620
gaaattagca tgtccaaata tttaactcgt aaagaccttc tggcagttgg tggtgaagtt 106680
gttgcagtag ttcgtaatgg cgaatacggt tctgaagttt ctaaagagtt tcgttctcgt 106740
gaaggttttt acttctttgt taaaggttca tctgactggc gtcaagtagc agcacgattc 106800
tttgtaggac gtcaacgttc taaacaaggg ttggatgcaa ttctttctca cattcgtcaa 106860
ggccgttcgc aactagcccg taccatgggc actaacaata ttgaatatga tgtaatcttt 106920
gttgcagcta agaacatgaa acccctgact actggttatg gtaaaggaca attggctctg 106980
gcattcactc gcaatcatac atcagaatat caaacactca ctgaaatgaa ccgtcttctg 107040
gcagataatt tcaaattcat tctgcagagt tattaattta tataggccta ttaagttggg 107100
cctttaattt atttgtgagg taattaaaat ggtagcatgg attattgcat tgctgtgttg 107160
gtcgttttta ttcgttaaca ctttagttac aggcgaaaca acagtatttc aacaggcggt 107220
atcacaaggt accttagcgg tcttagctct tcttaacgtg ttaaaggcga gcaatgatta 107280
agaaaatctt agcaggagcc ttcgggctct tgttgttgct tactgttctg tactacggtg 107340
tgatgtttgg gctaatccaa gtagtgcttt tcatttcgga tgttataatg gttattcgtt 107400
cattagtatg gtgaaaatat gcaattgaat tctcgtaatc taaaaagtat tattgataac 107460
gaagccttag catatgcgat gtacaccgtt gaaaaccgtg caatcccaaa catgattgat 107520
ggatttaagc cggttcaacg ttttgtggtt catcgtgcgt tagatttggc tcgtggtaat 107580
aaagaaaaat ttcataaact tgcgtcaatt gcaggtggtg ttgcagattt aggttatcac 107640
catggtgaat cttctgcaca agatgcaggt gcattgatgg ctaacacgtg gaacaacaac 107700
tatccactgt tagatggcca aggcaacttt ggttctagaa cagtccaaaa agctgcagca 107760
tctcgttata tttttgctcg tgtaagtaaa aatttctata acgtatataa agatactgaa 107820
tatgctccag ctcatgaaga taaagaacac attccaccaa aattctatct tcctattatt 107880
ccgacagttc ttttgaacgg cgtctctggt attgcaaccg gtcacgcaac aaatattctg 107940
cctcatagtt ttaaatcggt aaaaaaggct gtattacaag ctcttcaagg taaaaatgtc 108000
actaagccaa aagttgaatt cccggaattc cgtggtgaag tacatgaagt tgatgggcgt 108060
tatgagattc acggaacata taagttcaca tctcgcactc aaatgcagat aactgaaatc 108120
ccatataaat tcgaccgtga aacgtatgtg agtaaggttc ttgacccgtt ggaagacaaa 108180
ggtctaatct catgggaaga tgattgcggt gaacacggct ttgggtttaa ggtgaagttc 108240
cgtaaagagt actcgcttcc tgatgatgaa gagctacgtc atgaaaaaat catgaaagat 108300
tttagtctca tcgaacgtcg ttcacaaaac atcacagtga ttaatgaaaa gggtaaatta 108360
gcggtctacg ataacgtagt ggacttaatc aaagattttg ttgaagtccg taagacttac 108420
gttcagaaac gtattgacaa caaaatcctt gaatctgaaa aagcatttaa acttgctttt 108480
gctaaggcac acttcatcaa aaaagttatt agcggtgaaa ttgtgattca aggcaagacc 108540
cgtaaagctt tgactgaaga gctagcacaa atcgaaatgt acaaagaaca tgtcgataaa 108600
ctggtgggtc ttaacatctt ccatatcact tccgatgaag cacgtaaact agcagaagaa 108660
gctaaagcta agaaagaaga aaatgagtat tggaagtcta ctgatgttgt gacagagtac 108720
actaaagact tggaggcact ttgagtgccc tagccttagg atttctcggt gcaatagctg 108780
cactagtgat ttggctgtat tggttggaca aacatgatta gggagccgaa gctccctttt 108840
gtgcattttt tctcacaaaa cagtttacat gcgcttcaaa catgatatta tagacctatc 108900
aaaacaaata ctaatttgga gaaataaaat gtctaaagtt acttacatca tcaaagcttc 108960
tgaaaacgct ctgaatgaaa aactgctgc aataatggtt tatatcatta agaacaactt 109020
caccactgct gccaatgtcc gtgaagctct ggaagcggaa tacaatgcat cggttgtcaa 109080
ctctaacatt ggtgtattga ttaagaaagg tttagtcgaa aaatccggtg atggacttat 109140
agcaacaggc gaagcaatgg atattatcca aaaagctgcg gacctctttg cccaagaaaa 109200
tgctccagaa cttcttcaga aacgtaacac tagaaaagca cgtggagtta ctcctgaaat 109260
gcatgaatta gcaaactttg tttttgaaaa cattaaagat aaagttgaag ttaaagaaat 109320
tggtgaaaac cgtagtaact tagaagttcg atttgcaaaa cgagttctag gtattcgtca 109380
gatcgaaatt cgtcgaaatg gttctcttag aatctttgca tacaacatgt cagaaactga 109440
atcaaagctg tttacttctc ttgaaaatga tgttaaaatt aagatcggtg gtaaatatac 109500
ttacattgac ttccctaatg tgtccaaaga aatcattacc cttgtaacta acgtactgtg 109560
aggaatacat aatgaataag ctgaatatta ttaacgaact tcgtaaatgt gcagaaccta 109620
ctcaggaagg atgggatatt tggtaccatg gagcttatct tggaactatc gttaaagtta 109680
gagctgggtt atatttaatt attcgcgaaa attccgaatt ccctaatgga gtagctcctg 109740
gtggtataca taaaaacttt atggcagcga tcagttcatt tgttgatgca gcttacgaaa 109800
tctataaaga agattataaa gaatatcagc agtcacaacc ggttattcgt tcgatcggtg 109860
taaataaaca agaacaaaaa tctatttggc aacgtattaa ggaatggttt aaatgaaatc 109920

-continued

```
atttaaagaa cgtttagagc tattagattt ggccttgtct cgtgagactc ctgaaagtct 109980
agcagaaaaa ttccagtcct atggttataa ttattctgct gatgatataa tgaatgaagt 110040
tcctgaaatc tgttggcaaa cgtgttattg gaataatgac caaaaagttc aacgtgttat 110100
agtatgtgca gctaataggt ttaaattgaa gagcggtgga actctggtta ttcctggagt 110160
tcgtcattac tctaaagata tggctgaagt acttgatata gttggtcctc aattagtctc 110220
gcaacaagtt tgtggtgacg atcaaggctt tatcgaccaa tactctaatt actggactcg 110280
tgaagaagca atggttattg caacgtatgc tggacaggta cgtattgaac gtggcggaag 110340
cgagaaagaa ctttattcag aggaccttta ttaatgaata ttaaacaact ccagaaagat 110400
gctattgaat cacgcatcca agatatcaaa cgtcttaatc atatgatgga agaaaactat 110460
ggtatgtatg ctaatcagcc tggttgggac gctttagacc atccttattt ggttaattta 110520
tgtaaaggtg atacgttagc aattattcgt gatgggttaa aacctttctt gcgtgacatg 110580
tatattaaaa tgaacgaaga aattattagc tcgttgcaat atcaattaag gaaattagac 110640
gatgagaata attgattcta aagcagatta ttttaattcc gttaatgata agaataaagc 110700
tttaattcgc cactttatta ctgagatggg atataccgac tctaaagatt tgaaagagca 110760
cattatcgaa tgttctgtgg ctaaaaagtt ttcttttacc gataaatgtc taaatgaggt 110820
tataaatcat tatgaacaat cttgtagcaa aacatgattt caataaggct tccgtccata 110880
aggacaagaa gaaatcagaa cttcaatcta aacgtaaaca aaaacataag ggtaaagact 110940
atgcttacta aaatcaaaga aaatcctgcc actgaacttg ttattcgttg tgaagaactc 111000
gcagagcttt atcaggttaa ccgagaagta tatcgtagtg ttgttgcaga tatggcagac 111060
gaagtatgtt ctcgtattcc ttttagtgtt gatttcaatc acatgaagcc tggtgaaatc 111120
actatcgtct ttggttctga ctatactgaa gaacgggctc ttaatgccct agaatatgaa 111180
atgtcattct ttgacataca ggactacatt gatagttata aggaacgata tgagtcataa 111240
tcttcagaac gtagtagagg ccgaacgtga gcgtgaggct ttagtctata atgaactatt 111300
agttccgttc ttggccttac actcgtacga acaggaagac tataccaatt acgttaaaag 111360
cgtagaaaaa gccgtttaca atcaacactg ataatggtac tatatccata tcaactaagt 111420
ggaatgaata aaacgttatg aataaagaca ttgaaatcgt acgtgaaatt attactattg 111480
cttctatttt gattaaattc tctagggaag atattgttga agaccgagca agtttcatcg 111540
gattcttgaa tgagattgga attaaaaaag atggtcggca gctaaatcag aattcgttca 111600
gaaaactaat tacaaattta actgccgaag aaaagaaaac actgattagt gaattcaatg 111660
aaggttttga aaatatttat cgtcatttag cgatgtattc taacaactaa ttatttagcc 111720
cttcctagta ttcggaccgc ttggttgcat atagcagcta agcgatcttc ctcaagtata 111780
ttactcccct tataccaata catcgtcaca gttccagcat agatgttatc caaattaaag 111840
tatgggcaac tatacatata agaaagttcg gcagtcttag attttgtagg caaaaatgca 111900
aattctgatt tagatgagaa atgacggcca cttaaatgaa ttatatattc attggccgtt 111960
ttatccaccg ggaatccacc aagggacttt tcagaaattg tgctaggtag tttgccttca 112020
taagctataa ggtcgacaaa ataatttaag tttttaggtc tgaaagaata cacagcacta 112080
aaatctgcac cagatgagat atgaactatt tgcagttgtt ctagagccgc agattcaaaa 112140
cgtaaagctc gttctttttg gattatttca gtataagtat catacttagc tcttacataa 112200
taatccagca aaatacttcc tttgtaccat attagtgcca ttaggaacaa aagaataatt 112260
accgctactc gtgacattaa aacctttcca gtagcgttat ctttgaaaat acgatctagc 112320
```

aacccaaata gaatatcact aggtgaaaat gacacttttg gtgttgccat aatacctcct 112380
tacttaaaga tatttataat cgctttgaaa atagatttgt tttcaaggtc agggaattta 112440
gggaattcgc cgccaagatg ttcatgtttt tctaaaaggg caaagaattt tttgagctct 112500
ttaaattttc gtttttcttc tctattagca acctctgcgt caataagaga acttaaaaca 112560
ccgaataatt tatagagttc atgaattttc ttatcacgtt gaactacgcg tttatatgct 112620
tcatcttcct tccacccggc gtcggtccaa atgtcaaatt caccgggttc ttctgtagta 112680
acattttgaa gagcacctag agtgtcaata acaatttttt gcttatcata agtccatact 112740
gtttttccgc gatggtcttc aacatatacc cattctttct cgcgttcgtc aaatataaca 112800
gcatagcctt ctttagggtc taaaggtttt tttggtgtcg aatgagccgg aaatcctacg 112860
ccttttaatg gtttataatt ttcttctttg taaaattctt tagtgtcaaa ataatagtga 112920
tagagtttca tattataaaa agggaccgaa gtcccttctc cttatgctaa acgaacgata 112980
tagttaaaag caatgttttt aaccgtgttt tctgtattac ctgtactatt tatggtaatg 113040
gtatgcccat gtgaaccaat tgctactgaa tgggtgtgag agccgatacc tactgaatgg 113100
ctatgggcac cgatacctac agtatgtgcg tggttacctg tggtgctagt agtaccggac 113160
caactatggg tatggttacc ttctgttgac gactttgcaa tatattggcc tataccaggc 113220
acaatacggt cgcttgtggc aaaagaaaga acattggttc cactaattgc agtagctcca 113280
ttaggatata ctcctgttgg ttgattatta ggaccccttg gaccggtctg tgagtgctgg 113340
tggttacctg cagcacttgt agtaccgctt actgtatggt tatggttacc agtggtatta 113400
ctggtcttag taccatagtc gaagctactt gtcatcttag taccataatc aaagcttgat 113460
gtggttttag tacccaaatc agtattagat gcagatgcgc cgtggttatg agacttaata 113520
ccatcagctt ctgcactcaa cactgcgcgg ccactcggtt tacccttgat agtttgtcca 113580
cgcatatcag gaatagtacc tgtaggatat gcgatagcga gcttaggata agctgaagta 113640
tcaaaagtct gaccttccat tatggcataa ccttcaggag gtgtatcagt aggccaagga 113700
atcggagcac caataggata acttgagaca atatccgtct taaggttatt tattgtggta 113760
ttcaagttag caaaattacc agaaccaccg gtgatattac catcagtacc aaaagtggca 113820
gcaccggcaa taattttacc agcagcacgg aaatcaccgg tgcgacggaa ttcccaactt 113880
aaatcagtgc caccagtact ggtgccttgg tggtaatgaa cacggaaatc tccttgatta 113940
attaatgtcc caatagaata agtgctatca ccttgcacat aacgctgttt aacaatagga 114000
atatattcag aagtagcagt acgctctata ttcatataaa ttggagctct ggcgtttacg 114060
tcattctgag atgcaaacga accacaacct gctgggcgaa ctccatcaga agcctcaata 114120
tctatataag cattttgtcc taattgcata cggtaattag gagaaatgcg actattacta 114180
gtaacaacaa caagtttgtt atcgttgtcc acagtaatca tattaccgcc agcgccatca 114240
tcgcctaacg tgacagaatg tcgcatttgc accataccat tattaaggct aatactaagt 114300
gggcggagat tacttattcc accgctttca ccggcatctt taggagttgg gataaatatgc 114360 aaagatgatt ctgaacgacg gaaaatggca ccatattcag cattccaaat tcttaatgca 114420
tcagcagttc cgccaaattt agcttgacca tttacagata atccattatc agcattcagg 114480
gaagatcttg ttgtaataga accagaagtt aataaactac cggccatcgc aaattcaaca 114540
gaaccgacag tagaacctgc tgcaggagca acgcgttgtg aataaaaatg ccaaccctgt 114600
ccatcgccta attcaaatac agtttctctg tttttattag tgttatcctc aaatgcattg 114660

```
ccccatgctt tcatggtcac atagcttttg ttctgacccg ggcgggtgcc tgcgttccat 114720
cgtattatct tagttccatt tatagaagaa gaagcgccaa atttaagacc ggcgttagaa 114780
gaactactat taaagaataa cccattatta agcttaactt cttgagtaga tgcaacagta 114840
ccatcagcac gcaaatttaa tgaatttgaa ccagttttaa tatctaaaat tcctggttca 114900
acaataagtc cttcggccat tccaatggcc attcttcctc tgcctctaaa ataatgataa 114960
aatttaccat tactattata gccaatatgt gtctgaccat ctccgttatt attttggtca 115020
acttcagtac gaactgaaag aagagctgcg ttctggccag gaagaagcca cgtaccacct 115080
tggtcttctg agcgaccaaa tataccttta cgagtactac ggaaactatc aggcgtaata 115140
gatgcaacgg aataacctcc accaactaaa tcataaacac cttgtttaat atatttcaga 115200
ccagttacag tgtcaccgag aacaagatac ttatcaccca ttaccccagt atttccataa 115260
tcactagacg ggaaacccgt agtgaatgta cctaatgcaa ggctattacg gccagctatt 115320
cggccatcat tacgaatacc atattgttta gattgaggag tattaccagt ccaccatgac 115380
atttcatcag cttgtccagt ctgagctgta cagatttcat gccacatagt gccgccagat 115440
ttagcacgaa ctttacgaag atagtttact ccgttagttt caccggttcc aggataaaca 115500
tactgaacca atgattgtga atcgtattgt ccgaatgctt ttgtatctaa aataatattt 115560
ttagtattaa tttgaggtga agtaatattt ccaatagctg caatatttcc agatgtagtt 115620
atactacctc ctgatactgt taaacctcct gtatcaacaa caaatccacc gtcacgtcga 115680
aacgtccaat atttcgaatc gccagattca ttaatataat gaatcttcaa cgaaccttca 115740
gaaactaaag tacctaatga aaaagttcca tctttaaagc gctgcttaat tataggatta 115800
tattcagatg tggaaagagc tgagctcaaa tctacaaaaa ttggggcttt tgcagcatgt 115860
tgaccggccc aagccccact tccagtagta cgataattaa actcaatata tccaccgctt 115920
gctacaattt gcggaccaat taaattaaat tttccagtct gtgtataatc accggtttga 115980
gtgatatttc cactgatatt accgccagca gaaatgctta aatcaatgat atttcccgaa 116040
tcgtctttag taaaaattgt tctatctttt aagtttatag ccaattcacc ttcggctaat 116100
actgaagcag caggacgtgc acctgctatt ttgcttcttt taaattgtat ttgttttaaa 116160
gtagccataa gtcctcttaa taatagccga aatcttgaac agaatcctta attacgattt 116220
ggtcaaatcg tggaacatgt gaaggttgag atgcaggatt ctgcgagaaa aagtttggtg 116280
ctgttaaagt accagtcatg gtatcgcctt tacgcaatac acgggaattt gcgttatccg 116340
taacaatatt tattcgtcca tcaacataat cttttcttgt gagatcattt gctgcaaccg 116400
gagcaactgc attagttctt atttgaccta ctgctgtcac aacgcctttt gtactaatat 116460
caccattacg tgcattaatt acaacagttc ggtctgctga accttgtgat gacttaaaac 116520
caataccatt ccatgaaacg atgtcaatat ttgccatagc aaaagtagct gcatcaccgt 116580
tacctggata aacaccacac tgttgactac tacctatagt aggaacatgt acgcctccat 116640
taaatcgaac ggtcgcggcg taagtaccac cattagcttt agaaacgaaa tcgttatcag 116700
ccgcttgtgg tttattatat tctgaataga gtttaaacgt tttatacagg acgtcatcac 116760
ctgctggcat taaagggaaa ttaccttggt gccatataac agcgccgcca gttgtactac 116820
cagcttttaa atcggccata gttgtctcct tatatgtata ccatatttat acaaaaatgg 116880
gagacttcgg tctccctaaa tttattctga tgcttcttta aattcttgtc caaatacctt 116940
accagtatca gttgaagatt gagtaggtaa tgtcattatg tctggggcac ttaaagattc 117000
tgaaacataa tttacacgaa taccatttat accaaactcc gcaggttttg aaacgcttcc 117060
```

```
attgcatgat acttcagtga atataacgtt tcttaatcca ccttgcccga ctggagctgt 117120
acgataacaa taaatcgtga acccgtcagc accagcagga atttctatgt agtcttcata 117180
tatcttccat tcacctgcac ccccatcaaa gtttatatcc ttaaatgaaa taggtgaagt 117240
agaaggagat ttaaagaaac gaatagaaag tcgtgtcgtc ccttgtgcta acaaatcagc 117300
atcggccatt agttggaatt tcatataaag gaaatctcca gccttcaatt tatacccagc 117360
gagaggtgta ataagggatg ttgtaggcat ccttttaatt tcgttattag tacctccaac 117420
agcagataaa aatgtgtctg acgattcgta cgtacgacta gggaagccgg tagcaccaat 117480
atcatcgatc gtgtcgtaca caacatcaag tggtgtacta tagtcggttg aagttttctt 117540
attactatac ttaatatgtt ctagtgctat agcattctta ccagaaatat aaaatgctga 117600
ataagaaatg tccactatat ttaaaacttg ttgagctaat ggaataacag aactcccagc 117660
tttagtaaac catgcgagaa cttcgggtgg aaagtttgtt ttagcattag taacaagagc 117720
aaatataaaa tttgaagcgt atgtgtccat gtaagtaacg aatgcgcttg acgtggcgtc 117780
gttttcagta gagaaattat atgtcttaga ttcaactact gcacctgttg taggatttat 117840
tacacgaacg tttaatccaa cggaaaaaac ctgggaccca agtggattat cttggaactt 117900
aatataagca ggagatgttg atagcgggca agagcccgct atgcttaatt taaatcgtac 117960
tgaattgctt tccgataaaa atggcgtttg gacgtatcct tgtccaaact tagccataaa 118020
tttttccata atacctctta ttcaatccac tcgaatttaa cagatttatt cacagggtct 118080
ggaataacgc ggacattacc aatccttaag aaatcccgta ttgtcaagtt tccgattgtt 118140
gcattatcag aaggtaaagc accaatatca gatggctgag gagggtttcc accatcaaac 118200
acctgaacaa aacttgacca agaattttta gttttctgcc atgtacgtgt ccagcgagtg 118260
gtacgtgcat ctggagttgt tggataagta atccaatctt ggtaaagtga atcaagagta 118320
ttgccaaatt gagtcaaagt accaggagat ttaacttctt caccacgttc taagtatgga 118380
agtccagaca cttcattagt tttttcaacc attttaaaat aacccgggaa ctggttataa 118440
gtggctgaat cgttaatatc gattgaccag aatccgactg tatcagcagt aggagcacga 118500
gtgtataaat cagcagtttt agaaccctga gaacgaattc tcgagttaac agttaaaccg 118560
ccagaattta tagtagcacc tttggcaatg attaaacctt caccaatcgt tacttggccg 118620
gatgcattat taatagctaa aggacgtaat ccattaaatc cgccagtctg atcgcctgat 118680
gcagtgagca taaaataggt attagcagca tcattacgaa taaagaatcc gtaatcacca 118740
ctaattgctc tgaaagcatt tgcagactta ctaatgaatt cgccattagc agtaactgaa 118800
cgaccgaatg ttgcaacgcc attaacattc atcaaaccag aagcattaat gtttattggc 118860
atcacagtac cattaatgct aaacgctata ttcccatctt tattacgttg agaataaaaa 118920
tgattagatg tttcatcacc aacttcaaat acagtagaac gtgttgtatc tgatccgcca 118980
ccaaactgat ttccccaaac tctgatagtc atcgtctgtg ctggattagt tccagtttga 119040
ggtcctttct caaaaatcag acgagttgcc gttccagtat tagaaatagt taatgtacta 119100
tttgccgaaa ctgacccacc aaacgtagca gtactagatg atacaagagg ggcactcagg 119160
ttagtttgtt tagtaagact taaagaacca ttaaccgtct gtgcaatatc cctacgaatg 119220
aactgagatg aatctagacc atccaataaa tttgcgtcag cagcttttgc ttttaatggc 119280
aaataatttg ctaatacacg gtttaattca tatggagaaa tagcataact atttttctcg 119340
taaagattca gatcctgggt actaccttga gtatcgtcac caacgaatgt aatagaaccg 119400
```

-continued

```
gatgaagttt taacgaatcc gcgaattgct gtagtagcag cccatgttgg ttcattctgg 119460
acagtccatt ttaaattctt aggcgataca gcagtattag cagaagttcc tgttacagtt 119520
tcagcccgag tagcaacctt aattacacct tcagacgttt cagtggactt agtccctaaa 119580
agctttttag gagtaataag aacatcatct aaagttcctg cattagattc tgcctgggtc 119640
gctactcgaa gtgtaccacg ttgtgtttca tttgctttag aaatatcaag agtataatgg 119700
ttccacaagg ttccttcttc aataagtccg gaatcagaat taacactggt acggtcagaa 119760
gaatcaaaat gagttttaat tttcagcgga gtcgagatac gagtatcatc agttccagta 119820
tcaaattcaa cttgcgtagc aatttcagct atgccggata atccttccgt agctttccta 119880
tcatttaacg tcttaggcgt tactgctcta gtataatcag tcccagcatt agtttctgct 119940
tgcgtagcaa tttcaattaa gccaatacgt ccatcagtag aagttttctt atgtagtgtt 120000
tcaggagtta ctacagcgtg agaataacct gcttgggatt gaccagcaat tacttcacta 120060
tcaatagcta aaattactgc accttgttgg gcgtaagttg ctttatattg gtcaagggct 120120
ttaggagaaa tagttaaatt atttacggtt ttattataaa cattagtgcc tgcagcccca 120180
cgagtttcag caggagtagc agaagtagtc gatacatatt taactatacc agacagcgtt 120240
tcagagccct gacgtgcctg caatttctta ggtgtaataa tcgttgtgtc atcaagacca 120300
gcatcggttt cagcctgagt agcaatttca gcaagaccgc gacgagtttc agttgctgta 120360
cgctcattta gtttttaggg cgtaacaata gtatcgtcca caaatgatgc tgtggaattc 120420
tggttaactt gtgctgttgt agcaatttta gcgataccac gtcgagcttc agttgctgta 120480
cgatttgcca acgtttcagg agtaatagca acttctttag ctggagtatt ctctaaatca 120540
acatttgctt gcgcttgagt agcaagagca ataacaccta aacgagctcg tgtagcatca 120600
gatccagcat caacacgttc taccgtaggg acattctgtt gcacaaccca ataatgagtg 120660
tcagaatcgg tgtcttcgat atacgctaat tctaatacag gaacatatga agtagtgcca 120720
ttgaattcta gttcagtaac agagacccat tgagcatcag gtggatattc agaacgttta 120780
gggaactgaa gcaatgcaac agaagaagca attgtatcac cttcggccgc tttaattttt 120840
actgtttggc ctttacgcat gtagttcatt gaaattttaa cagtgtcacc actcaaaatt 120900
ccggtaggca gcgtaagatt aatagttccg gttgtagcgt tatttgtgcc aaaaataaga 120960
acttcttcat ttggacgaat atttgaatcc gcacggataa tacgaagacg cgatttctgg 121020
tcgccttccc atatacgcca taaactactt gcagcatcaa aaacaaaaaa cgcgtcagag 121080
tcatttctgc cttcggcaat atgagtcccg acttcaccaa tagacgttgt atcatcaaat 121140
gttttaacaa ttgtatgata cagtgggttt aatctatcta aatcgactag gctgattata 121200
tcaccattgt tagcattacg tggaagtgta atgttgattg gtgctgcact agtaaaacga 121260
cgaacgataa aatcatttgc ttgtgcttga tatggtgccg caggtgtaac agtgattgat 121320
tctttaccgt aatcaatgat atacatctgc cacaaacgat tactaaacac aaacactaac 121380
tgtgaacgtg gtcgcgtcat taaaactgta cgaacttgtt cacctctaaa gtttaaaata 121440
ctctgcacag acgcgttaat ctgtacttta actgtcccgg ttcttccacc aatatcagcc 121500
aaaacaacag tatcaccatc aaccggcgca tttggcaatg tgaaaaccat atcattgcca 121560
gcaccagtgt taaccgaaat agattcacct gaagaaagtt gataagtccc agaagcgaca 121620
gttatccatt gtgcatcggt acgaactgca cgccattgta aaaggttaaa tgccccggaa 121680
ggagacacga tatcatttat tgcttgatat aaacggttgt cataaagaac aacaaatcct 121740
ttgttatatc cacgcgtaga atcatatact tgaacggtgt tttcttgtac caggaagtca 121800
```

acgtttacgc catcagtacc tactgtacgg tcggctaatg ctacgttaac aatcttgtcg 121860
ccaccggcgt ccagaccgtc ttcggctctg aacttacgtt tgatgtcggc cattcgtttt 121920
tcctttattg tttcaataat acttatttat accagtttac gctttcaaat gagtatgtta 121980
ctatagtcaa gttgactaac tgaacaagag gttcatatgg atttagaaat gatgttggat 122040
gaagattaca aagaaggtat tgcacttgcc gactttagta acattgcatt ggcagccgca 122100
ttaaacaact ttgaagatgg cgataaaatt actgttccga tggttcgcca tgtaatcttg 122160
aattcaattc gtaaaaacgt agtgatgttc cgtaagcaag gctatacaaa atttgtattg 122220
tgtatggata atgctacttc aggttattgg cgtcgtgact ttgcttacta ttacaagaaa 122280
aatcgtaaaa ccgatcgtga agcttcaaag tgggattggg aaggatattt tactgcactc 122340
cgtcaagttg ttgatgagat taagaaatac atgccgtacg ttgtaatgga tattgacaag 122400
tatgaagcgg atgaccatat cggtgtatta actaaatatt tgtcattagc tggacataag 122460
gtatgtattg ttgcatcaga tggtgacttt acacaattac acaaatatcc taacgttaaa 122520
cagtggtcac caccacagaa aaaatgggtt aaaattaaga acggttctgc cgaaattgat 122580
tgcatgacta aaattcttaa aggtgaccgt aaggatggtg ttgcatctgt tcgagttcgt 122640
ggcgacttct ggtttaccag agttgacggt gaacgaactc cgagcatgaa aacaacgatt 122700
attgaagcaa ttgccaatga ccgttctcaa gctgaagtat tattaagtgc agaagaatat 122760
aaacggtacc aagaaaattt ggttctcatt gattttgatt atatccctga taatattgct 122820
tcaaccatta tagagtatta taactcatat aaaccacaac ctaaaggcaa gatttattca 122880
tactttgtaa aatctggtct ttctaaatta acaagtgtaa ttaacgaatt ctgaggtaaa 122940
catggctaag aaagaagcag ttgaatttaa tcaagatgtg catggtgaag aactggctaa 123000
actagtcaag gaagcttctg ataacaaact taaaatttct ggttataatg aactgattaa 123060
agacattcgt actcgtgcta aagaagagct tggcgtcgat ggaaaaatgt ttaatcgttt 123120
gttagctctt tatcataaag acgctcgtga ccaatttgaa gctgaaaacg aagaggtagt 123180
cgagctttat gacacagttt tcactaagtg atattaaacc ggttgatgag gccggtttat 123240
ctgaacaaga attagcagta aaacacgata aagatgatat cgctaaattg cttgaccgac 123300
aagaaaatgg attcattatc gaatccatgg ttgaacgatt tggtatgtct tatttagaag 123360
caacaactgc tttcttggaa gaaaattcta ttccagaaac acaatttgct aaatttattc 123420
ctacaggaat tgttgaaaaa attacaagcg aagcaattga cgaaaacatg cttcgcccat 123480
cagttgctcg tggtgaaaaa actaatacgt tagatttctt attatgaaat acgttgtgta 123540
taaaactacc aataaaataa atggtaaaat ttatataggc gtacacaaaa aacataaaga 123600
gaaagattgg tatattggat caggccgcgc tatattagcg gccaaagcta aatatggact 123660
aaaaaatttt tataccgaaa ttctttatga atatgataat gacaaggacg cctataaaaa 123720
agaagcagaa ttggttaatg aagattttgt tttgcgaact gatacttata acttagttcc 123780
gggtggtaaa ggtggccctg gtaaaaaaca aagtgatgaa gctaaaaggg ctatttcact 123840
ttctaaatta ggtaaaccta gatctgaaga gactaaggct aaagtatcta aaaccagatt 123900
agaaagaaaa ataccatccc ctaataaggg taagaaacta tctgaagctc ataaattagc 123960
tttgagtaaa gtccgaaaag ggcgaaaaac gaataagccg atgcctgatt caaccaaaga 124020
agctcttaga atagcaaatt caaagccaca ttctaaagaa agaactatta aaaaacaaaa 124080
acctataatt attgatggta taaaatactc atcatgcaca gaagtttcgg atgtttttaa 124140
tatttctgca tctctagtta cgtatagact taaatcttca aaatggcctg gatggaacta 124200
tgattaaaat acgcatgcct cctgacggag aacgttatat taacggtaaa tcagtatata 124260
aactatactt gatgtgcaaa aaccactttg gtggtcggta tgacgtaatc aaatataact 124320
ggtgcatgcg tgtttcggat aatgcgtatc aaaaacgccg agataaatat ttctttgaaa 124380
aactagcaga gaaatataaa ttgaaggaac tcaccttgat attcataagc aacttagttg 124440
ctaaccaaga cgcatggatt ggtgagatat cagacgctga tgcattagtt ttctataggg 124500
aatatattgg acgtctcaaa caagccaagg agacgtttgc tgaagatgta cgtaacatct 124560
actatttcag taagaaagtt gaagttagtg cgcttcaaga gatatttgat tataataaca 124620
acgttcagtc gagctacata ttcaaattgc tacaaagcaa tataatttca tttgagactt 124680
tcttattgtt ggactcattt ttgaatatta tagataagca cgacgaactc accgataact 124740
tagtctggca aaattattct accaaattaa aggcatatcg aaaaatactt caaatcgatg 124800
gaaatgctgc taagaaattg ttcatagaaa caatcaaatc atgtaagtat taagctttat 124860
ttcttgtgtg ttaaaattac tttataaata aatcatacca gctacgaggt ataagtgtcg 124920
tagcaaccaa ctgtaaaatt taattaataa tctaaataaa ggcaaataaa atgtttaaac 124980
gtaaaagtac cgcagacctc gcagctcaga tggctaaact gaatggtaac aaaggtttct 125040
cttcagaaga taaaggtgaa tggaagctga aactcgatgc atccggtaat ggtcaagcgg 125100
taattcgttt cctgccggca aaaacagatg acgcacttcc atttgcaatt cttgttaacc 125160
atgggttcaa gaaaaatggt aaatggtata ttgaaacctg ttcatctaca catggtgatt 125220
atgactcttg tccggtatgt cagtacatta gtaaaaatga cctgtacaat acaaacaaaa 125280
cagaatattc tcaactgaaa cgtaaaactt cttattgggc taatatcctg gttgttaaag 125340
acccacaagc tccagataat gaaggtaaag tattcaaata tcgtttcggt aaaaagattt 125400
gggacaaaat caatgcgatg attgcagtcg atactgaaat gggtgaaact cctgttgatg 125460
taacttgccc atgggaaggt gctaactttg tgctgaaagt taaacaggtt tctggtttca 125520
gtaactacga cgaatctaaa ttcttgggtc aatctgaaat tcctcgtatt aatgacgaag 125580
cattccagaa agaactatat gaccagatgg tagaccttac tactttgacg gctaaagacc 125640
agttcaaatc ctttgaaaaa ttaaatgaat ctttcgctaa ggttcttggt actgccgctc 125700
tgggcggtgc agcagctgcc gcagcttctg ttgcagataa agttgcttct gaccttgacg 125760
attttgataa agacatggaa gcctttagtt ctgcaaaaac tgaagatgac ttcatgagtt 125820
cctcgtcttc tgacgatggc gacctcgatg acctgttagc tggtctataa taaatcggga 125880
gacttcggtc tccctttttga gtatctgtaa attgccaaaa agttgtttac ttcttcccta 125940
gatgtgatat tatagttcta tcaccaacat gaggaaatca aaatggaaat cggaaaatct 126000
tatatcatta accctttatt taaagacgac tttgttcaag aagcaccaca taataacgct 126060
aagatgttaa aattgattga actccatggg cctagttttg ttgtaaacgg aatggaacct 126120
gattatgata gcgatacgtc aaacgtagta agtgtaacta tggaagatgg tactgtatgt 126180
tctgccggcg gtgaaattga aacttatttt gagatttatc ctgacgagtt caaatacttt 126240
actgaggtag atttagtaaa gcctcaacct actaacaaag gtatagcttt aggtgtaaca 126300
aaaatacatt gtatcgtaga tgaaactaac gtcgatgaaa tcatcgaact tttgcaaaaa 126360
acttttaaaa agtagtttat aacaagatag ggctatgtta tagtagccct atcaaataaa 126420
agtgaaggag aataaaatga gattgcaacg ccagagcatc aaagattcag aagttagagg 126480
taaatggtac ttcaacatcg ttggtaaaga cgctgaactc cttgaacaag ccgaagaagc 126540

```
tttacgtgaa atgggttgga acgaagaatg tgatgggtgt ccactctacg aagatggtga 126600
aagtgcagga ttctggattc accactctga tgttgaatcg tttaaagctg attggaaagt 126660
tgttaagaaa aaactgagga aataaaaatg cttaaattag tattcgcatg cgcaccgtct 126720
aaaacggttg atgataaact ggaatatgct tttggattag gtgatggact tccatggaag 126780
catatcaaac aagatatgag taactttgtt gctcgcacta aaaacactgt aatgattatg 126840
ggtgctaaga catttgcatc attacctcgt ctactcccgg atcgtactca tgtggttgtc 126900
actgatatgg ccagaaaact gcctaggact aaaaccaacg aacttgcaca tttctatatc 126960
acccaagcag aatttattac cttggtaatg ggtagtgaaa ttaatctgtt cagccctgcg 127020
tccgacgtac cgtttaaact ttctactgaa catgttgatg tctcggttat tggcggtcct 127080
gccttattaa aacaagcact gccttatgcc gatgaaatcg tgatgactaa aatcattaag 127140
aaatgtcgtg ttaattctga tgttcaactt gatacagatt ttgtccaaga tattatgctt 127200
caacgttcta tggtagaatc tcattactac agaatcgatg aactcaccga aattactgag 127260
agcgtttata aatgaaacaa taccaatacc tgattaaaga tatcttagaa aatggctacg 127320
aaacagacga ccgtacaggt accggcacta ttgccctgtt cggaactaaa ttacgttggg 127380
atctgactaa aggattccct gcggtaacaa ctaagaaatt agcatggaaa gcttgtattg 127440
ccgaactact gtggttcatg tccggttcta ctaatgttaa cgaattacgt cttcgtaccc 127500
atggtagtct aattgaaggt aaaactattt gggacgataa ttacgaaaat caggcaaaag 127560
accttgggta ccatagcggt gaacttggtc ctatatatgg taaacaatgg cgtgatttcg 127620
gtggtgtaga ccaattagtt gaaacaatcg accgtattaa aaaattacca actgatcgtc 127680
gtcaaattgt ttctgcctgg aatccagctg aaataaatca aatggctctt cctccttgcc 127740
atatgttcta tcagttcaat gtgcgtaatg gtcatcttga tttacaatgg tatcaacgca 127800
gtgtagatgt tttcttgggt ctgccgttca acattgcctc gtacgccgcc ttgacgcata 127860
ttgtggctaa gatgtgtaat cttatcccag gcgatctagt attctcaggc ggcaatacgc 127920
atatctacag caaccacgta gagcaatgca aagaagtttt acgacgtgag cctaaagaac 127980
tgtgtgaatt agttattaac ggattaccat acaaatttag acatctatca accgaagaac 128040
aaatcgaata tgtattaaaa cttcgtccta aagactttat tcttaaaaat tacgaatcac 128100
atccagctat caaagctaaa atggcggtat aaaatgattt tacgttttat taattcgtac 128160
ggcaccacaa tttttgaaat gaaaaatcct accgaactgg atatcccttc accgaatagt 128220
gaaatcacag ttaaaggtga acgattcatt tgctattcac atgaacgaat ttatgaatat 128280
cgtgaatttt gtggtggtta cggcatggaa aaagaaccat tggtttattt cgatatcacg 128340
gtcttgacac ctaaagaata cgaagaaatt attgctgagg ataattaacg cttcagttta 128400
aaagtgtata ataaattaac gggataaata ctatcccgtt tggagtaatg tctatcaacc 128460
tatactgagg actatatgca agtaactaag agcagtggtg tatcccaaaa ttttgatgca 128520
cagaaaatta ttcaagtctt aacttggcaa tgtgaaggaa cacaaattga cccatatgaa 128580
ttgtacgaag aaattaagac ccatcttgtt gacgggatga gcaccaaaga tatccagaag 128640
atttgtatta aagttgcagc taactcgatt tctgtcgaag aacctgatta tcagtatgtc 128700
gccgccaaag ggctaatgtt tgcacttcgt aaagatgtgt acgggcagtt tgaacctcct 128760
gcttttatcg accatatttc ttactgtgtt aatgaaggca aatacgaccc tgagctgttg 128820
tctcaatatt cagcagaaga aatcatttat ctcgattcac agattaaaca tgagcgagat 128880
```

```
tttgacctga cttatgctgg tgctatgcag cttaaagaaa aatatctagt taaagataaa 128940
acaactggga agatttatga aactccccag tttgctatca tggctattgg catggcctta 129000
catcaagacg aaactcatga ccgtttgaaa catattattc gtttttatga tgccgtttct 129060
actcatcaag tttcattgcc taccccaatt atggcaggtg ctcgtactcc gactcgccag 129120
ttctctagtt gtgtagttat tgaagcaggt gattcgttaa aatctattaa caaaacttca 129180
gcatcaatta ttgaatatat ttctaaacga gctggtatcg gtatcaacgt tggtatgctt 129240
cgtgcagaag gttctaagat cggtatgggt gaagttcgac atacaggtgt tattccattc 129300
tggaaacatt tccaaactgc agtaaaatct tgttctcaag gtggtattcg tggtggtgct 129360
gctacagcgt attatccgat gtggcactta gaagtagaga acctattagt tctgaaaaat 129420
aacaaaggcg tggatgaaaa ccgtattcga catatggact acggaattca gattaacgac 129480
cttatgatgg aacgccttgg taaaaatgat tatattactt tatttagccc tcacgaaatg 129540
tcaggcgaac tatactactc gttctttgaa gatcaagata aattccgtga gctttatgag 129600
aaagctgaaa aagacccaac aatcagaaag aaaagaatca aagcactaga actctttgaa 129660
ttgttcatga ctgaacgttc tggcactgct cgaatttatc cacagtttgt tgataacact 129720
aataactaca ctccatttat tcgtgaaaaa gctccaattc gtcagagtaa cttatgttgt 129780
gaaatcgcta ttccaactaa tgatgtgaat ggtcctgatg ctgaaattgg tttatgcaca 129840
ttatctgctt ttgtattaga taaatttgat tggcaagacc aagataaaat taatgaactt 129900
gccgaagtac aagtacgtgc acttgataac ctgttagact atcaagatta tccggttcca 129960
gaagctttaa aagctaaaaa gcgtcgaaac ctcggtgttg gtgtgacgaa ctatgctgca 130020
tggttagctt ctaactttgc ttcatatgaa gacgctaacg atttgactca tgaattgttt 130080
gagagattgc aatatggcct tatcaaagct tcaatcaaac tcgccaaaga aaaaggatgt 130140
tgcgagtatt attcagacac taaatggtct agaggcgaat tacctatcga ctggtacaat 130200
aaaaagattg accaaatcgc agccccgaac tacgtctgtg actgggaaga acttcgagct 130260
gaactcaaag aacatggaat tcgtaactca acgttgtctg cactcatgcc ttgtgagtca 130320
agcagtcaag tatcaaactc tacaaacggg atcgagccgc cgcgtggtcc agtaagtatt 130380
aaagaatcta aagaaggcaa cttccgtcag gttgttccta atatagaaca taacatgggt 130440
ctttacgact acgcgtggaa acttgctaag aaaggtaata aaccttattt gacacaagtt 130500
gctatcatgt tgaaatgggt gtgccaatct gcttctgcta atacttacta tgaccctgcg 130560
gtatttgaga aaggtaaagt accaatgtca gtaatgcttg acgatctact ttacttctgg 130620
tactttggcg gaaaaaacct ctactatcat aacactcgtg atgggtcagg tacagatgac 130680
tatgaattag aaacacctaa agctgaagat tgttctgctt gtaagcttta agacttttta 130740
ttataattta ctcatggatg agttaaacta agtgagaaaa tataatgagt acagttttta 130800
acacacaaca agtcgatgtt ttgaatgaac cgatgttctt tggttctggt cttggtattg 130860
cgcgttatga tattcaacgc cataaagttt ttgaagattt gaccgaaaag caattatcat 130920
ttttttggcg cccagaagag gtaaacttga tgttggactc tgcgcagttc aataagcttc 130980
ctcagttcca acaggacatc tttacaaaca atcttaagta tcaatcatta ttagattcta 131040
tccaaggcag ggccccgtct gcggtactta tggcactgat ttctgaccct tcattagata 131100
catgggttgc aacatggaca ttcagtgaaa ctattcactc tcgttcgtat actcatatta 131160
tgcgaaatct ttatactgat ccatccaaag tatttgatga gattgtatta gacgaagcaa 131220
tcatgaaacg agctgaatca ataggtaaat attacgatga tgttctggtt aaaactcgtt 131280
```

attgggaaaa cgctaaagct gatatcgaat accaaaaaga aattaatgca gacgaagacg 131340
ttattgaaga tgctattgag catgagacat attggaagcg tgagctaatg aaatctcttt 131400
atctctgttt gcatgttatc aacgccttag aagctattcg tttttatgta tcatttgcat 131460
gtactttcaa cttccataaa aatatggaaa tcatggaagg taatgctaag attatgaagt 131520
tcattgctcg tgacgaacaa ctccacctca agggtactca gtacattatt cgtcaactcc 131580
aacttggtac tgatggtgat gagtgggttc aaattgctaa agaatgtgaa caagaagcag 131640
ttgacatttt tatggaagta aatagacaag agaaggaatg ggctgcacat ctctttaaag 131700
acggtacatg cccaggtatc aatacgcaga gtatgtgtgc ttttgttgat tacttgactg 131760
tgtctcgtat gaaacagtgt ggtttgccat gtccaattac tgatgctcct accaagcatc 131820
cgtatccttg gattcgtgaa tatctgaact ctgatttagt tcaagcagct cctcaggaag 131880
ttgaaatcag ttcttatctt gtcgcacaaa ttgataatga tgtagaccaa aatgtaatca 131940
attcatacaa aaaatatttc taaggacggg acttcggtcc cactttatta tgaaagatat 132000
tgccgccgaa tattccttta ttaaatatac agaattggag ctattagaag atgcaacaat 132060
taaaacagtt gatgtcccta ataagaaaaa tgtcatatac gctattgcta tagatgacga 132120
acttgtgtat attggtaaaa ccaagaattt aaagaaacgc attaactatt atcgaacagc 132180
cataaatcga aaagaccaga cttcagattc aagaaaatct cttatgattt tggatgcctt 132240
aatgcaaggc aaaaaggttg aattctgggc ccgccaatgt tttgaccttt cagtcaccaa 132300
cgaacttggt tcaatgacca tcgcaacaat ggaccttgaa gaaccgcttt ttatcaaaaa 132360
gttcaacccg ccttggaata tccaacataa gaaaaagtag tttacacgcc acaaggattg 132420
tggtacaatt taaaaaacta actgaggata caaaatggaa aagctttatt ataatctgtt 132480
atctctgtgt aaatcgtcat ctgatcgtaa atttttctac tcggatgatg taagtccaat 132540
cggtaaaaag tatcgaattt tctcatataa ctttgcttca tattcagatt ggttattgcc 132600
tgacgcgtta gagtgccgtg gtattatgtt cgaaatggac ggtgaaactc ctgtacgtat 132660
tgcttctcgt ccaatggaaa aattctttaa tctaaatgag aacccgttta cattgtcaat 132720
taaccttgat gatgtaaaat atctgatgac taaagaagac ggttcgttag tctcgacata 132780
tcttgatggt gggactgttc gtttcaaatc taaagggtca atcaaatccg accaggctgt 132840
atcggctacg agtattttgt tagacattga ccataaaaac ttggctgatc gtttattaga 132900
actttgtaat gatgggttca ctgctaactt cgaatacgtt gctccaacaa ataaaattgt 132960
tttaacatac cctgaaaaac gattgattct tttgaatatt cgtgataaca acacaggtga 133020
atacatcgag tatgatgaca tttatctaga ccctgttttt cgtaaatatc ttgtagatcg 133080
atttgaagta ccagaaggcg actgggcctc agatgtcaag tcttctacaa atattgaagg 133140
gtatgtagcc gtaatgaaag acgggtctca tttcaaattg aagactgatt ggtatgttgc 133200
tcttcatacg actcgagact caatctctag cccagaaaag ttgtttcttg ctatagtgaa 133260
cggtgcttca gatgacctta aagcgatgta cgcagatgac gagttttcat ttaaaaaggt 133320
cgagctcttc gaaaaagcat atcttgattt cttagaccgc tcattttata tctgtttaga 133380
tacatatgac aagcacaaag gaaaagatcg taaaacgtac gctatagaag ctcaggccgt 133440
ttgtaagggt gcacagacac cttggttatt tggcatcatt atgaatcttt accaaggtgg 133500
ttcaaaagag caaatgatga ctgctctaga atcagtcttt attaaaaatc ataaaaattt 133560
catccctgaa ggatattaat ggtttacaaa caccaaggat ggtgttacta tggcttttat 133620
caacaacacg aggagaaaat tatgaatatg caattgatta ctaacgatat ggttgtggca 133680
gcatttggtg attctacaga tggaatccgg gtctttaaga aaggccgtgc agttggttat 133740
cttacggacc ttcgtactac tctagcgaaa aatgctaaaa agaagttaaa gcaaaaggaa 133800
tattcaacac gttacgccga agagaaacgt gaagcgatgc cggaagcagt taatgccatg 133860
gtagaatttc ttcaaaacaa tttgactaaa tatgacgcta atgtgttcat taatattagt 133920
caaccaaacg tacatatcgc aggtataaaa ttctacatta tttgcgaccc tcttaccgac 133980
aaattcaacc gtctcggaat ttcaagtccg tatcatacag cagaagagtt gtgtgtattg 134040
tttgaatcgt acaaaattca gtgtgatggt ccgaaaaccg ttcttatcaa tggattatcc 134100
cgagatgaaa tcattgagat tattaaaaca tgcttaaagt aaatccgatt tatgctatag 134160
tagcagcttt tgctctagtt tctacggtaa caatagttgt cttaaacaac aaagttgatt 134220
cgttgaatac tgaattagct tctgtcaaag agaccgctaa aaacaatgct aaagtattag 134280
acgacttcaa ggttcagtat cagtcaatcg aagaaatgac ttataagaac cgtgttttag 134340
ttgaccaact taaggccgaa aatgaaaagc tccgtaagga ttcgaagaag aagaacgtgg 134400
tggcgagtaa gccaggattg gtcgaaaaac aaatcaacaa gtccttcgat tcctttgcag 134460
aagacctcag gaagctctca gaatgattaa attaaccgca gttgtattat ctattggcat 134520
tttggctgga tgtgcccagg atgtgccctt aagccctaaa gaaactttac atccgccatg 134580
gccagaatct attgttgaat ataaccagaa atggcaagta aaggttattg atggtaatcc 134640
atgggttgga atgccgtttg aagactctca agaatttcgt atctggttaa acgacgtaaa 134700
aagatatgta catgaccaga agactatgat atgttattat cgtagtggtt taaaagagga 134760
aaaatgccaa tgactaaaga acagcatgaa tacattaaag ggcttatcta tgaatctgaa 134820
atggcggcca tgatttacgg gcgacagatt caacgattag aatctttgcc tccgactaat 134880
gaccgcttgt tagttcagtc tcgtgctaat ctgaaaaatg aatatcagaa taagtgggca 134940
gtagcgacta aagctcttca cgagtatatt gaatctttag taaaatagtt tacaaactct 135000
caggagcaga gtataatgct cctatggata attgaggaaa tctaaatgaa aacattacta 135060
gagaattaca tcaaacggtc tgatgagtat attgatatct gtcgtggaat gtcacttggc 135120
aattatgaca aagatgcagc aaaggcacta gatgaagcag gtaaagctct tcgtaaagct 135180
gctaaagaaa aagggttgga tttgcaacaa ctcaaaagtc atatgattaa atttatttct 135240
tcaaacgtta gaagtacgtc aattaataaa aacgttgctg aaattaataa agaccggcgc 135300
gagcataaca ttcgtattct tgaaattttc ttaggaataa aataatggac caagccaaaa 135360
tcgataagtt aatccatacg cttgtagcag atatcaatac acgggctctt cgtaaatcac 135420
agaatggcga ttcctggact atgcaagatt gcaagaaagg tgctgaacta ggacgtgaaa 135480
ttgctaaaat tcttggtgga caatttgaat ttgctgaaga ggtagtaaaa ctgtgaaaaa 135540
gattattttg actgtaggtt gtcctgggtc tggtaaaagc acttgggctc gtgaatttat 135600
ttctaagaat cctgggttct ttaatatcaa ccgcgacgat tatcgtcaat ccatcatggg 135660
ccacgaagaa cgcgacgagt acaaatacac aaagaagaaa gaaagtatcg taacttatat 135720
gcaacacgac gcggcacata tgattctctg tcaagacgga actaagggtg ttattatttc 135780
cgacaccaac ttaaatcctg aacgtcgtct tgtctgggaa gaatacgcta aggagtgggg 135840
ccatgaagtt gtatatcaag tgttcgatgt tccatggacc gaattggtta aacgtaatgc 135900
taagcgtggc acaaaggccg ttcctattga tgttctacgt tcgatgtatt ctcgtatgcg 135960
tgaatacaaa ggacttccgg tttataaagg aactccgggt aaacctaaag cggctatctt 136020

```
cgaccttgac gggactttag ctctacatgt tgctcgtggg ccatatgagt tggataaact 136080
gtccacagat gagccgaacc ctatggttgt cgaatatgtt aagatgcttc atcaggcagg 136140
gtatacaatt atcactgtaa gcggtcgtga atctggaact aaagaagatt caatgtgtta 136200
ttacgaagca actaaaaaat ggatggacac gttttctatt ccatgggaaa tgcatattca 136260
acgtaatcaa ggtgacactc gtaaggacga tgttgttaag gaagaactct tttggaactg 136320
tattgctcct tattatgatg tgaaattggc tgttgatgac cgtaaccaag tcgttgagat 136380
gtggcgtcgt attggtgttg aatgctggca ggtcgccgcg ggcgattttt agttagaaat 136440
ctccatagat aagtataaat atctatggag gtgattctaa tggaaaaata tactgtatat 136500
aaaactacat gtttggttaa taataaaatt tatatagggg ttcataagac cttggaagaa 136560
aacgattctt atttaggttc cggtacagct tttaaaaatg ctgtatcaaa atatggtaaa 136620
gattctttta ttaaagaaat cataaaaata tttgaaacta aacaagaagc atacgcactg 136680
gaagccaaat tggtaaccag cgaatttata aaatcgaata ctaattataa tttgaagccc 136740
ggtggagaag gaggttggga gtacattaat gaaaatcgta ttaatgttaa ctcgagtccc 136800
gaaacttcgt taaaaatttc agaatcacaa aagcaaagat acaaaaacgg tgctatacca 136860
tggaataaag gcaagaaatt gcctggtagt gggcttaaat ccaaagaaag ccgtcttaaa 136920
aatggtaatt catttaaagg cgaaaataat ccaatgtacg gtaaaaatgt aaaagatttt 136980
atgagtgaag aagctattat agaatggggt aataaaatat ctaaagccaa taaaggtaag 137040
attcgttcag atgaggcaaa agaaaactat tctaaagcgg ctaaatccag aaaatggctt 137100
atccatattt caggtaagaa atcttctaca acagatgaaa acgaccctag attgagccat 137160
cctgattggc aactaggccg caaatggaaa acctatgaat aatatcgaaa agatttttcg 137220
tacaatcgaa gaaattgaaa aacgtaaatg ctttttcttc ggcatatggc ctttagtaaa 137280
tggacggttc ggtattgatg tgctggacta tgaacatgaa gaatggttgg acggcggtat 137340
atttgataac gtcgaccagg caattgaatg gttaaatgaa aactatgtac gataaacatc 137400
atgaaatcga agatgaagca tacaaaatgc ttcgtaaact agtgggactt aatatgagtc 137460
ctacattaat caacaaactc gcaggaattc gtaatgatct gaatactcgt tacaaaggtg 137520
aatatcatgt agagtttgtt cctgtgggtg aaccaaccga gcgatttgtt gttcgagtta 137580
aagtaaatac tgtacactga ggtaattatg ttcccaactt attctgaaat tgtaaaggta 137640
gtcttcagtc agattattgc taataaatatg tttgaagtgc ttgataatgc agccgaactc 137700
agagttcatg ctcaactaac tcatgtactc aatgctttgc tcccagacca agtagattct 137760
attgctatta ctcttctccc tgggtctgca cacgtcatag tggtatttga tcttgacggt 137820
gatttagtta tccaatgtga tatcaatttc ggtacacaaa aaattgaatg caaagcaatt 137880
taatggttta caacatggtg gagttgtgat actataactc taccaacaaa tgaggaaata 137940
gaaatgctaa gtgaaaaccc aattacagta cacgaatttc agattaaagt aaaagaattt 138000
gctcaagcac tcatcaataa agtgtctgaa cgtttccaag atgcaacatt acgagttatt 138060
caagaatctc cacgttcttt tctcataatc gttaatccta aagatggtga ccaaattact 138120
aatcttaaat taggcagtga tggtcttgtt gaagcatctc gagtatatgg aacactataa 138180
tgagagctat ctcattacta tcgagaatgg tcataaatct gagcactacc aacttagcct 138240
gtctaatccg gttaaaggta ttgttgaatc agaatctgtt tatatctcct aaggattgtt 138300
atgttacctg tcgtcagaaa acttatttct ccaaaagaac tggctgagat tattcctttg 138360
```

-continued

```
tcggaagctt acgcatcaca agtggcttct catcgcgaac aagttaattc gattatgaac 138420
ggtgaagacc cacgcaaact tattgttgta ggtccttgtt caattcatga ccctattgct 138480
gctgttgaat acggcaaacg tctggctgaa cttcaaactc gtcttcctaa tgttctgtta 138540
gtgatgcgcg tttattttga aaagcctcga actaccgtag gttggaaagg tcttgtaaat 138600
gatccatatc ttgacggaag ttttgatatg aaccacggtc ttatagttgc acgaacattg 138660
tgtcgtaaac ttctacgtat gggacttcca ttagcaactg aagtattaga cccattcacg 138720
attaagtatc tttctggtat tttctcatgg gttgctattg gcgcccgtac gactgaaagt 138780
cagacacatc gtgaaattgc ttcaggtcta ccgatgtgcg taggcttcaa gaacgcaacc 138840
aatggttcta ttaaagtagc tacagacgcg atgtatagtg ccgcctggcc tcatcggtat 138900
atgggtatgg acgtcgatgg tactgtaggc attgttgaag ctgaaggtaa tcagaatacg 138960
catatcgtat tgcgtggcgg gactaacggc ccgaactatc attcttctga tattcaagaa 139020
gcttctaaca aagcaagtgc attaggtctg aatcattatg taatggttga ctgtagtcat 139080
gcaaacgctg atgggtatta tagcaatcaa attggtattg gtaaaaattt agcagctaat 139140
gatttggtca aaggaattat gatagaatca ttcctacatg aaggaaatca aaaaatttct 139200
gataatatgt cctatggcgt ttccgttacc gatgcgtgca tcagttggga acaaactaaa 139260
gagctgttaa cttatattaa taaggttcaa taatgaaagc tagcacatat cttcaaattg 139320
cttatttgat ttctcaagaa tcaaaatgtt gttcatggaa agttggtgcc gtcattgaaa 139380
aagatggacg cattatctct actggatata atggctctcc ttcaggtggt acaaactgtt 139440
gtgaacatgc atccgaaaat ggttggttga agaataaacc aagcccggtc atcgttgctg 139500
gacataaaga aggcactaca gcatttggac gggcagataa ttttgttttg gctaaagaac 139560
atcgggccgc tcatagtgca tggtctgcta ataatgaaat ccatgcagaa ttgaatgcaa 139620
ttttgtttgc agctcgtaaa ggtaattcta ttgaaggtgc tacgttatat actacgcttt 139680
ctccatgtcc tgattgcact aaagctatta cgcagtcagg tattaaaaag gttgtatacg 139740
cagaattata cgatcgatct cctgaaaatt gggcagacat tctaaaacaa gccggtattg 139800
aagtaattca gtactctcgt aataatcttc gttctctgaa ttgggaacaa atccgaaact 139860
tttgtggtga ataatatgat tttaactgaa caagaaacta tggttcttcg tgaacgtatt 139920
aaaactattc tgtctgtagg cgttcattgt gttgtatttg aaaaggctaa cggcgaggta 139980
cgcactatgt ttgcttcgcg cgatgaactt gaagtcaaat atgaaaataa caatccagca 140040
acagaagttc gttatgaacc tcgtgaatca gttcgagcat tcgataccaa gttaggccag 140100
tggcgttctt tccgccttga taaagtaatt tcggttgatg gtactccggc ggaacgtttg 140160
cttcttatgt aatatgcttt acgaatagta tggtattatt aatctatcgt caaacaacaa 140220
ggaaataaga tgtctgaagt acaactccca attcgtgctg ttggtgaata tgtcattatg 140280
gtttctgaac ctgcccaagc aggtgatgaa gaagttactg aatcaggact tgtgattggt 140340
aaacgtgttc aaggtgaagt tcctgaacta tgtgtagttc attctgtagg tcctgatgtt 140400
cctgaaggtt ttgttgaagt cggtgatttg actccactac cagttggaca aattcgaaat 140460
gttccacatc catttgtggc tttgggactt aaacaaccta aagaaattaa acagaaattc 140520
gtaacatgcc actataaagc tattccgtgt ctttataagt gatataaata actatatgaa 140580
gagaacactc ttctaagcgg tagcctacaa ctgagagacc tgtcgaaaga aggtgaaatt 140640
cagacgaacg tggctactaa atattgtctc gaattgagaa tttaaaatga ttaaacaatt 140700
acaacacgct cttgaactgc aacgccatgc atggaataat ggccacgaaa attacggtgc 140760
```

```
atctattgat gtcgaagccg aagccctcga aatcttacag tatttcaaac atctgaatcc 140820
agcacaagcc gatcttcgcg atatcctggt tcagaaagat gaattgaaat atgctaagcc 140880
tctggcttct gcagcacgta aagcagtacg tcattttatt attaccctga agtaagctaa 140940
atcgaggagc cgtcgaattg tctgattatc gatttgcgaa tcggtatgtt ttagaagtac 141000
caccacgaca attttacggt gtacctcttg aatgtatttt gtactatcac gcgtcagaaa 141060
agggttatct gtttaagtcg tggttggtat gatgacgagg tttatggtta tcctgtcgtt 141120
aaatatctaa aacctatgtt cccettgagg gcttgcgcag gcaatgtcaa taagtcctgc 141180
attttcattt aaagagaatt tataatggca aaacaagcta aagcaaagaa agcagttgaa 141240
aagaaagttg atggtacctc taaacgcgct ggatacaagc gtgggtcgaa ctctcgtatt 141300
aatcaaacag ttgagaagat catgcgcaga gcacgtgcag ttcttcgaga tgatgcttct 141360
cgttttggaa aggttgttgc ataattttag ggagacttcg gtctcccttt tgtgcgttta 141420
gggcagaaaa agtttaaaaa gatgtttact ctcctgtagg atgtgttact atagacttgt 141480
accacctaat caataaaaca aaccggagaa caaaatgaaa atcaatctga actcatacat 141540
caaatgtaaa gaccacgacg gttataaagc tatcgaaatt aaagaattcc aatggatgtt 141600
atacaaagag caatttgagt tcgtaggttg tatgacccct gaaggtcctt ctgatgattt 141660
ctcttggaaa attgtgttag caaacttttt cacgggtgac acatacgaat taaaaactat 141720
tattactggt aaaattcgct cagaaacata tgttgacgaa gaaactggtt actctgaaga 141780
tgtcacatgg tatcaaaatg gacgcattac agcagataac ctgatcgaaa aaatgaaagc 141840
caaaggtgtt ttaaatttag acaattggat taaagttgca taaaacagtt tactttggta 141900
caggttatgt tattatagac ctgtaccaac aaacaactta aacatccgga gaataaaatg 141960
aactacacca acttcgaacg taaatatgtt tctaacggta ttgctggttc ttctgaagtt 142020
atttgcttat ggaaacacga aaacggtaca gtttgtgaaa tcgaacagtg catgactcct 142080
aattacgttt atatgcgatt tgaaaatggt atcacggttt caatcacgat ggaaggttca 142140
aattttaaaa ttgcattaga tgatgatttc cgtcagcgtg atttaggtac tcatccttgc 142200
tggaatggtg ttaatcgtaa acttctggtt aaaacttgga ttcgtcatat cctgagtaac 142260
cgagctaaac ctgaacatct cgaagcaatc tttgatgtag ttcttaacga atttgatatc 142320
taaattaatt gggagcttcg gctcccactg aggaaattat gtttaaagtt aatacttttt 142380
ataaaatgaa ttttaaaaat ggggatatta ctccacgcct taaaaacatg ttctcatatg 142440
accttattga gccttttgaa gttttagaag ttactgatgc cggctcggtt tgtgaaatta 142500
gaacttctga aggtaaaatt tatcaggcgg gtgttggtaa attcagtaat tgttttactt 142560
taatattctc gaccgattta gatgagcatt ttattgaatg tcctaaccct aaggtctatg 142620
aagttccaca tcaagaaact aagaaaaatg gcccgcacga atatacgaag gttgaaactc 142680
ctcacggcgt gatgtggcga cataactctc cttttggaag taaaggaaca tttgctcaac 142740
tggctaagcc ctacgacgat gaaaaatatg tagtagtcct tttatctgaa cagggtactc 142800
aagaccgtgg atgccaacgt tccggtttat tgagtgaact cgaagctcat aaccgagcac 142860
gtgaattcgt tgagaaaaat cctggttctg aagctctagt catgaaagca attactcaat 142920
atatcactgc tcaacctgtt gttcatccgg tagaaattaa tttcattaag tagtgtacat 142980
ccaaggacgg attagagtat aatgatttct ttagtaagtg gaaaaaaata tgaaattttt 143040
aatagcacaa acagtccaat taaaaggtgt tggaatccct ggggtgattt ttaaagttct 143100
```

-continued

```
ccctgaattt aaaaccggcg ctggaattat caatgaagcg tatgctgttc aatgggttga 143160
ttggacttct gacatacgta tgggtaaaga gttatctcct attaaagggt tgaaacatgt 143220
tgaataaatt aatccagaaa ttgtttggta cggaaatgat tgaagttact tatcgtgtaa 143280
ccgacgtttt tccatattac gcggaaaacc gtttagaacc atacgttacg tcaattaaaa 143340
tgcctaaaac tgatggaaat ttatctatca aagaccgtct accggcttat ggtcattggg 143400
ctgatgttga aattataagt gttaaagatg tctgagttag agattagaag caattttaga 143460
tggccgtcat gtgcattaag taattttgcc cagtggcctt tcgttatgga tggtattcaa 143520
ttcggaggtc ttgaaggatt tctccaagga tgtaaggtga aaaatgttga acaacaaaga 143580
cgtatatttg ggctgtcagg actggccgca cagcaagctg gaaggtctta tgcaagagct 143640
caggaccatg ggactctctt ctggttagga gttccatttt caagatactc tgaagcatgg 143700
aaagaattat atacaaatgc atattttgaa gcagcgatcc aaaacaaggg gtttcgtgat 143760
gccttacaag cctctaaagg aaaaattttg aagcacagca tggccagcca cctaacaaaa 143820
gatgatacaa tactaactga agatgaattt attgatgtgt taaacctatt aagagactct 143880
ttatgaagcc tactattttg actgatattg atggtgtatg tttaagctgg caatctggac 143940
ttccttattt tgcccaaaaa tataatcttc cattagaaca tattttaaaa atgattcagg 144000
acgaaaaatt tatttctcct ggtaaactgt tcaataccga cgataacctt ggtaaacaat 144060
taatagaaaa atataatagc tctgatttta ttcgttactt agcgccttat tcggatgctc 144120
ttcgagttat caataaacta aaagaagact ataattttgt agccgtgacg gcactaggtg 144180
attcaattga tgctcgattg aatagacaat ttaatttgaa tgctttgttc ccaggcgctt 144240
tctctgaagt aatgatgtgt ggtcatgatt cttcaaagga acaattattc gaactagcta 144300
aaacaaaata taacgtgatt tgttacgttg acgatttagc tcatcactgt gaccatgcag 144360
cagaaattct taatgtaccg atttattggt tggctcgtgg tgaacgtgat gccattcctc 144420
gtactgcaca acgtgtacac acgtgggatg atattgaatc tcgtttggtt ccacccaagc 144480
ataattcaga ttcagatcat gaagaccttt taaaacgatt ggcagatttg cttaaagaat 144540
ctggtgcaac aagtccaggc gcatggccta atcaaattgg cgctccgtcg aatccgtata 144600
cctggcgaac cccaggacca accaatatgc agccacggtg gacgattcaa aactttcctt 144660
tagattcgtc caaatggact tggtctataa attgttaagg gttaattatg tttgtagttc 144720
atgatattac agatggcaaa aacacaactc gtgactacgg tcacgttaac atgttctttc 144780
gagattggcc agtgtttcgt tcagtaaaag acgcagaaat atttaaagag tgtgttgaac 144840
aagggttcat ctacatttca gaatattatg ttgaaggtct cggtaaatgg attaccactt 144900
atcagaaaac gctgaaatcg cttctagatg aagtggctta taatagaacc gtaaccaaaa 144960
tcgaggacat caaatgattt tagatatttt aaaccaaata gctgcgatcg gttctactaa 145020
aacaaaacaa gaaatcctta agaaaaataa ggacaacaaa ttacttgaac gtgtgtatcg 145080
tttaacatat gcacgtggta tccagtatta tattaagaaa tggcctgggc cgggtgaaag 145140
gtctcaagcg tatggacttc ttgaattaga tgacatgttg gattttattg agttcacatt 145200
agctactcgt aaactcactg gtaatgctgc aattaaagag ctcatgggtt atatcgctga 145260
tggtaaaccc gatgatgtag aagtccttcg tcgtgtaatg atgcgcgacc ttgaagtagg 145320
tgcttcagtg tctatcgcga ataaggtgtg gcctggactt attcaattgc aaccacagat 145380
gttagcatct gcatatgatg agaaattgat tactaaaaat attaaatggc ctgcatttgc 145440
ccaattaaaa gcagatggtg ctcgttgttt cgctgaagtt cgcgatgatg gtgttcaatt 145500
```

```
cttttctcgt gctggtaacg aataccatgg tcttactcta ttagcggatg aactaatgga 145560
aatgactaaa gaagctcgtg aaagacaccc taatggggtt ttaatcgacg gtgaattagt 145620
ttatcattca tttgatatta aaaaggctgt gagctcagga aatgacctgt cgttcttatt 145680
tggtgataat gaagaatccg aagaagtaca agttgcggac cgtagcactt caaacggttt 145740
agcaaataaa tctcttcaag ggactatttc tcctaaagaa gcggaaggta tggttcttca 145800
agcctgggac tatgttcctt tagatgaagt ctattctgac ggcaaaatta aaggtcagaa 145860
atacgatgtt cgttttgctg ctcttgaaaa tatggctgaa ggctttaaac gaattgaacc 145920
tatcgaaaac cagttagttc gtaatcttga tgaagctaaa gtggtttata aaaaatatgt 145980
tgaccaaggt cttgaaggta ttatccttaa aaaccgtgat tcatattggg aaaacaaacg 146040
ctctaagaac ctaattaaat ttaaagaagt tattgatatc gctttagaag ttgtaggata 146100
ctatgagcac tctaaagacc ctaacaaatt aggtggtgtc gaactcgtat cacgttgtcg 146160
tcgtattaca accgattgtg gttcaggttt taaagataca actcataaaa cagttgatgg 146220
tgtaaaggtt cttattcctt tagatgagcg tcatgatttg gaccgtgaac gattaatgtc 146280
tgaagctcgt gaaggtaaat tgattggacg tattgctgat tgtgaatgca atggttgggt 146340
tcattctaaa ggacgtgaag gcactgtagg tattttcctt ccaattatta aagggttccg 146400
ttttgataaa acagaagcgg attcatttga agacgtattt ggaccgtggt cccagacagg 146460
tttataatga aagcttattt agaaacagtt attgtagcta agaaggatgg tggagatgtt 146520
tccacctctt gctctcagat tatattagat tttcctaata acgattccta tcatattttt 146580
atggacaatt ttgataagta cgaaaaaggc cctaattttg aagtttatcg tactttgcta 146640
ccgattgtgg attaagagcc ttcgggctct ttttggcata aatataaatt attactaaaa 146700
ggaaaacact atgtctgaac aattaaatga agtgtttgaa tctgaaggca gtcttcctgt 146760
cgtcaatttg aaccctaaag ctaaagttcc gcaagtctgg aaaattggtg atgttgatac 146820
aaacatcgta gttcgcttat tctcttacct ttctgaaggc gatgctgtaa aacaagttaa 146880
acttggcgac aaatacgctc atgttgttat tatgagtctg tctgaaaagg gtaatctcgc 146940
tgaattgaaa aatggccttg gtcctgctcc tattgatgca atcaacacca ttttcaatac 147000
agtatatgaa caggttaaag ctcttcgtat ggatgcagtt ctgttccgat tccctaccaa 147060
gaaattgaaa ggacgtggac aacaacttca aactcttctt gctcgtttag tttctactaa 147120
aaccggtggt cgttttaaag tattgtcggc aatgtatcaa ttcacaggta aacacaccta 147180
tgtgatgatg gttcgtaaaa atgccaacat tgaagatatt aaaggcatcc ctaacattaa 147240
cacagagttg tacacgaaag tagattctga tgttggtgaa gtttatgtga gtaaaaagac 147300
tggcgaaaaa gtcaccaaag aaatggctat cgctggttct attgctgctg tagaagaaaa 147360
acgtaaagat aagcctgtta ttgctcgtac taaaatttct cgtcgcgcta ttgcagcaag 147420
tcaatcttta gaagctgacc gccaagaagg tgagctattc cagaaatacg aaaattctgc 147480
taaagaagtt agtggcccag ctacagctga attacttcct gaagcatatg aaatcgtact 147540
agcccaagca tcgtccacag caaaaggcac tttagttgct gatatcgaaa ataagattta 147600
taatcgtatt gatgaatcct ttaaatttgc tgatgaagtt tcttatggta gtgttattaa 147660
gccgacttta gaaaagtttg ctaagaaaat taaaactgaa aaaacaacat ctgttaaagc 147720
attagctgct tttgttgaag ctgcaaatga aattgcagac tctattaaag acgaatggtt 147780
tgaagatttt agacgtgata atttccaact ggccgacgac gttttagctg aagtatctga 147840
```

aaaaacttgg aaacaacgta aatcagcgtt cttgtctaat gtgatgtata cttatgcacg 147900
agaatcggct agaggcacct ttaatataac aatgaatcgg gaccccaaac aatactctgt 147960
tgctgaaaaa cgagctattc gtgaatatgc ctcttctgcg tatactgata tcaataatat 148020
gttgttaggt cgttataaac cagattttta cgatgttgcg gatgaagatg aagttaaacg 148080
cgctattgat ggtcttgatt cggcgttttt aaatggagac cgtttacctg aaggactaac 148140
gttatataga gctcagtcta tcagaatgcc tatttacgaa gcaatggtta aaaataaggt 148200
attctacttc agaaactatg tttccacttc actagctcct attattttcg gtgggtttaa 148260
agagaacgtt gcccttggac ttgctcctga agaagttcgc aaagagctta acattgacaa 148320
taatgatgaa ggtgttacta tttctcctag cctggcgcgt accgctatgc atgcgccaga 148380
acaaattcgt gttaatgttg gatgggctat tgatggcgcc cataaagtta acgtgattta 148440
tcctggacag ttgagtaatc accctaatga gcaagaaatt attttgccta gaggcattct 148500
cttgcagata aataaaatta cagatgcgtc atctgacact ggtgcaggtt tagaatctaa 148560
ccttaaattt attcaagctg aagtcatgtc ctcggaccag ttggacgaag ctgtcattta 148620
cgatggtgat gttctcatgg aaacaggcga ggtagttgct atgacgggtg aaattgaatc 148680
agatgagccg gtatcttttg cctcatttgt agaaaaaact agtgcaccta aaggtttgaa 148740
attgttagca tctttaatgg atttagaatc agttccgttt aaatttatcc aaggatagtt 148800
tacaaacaca tggatgtgtg atactatcat cccatcaaca acacgaggaa aacgttatga 148860
aatctatgct tcgctttaat ggtcaagaac tagtagttga agatgttatc ccagcggatg 148920
atgcttttaa cgaagctgtg attgacgaat tgaatcgagt attcccaggt gcattccata 148980
ttgctatgga acctcttaaa aactttcgtg accctgagca cactgatcaa atttttgtcg 149040
gtgtagtgac aggtcattta gaaacagaag taccaatggt cgtattagtt aaatactcta 149100
aagatgatac tccattccga gcaccagcat tcctttcatt ccgtaaataa accccctaaag 149160 ggagacgttg tctccctttt tcttatagtc ctaaaactct tgacgcagaa ttcaccacac 149220
ctgtcaatgt gtttatatta gacacaccac cagcagtccc acctaatcta gaaagtcttg 149280
atactgcact tcctagtcca gaatcattct gattatttcc aaacattcct gaaacactac 149340
taataagtcc tgattccagc cattctaaag cagcctgtct atttacagca cctgattgca 149400
taacgcgata agcaaatgtt acatcaaaaa ctgttatctg attatcacca tcatacgtta 149460
actcaggaga agagacacta acaggaatac atcctgtgaa catgacagcg gtatgtggta 149520
aaccatttcg tgcatgtaaa ttaacctgaa tatctgcttc gacgtcttgt ggtaaagcac 149580
gaagacctgt tacagggtct tggaccgagt ttacccagtc ttgcattgct ctaaagttag 149640
atgcttcgga atccattcta aagcttatta ctaacgggtc catttcacga ccggtaattc 149700
ggatattcgg ggagttatag ttgaaatccg tttcataaga taatcggttc tcaggcattt 149760
ttacagaata aatcattaaa cctgtattat tatatgccat attgaagaag tctatcagat 149820
aagttcctac tgtgaactca cctaacaagc tttgtaccgt acgttgactc attgctccaa 149880
tcagatattt acttatacct gattttcgaa ttaatttctg tgttcctgtt gtaatcaggg 149940
ttgttacgcc ctgattgata tcaccttgag acaatcctag ccaatctgaa tccaacccta 150000
agttattata agcaaaacta ccaattgacg aaattagtga agacgatttg gttgatggtg 150060
tagtagcaaa tacacaacta aacatattgt ttcgttggaa atctgcattt atagcttggt 150120
tattaaattc ttctaaagag tacattagaa agtccccgca taaagtgaag aacggtttaa 150180
tgtaataatt tctcgcattg ttatctctaa cgtaaatgtt gatggtaagt taggagcaac 150240

```
agcaagacca ttaaattgtc catttggagt tttatcaaaa cgtacgcttt gaatttgaca 150300
tgggccaaat acgtcagtta atccatcaaa tttagatgta taaccaaagt ttttaaccat 150360
ccaaattgta gggttgctta caactaatac atttgttaat gacgcagtaa tcttttcaaa 150420
caatgtctta ttttttactg catcatccgg cgtcataggc tcaataaacg ttgaacggta 150480
ccattcgtct aaataacttt taatctcttg ggcgtactgt gatttaccag tctcaccata 150540
tgagaaatag ttaaaatact ggtaaatgtt tataatagcc ataaggtctt cagttgaacg 150600
tggagttaaa tcccatgtaa agactttagt acggttctca gcgccgccat acatactacg 150660
agaagtcgta taaatctgtt cgttattatc agccataagc ccttgagtaa tagaatctaa 150720
tgcaccaaaa actgcagtag aagcaatgtt acttaaaaca ccagtagcag tacctccacc 150780
tttagtaata aggctatcac caatatcatt aaaacgatgt gaagttgtat caacgtcaga 150840
tttggaacgt ggcaaaagta tattagcaac aggagtttta tttatagtgg gtttattagc 150900
tccggcagga agcaacccat tagagaattt agtcactgca tctttcacat tatcagttaa 150960
atctgatatg ataccgttag atgaagtgcc ggcatatgcc ggacgtaaat tcctgaggga 151020
tcctgaatcg cgtgcagaca tattgtacgc ggtaaataat aatccattct tataaagatc 151080
tgttacctgg aagtctcctg tggagtcatt tccggctgct cttcctgtag gaaattgagc 151140
aacataagtt ttagtagttg tttcggtttt agtgctttgc ccagcacttt ctgagactgg 151200
gattgcttta tttaaatcct ttgcatctac tactatttct tttacactaa tcataataat 151260
ccttaattaa caccggtggc atggaaaatt ccaggagccg ttgtacttgt tacaggggtc 151320
atattctgga ctacggtatt ctttttgacg acattatttg tgttactaat cgccgctacc 151380
ggttgctgtt gtttagattc agaagcacgt cctttctcta ttgactgaac ttgttttgct 151440
tcaggagatt tagtcgaaga ttcaggctta actgtcgtct gagccttttt ggcttcagcc 151500
attttattat ttagcttttc aaatctagca tctaattcct ttttaacaac aggagtttta 151560
ttaagttcag ggtctttaat aagtttactt aaatcagcat aagacttctc gacgttttta 151620
gcattttctg gattagtcat atcgatttta tcgatataat cctcaaatct aactagtgcc 151680
gcacgagttt cattagcttt tatatacgcc tctttacgct cctcttcagg taactctttt 151740
aattttgccg attccgcagc acgctcatcg cttgtactaa actcttcttt attgtcatta 151800
ccacgaaccc agttagtaac gaatgttttg ccgcgttgta acatatcaag acctttagaa 151860
acggttccta attcaccatc gtcacgcttc atttgatatt tagcgacttt ctcttggtct 151920
tctttcttta atgtgttccc agtagtttct tggaatcctt ccaaagcacg tccttctatt 151980
tcgtctgcgg tatcaccaaa acctatagca cgcaatatag acgcagagag tttagccatt 152040
cctaattgaa ttagttcacc taagttcatt aatgctgttc ctacaccttt gacaatagca 152100
acggttaaac caccccagtc tccagcttcc cacaattgtt ttatcgagtc aatagaagtg 152160
aatatatcac ttaagaattt accccactct ttagcttcat cggagaattt agtaaagttt 152220
tcatcaaata aatcccaggc agaagtgaac ttgtctgtcc aatatttgaa atggactatc 152280
aataaatcaa taccgataac aataccaaga ataagtgcgg ccatttttgc tgcttcaata 152340
gcagccgtta tagtgtattt gaaaagcatt ccagcaattc tgtctgaaat tgatattgat 152400
ttattaaacc cggcttgaac tgttttggtg agcattgcga ttttatcgct caatttaaag 152460
ctaattccgc ctttagaatc ggaagtagaa ttagcacttt cttgaaccgg agccgggaag 152520
aaatcttcgt ctggcttatt atcaatcttt tcaggtgtag gtaatgcttt aaacagctca 152580
```

```
tcataagttt cattctcaac cactttaaca ggtattgcgt tctcaattac ttcaagagag 152640
gtgccgcctg tattttgaat agcggtagat gtttgtaatt tttgctctaa taatgtagct 152700
aatcggtcta acttggagct tattgcacta gaaacttcgt ttatactttt agtgacttca 152760
gtttgttttt caataacttc tgcgataagc tctgtgcctt cagcagtatt atctgtcgaa 152820
ttctttaagt ctccaattga ttcaataatt ccgttgcctt tatcttctac actttgtgat 152880
gtgagttcag acgcggcttg gacatcgtct agttttgatg aaatgttatt caatgcttct 152940
aatgaatcag tagctgctgt tgcagctact ttttgtggtt tattatcggc aatgacctta 153000
tttctacgca tggatttcat ttcttcaggt ttcattcaag caatccaata atttctgcta 153060
taccettaat agggccatta gggcctggaa tagcaatagt tgtcgaaagg tcttctgccc 153120
atttgattac aaaagcaggc atctcaagga aagaaatttc tttctcttcg tcattaactt 153180
ttattaagca atttgatagc atttcactga ttgtagcgaa ttgttcaaat ttgcctggtg 153240
gtctaaaata aaaagtatta ccttgaaatt ggaattctgt tcgttggcat acatagacgt 153300
catctagttt ataagtgaat ccatcttttt caacttcaga cttaagtttg ttattaaatt 153360
ccaatatgtg tagacatgca aaatcaaaat ctgcgggact catattttta caaatagaat 153420
cagctaagat tttcatgttt tcgtcaggac ctttaacgtc ctttaaaaga ttataatgtt 153480
tgagccctaa tttaggaatc attacctttt tattagactg tggtagaatt attttcttta 153540
gaggtagaat cagatttaag ttcattttta accttaactg ggttaacagg ttctaacacc 153600
attgagttgg taaacatgta cagatgagtt tgtgagttgt tatttgataa ctcatgaata 153660
acttcatcca cgtaaaattc ggatttgaat tggttctttt ggtcaacaaa tataatttta 153720
gtagcaggcg ttatgttaaa attacctgta gtagtgcatt tagcatatcc gtcatattga 153780
gccattgtct gaagacgact tgcttcttca aatccattac gataggtcat ttcggaatat 153840
ccgccagatc ttgacacaag aatagcatta tcaccatcac ctgtaacaat aactggaata 153900
gatgtatcta aaaatgaatg ggcgaatatc gtggcgtttt taatagggtc tcttgtaaat 153960
tggttggctt tagtcatcca ggtaaaatcc catactaatg gatactcaag ctcttgaata 154020
tactgaccta cagtatttgg ctcacctaca atcatcttaa tgccttcctg accaataaga 154080
gtatcgtagt caatcatgtt tacgcctaaa atatcttgcc atacgaatac gaacttatca 154140
ctcgctgtag caagtcctaa ttctctgaca tatgccaaat aatcatcaaa tgtgcttgtc 154200
caaggaatat caggaacata agcattaata gtgtttattg gcggagtaat taacgtacgg 154260
tctttatata tgacacctaa catttcacgt atagattcgc ctgcgtccga gaagaatgga 154320
cgcccaaatt taaggttctc tatagaatgt attgttccaa gctcaattgc aataatattg 154380
tcaccttttg agtccacaga cacagaataa tgtctacatc cataaattcg agttctaact 154440
tggagaggtg tgtttgaatt tgaaacagag atttgaacta tctgtctacc gtccatttta 154500
gtgtggatgt ttttagtgtc ataaaattga agaatccctt catttcttcc atatagcgaa 154560
tctcgcatgg ttaaagttgt tattgttgct gcgagttcaa cgtatctatt ttcttgccaa 154620
gccgaataat cttgatataa tttaacgctt aagttaggat atcctggacg ttggaatact 154680
gtcatttttt atggtccttt tctactaatg ttaaagcaat accacgttca acaggaatca 154740
tttgcataat agaatccaat gtgtattgac tctttactag tgaatggttt atctgataga 154800
atgtaaaaat ctcatcaggg ttaactaaca atttaaaaac ctctaagata tcagtatatg 154860
ttttaacatg acgttcacaa caacctaatc taagggtcaa attaataggg ttcatagaag 154920
caataacctt ctcgagcgag tcaatgtcta ttgcttctat tacttggatt tggttctctt 154980
```

cagtcaaatc attccatggg taccattcat cattataata tatttctttt atgttttcac 155040
ttatcattaa tgctttatta tcataaaact tttcagggaa agaaaaacgt atttttatac 155100
cagcaacatc aagttcaggt tcgactagtt ctttttgata tatctcaaat ggtgcagttt 155160
tttctttaga gcatttaggg caagtgaaaa taacgggaac ttttgttttg cctatagagc 155220
ctgcaaaaac ttgcaagaat ataaatggtt gccatgtttt agggtactcg ccaaaataat 155280
catcaatcag atcggcaatt atttcttttt gttcttgcgg cgaacgatgt tcgatatcat 155340
ttctaactag taaaaagtct ctataatccg ccacagtgaa cggcttaaaa cgatgaacac 155400
catccggtaa tttacaacga attatattag ccataattac tccttttcta ttatttataa 155460
atactcaata aaggagttaa catgtacaaa tatacgttta ccgtacgttt aggcgataaa 155520
gaagtgaatt gtagagcctt tactttaaaa gaatatttag gactcatagg tgcgcgggct 155580
accggtacta ttgaatcggc agtgaacaat attatcacta attgctctaa cgctaaaaac 155640
ttgactaaac aagaagcaga gctattgttg gtaaatctgt gggcacattc attaggtgaa 155700
gtgaatcaag aacacacctg gaattgttcc tgtgggcatt catttcaagt ctatatgaat 155760
ttattgcaca ctcaattaga tgaacaggcc gatccctggt attcgttcag tggtattaaa 155820
attaagttcc gtcaacctaa attatttgac gataaaaata tcgcattaat gattgcttca 155880
tgtattgagg ccgtttttgt caatggagag tccatccctg ttgaagattt aactgaagca 155940
gaaataaacg acctttacgg ccttataaca gaagatgaca tgatcaatat taaaaatctt 156000
ttagtatcgc catcaattta tctggcaaca cctattaaat gtcccaaatg tggggcgtca 156060
cacgttcaca caatacgagg cctcaaagaa ttctttgagt tactataatg tctaatatca 156120
ataaacttta ttcagatatc gacccagaaa tgcgtatgga ttggaacaag gacgttgctc 156180
gttctgtagg acttcgttct attaaaaata gtcttcttgg catagtgaca actagaaaag 156240
gctcacgccc cttcgaccct gaatttggat gcgatttggt cgacgaactt ttcgagaaca 156300
tgacaccact tacagccgat acgattgagc gtaatatcca ggcagctgtt cgtaactatg 156360
agccacgcat cgacaaactt tctgtaagtg taacgccagt atatgatgac tatacggtta 156420
tagtagagat tagattttcg gtcgtagaca accctgacga tattgaacaa attaaacttc 156480
agttagcgtc aagcaataga gtgtaatgct tcaaggcaac ctatgtataa tggttttagg 156540
tccttccgat acagccggga gattattagt taaaagagag aacattatga agctggaaga 156600
tttacaggaa gagttagacg cagacttagc tattgatacg acaaagttgc aatatgagac 156660
ggcgaataat gttaggttat acagcaaatg gctacgtaag cactcattta ttcgtaaaga 156720
aatgttgcgt atagagactc agaagaaaac tgctctaaaa gcaagattag actactactc 156780
gggacgaggt gacggtgatg aattcagtat ggaccgatac gagaaatctg aaatgaaaac 156840
tgtcctggct gcagataaag atgtgcttaa aatagagact actttacaat actggggaat 156900
tttacttgag ttctgtagtg gtgcacttga cgcagttaag tctcgtagtt ttgcacttaa 156960
acatatccag gatatgcgag aatttgaagc ggggcaataa tgcgttattc gattgaagat 157020
gcctttaata atgatgaaga atttgaaact gaaattaaat tcttaatgga aaagtatcgt 157080
ctacgtcgcc aggatattcg tattctggca gaccaccctt gtggcgaaga cgtcctttat 157140
attaaaggga agtttgctgg gtacatcgac gagtattttt atacaaaaga tatgggtatc 157200
gatatgtgca tgcgagtgat ataaatagat atgtaatttc aacttaggag gcaatcatgt 157260
cagataagat ttgtgttgtc tgtaaaactc caatcgattc tgcattggtt gttgaaacag 157320
acaaaggtcc agcacatcct ggaccttgtt ataattatgt ccaacaaatg ccggtttcag 157380
aaagttcaga agagcaattg aacgaaaccc aacttttact atagtgttac cttttttgc 157440 ctatggtttt ggcccttcca aaaaggtcgg gccttttta attagaagtc ttcttcctca 157500
tcctcatcat cgccttcaag ttcggcacgc ttacctgcta aggcatccct gacagaaata 157560
tcatctgtat cttttaattc cgtttctttt atacgtttct tataataagc ttccaattct 157620
tcaagccctt ctaaggtatg acaactagca attttaccca tgaattcgtc aatagatgct 157680
tcgtataaaa attgtttaaa ttcaagtacc atttttatct cctaagggcc gaagccctta 157740
taaattaatt gttttcatta catagttaaa tttctcatca gcgtaacgtt ggatacgatc 157800
aatgccgtgt tttaacaagt aattaagatg agtatacttc tttttagtat ttaatgattt 157860
aggttttaca cctgcgtcat cgatgagatc ccaaactgta gcaacagctt tagaaccatg 157920
cttacgaagc acgcgaccta cggtttgaag tacgataatt tttgatttaa caccatgggc 157980
gaaaataaca tgatgaagat tcttgactga aataccagta gagaatactc catatgatgc 158040
gacaataata atgcctttac cattttctgc catgacttta agcgcgttac gtgtttcagt 158100
atcaacttca cctgatacgt aataaacttt ttcgtatcca agctctttaa tagcttcaaa 158160
tatttcttta ccgtgtgtaa cgtgtttaaa cattacaaag gcgttctcgt ctttcttagc 158220
caatttgact gaaagttgag caatccactt tgtacgtcgt tttagcccgg taataatttt 158280
aacttcttct tggtatgttt taccttttaa tttaacagtg aattcgtccg gataacgaag 158340
gaaaatacta ttaatcttaa gctcagttac ttgtccgtct tccattaatt tagacgtgct 158400
aacaggacgg aagatttcgc cgaacatacc tacatactgc attacattgg cctttccgtc 158460
tcttaatgag ccagataaac cgaatttaaa catgcaatta tttaatcctg agatgattga 158520
agaaatactt ttgcctgttg ctaagtggca ttcatcgttc atcatcatac cgaactgaga 158580
gaaccattct ttaggctgct taactaccgt ttgccatgta ccaacaataa ttggagcgtc 158640
atttttagat ttgtctgctt tatcggcacc accaccaatt ttcttaatca tcgaatgact 158700
aaacaagcga taatcaacaa aatcattagc catctgggtt gtcaatgctg ttgtagggac 158760
gataatgaga attttacctt catagttctc tagataatat cgagctaaaa gtgcttggat 158820
tagtgattta cctgctgatg tcggaaggtt taaaattcga cgacgattaa ctagaccttc 158880
gtatactgca tctttttgat accaatgtgg ttcgattttt gtgttgcctg aataaatttc 158940
ttgtttagaa agccatgcgt caaaatcttc cctggtaagg tcttcggtct caaagatttt 159000
agggtcaatc catacagaat aactcatatt gttacagaac ttttttattt gtcctacaag 159060
tccatatggt aacaaacggt tgtaatctaa aagtcgaatt ctaccatccc attgcccata 159120
gcgatatttt gggttaaatt tatacccgtc tgcttcaaag ctaaaaaagt cacgaagttc 159180
gtaaaacgta ctttcgtcgc attcaatgcg cacgtgacta aaatcataaa aatgtacttt 159240
aatgtcagtc atgtcaaatt accatgtaat aaatatagtt atatttataa tgaggaaata 159300
ttatgatcga taaagactat attgaagagt tacgtgctct ttctgataaa aaggaagcca 159360
aagctaaact gtttgaatat gcggaacaat ttggcattag tgttaagaaa acaaaatcat 159420
tcgataatat tgttattgat atcgaagaag ctcttaacgc actggctgat gaaccattac 159480
ctgaaactga tggattatct atcaccgatt taattactgc cgcagatgat gtggacggtg 159540
ttaatttcac caacgaagaa gttaaagaag aagctattct gttgtttgat tctccaacag 159600
aacaagttga agtattagaa gttgtcgaac aagaaaaaga attcgaccat gataaattcg 159660
aagaagcaat tactcaggtt gttgaatctg aaaaagagcc cgagtcagag gtaaataaag 159720
aagtaaattt tgttctgcct gaaaatttta gtcctaccct cattaaatta ggcaaaggcc 159780
cagggtatgt tactgttcct tggtggattt atcagtggat agccgaaaca cctgattgga 159840
aatctcgccc aactagtttt gtgcacgctt ctgctcacca aacgttattt agcttaattt 159900
attatattaa tcgcgatgga tcagttctaa ttcgtgaaac tcgtaattct tcttttgtaa 159960
cattaaaata aggataactt atggctttta cagttgatat aactcctaaa acacctactg 160020
gagttataga tgagactaag cagtttactg ctactcccag tggtgaaact ggaggtggaa 160080
ctattaccta tgcatggagt gtagacggtg ctcctcaagt aggatcggca gaaacttttg 160140
attatgtgtt aaaaggacct gctggaacaa aaacaattaa agttgttgca acaaatacta 160200
ttcctgactc tgaagctgaa acagctgaaa ttagtacaac tattacagtt caaaacaaaa 160260
cacagacaac taccttggca gtaactccta atagtcctcc agcaggagta attggaaccc 160320
cagttcaatt taccgccgcc ttagcttctc aaccatcagg tgcatctgct acgtatcagt 160380
ggcatgtaga tggttctcct gtgagcgaag caactagtgc tacattcaat tacactccta 160440
ctacaagcgg agttaaaaaa atcaagtgtg tagctcaagt aacagcgaca gattatgatg 160500
cactgagcgt tacttctaat gaagtatcat tgacagttaa taagaagaca atgaatccac 160560
aggttgcact gactcctcct tctattaacg ttcagcaaga tgcttcggct acgtttactg 160620
ctaacgtaac tgatgctcct gaagaagcgc aaattgcgta ttcatggaag aaagattctt 160680
ctcctgtaga agggtcaact aacgtataca ccgttgatac atcatctatt ggaagtcaaa 160740
ctattgaagt tactgcaact attactgcaa ctgattacga tagcaaaact attacagcag 160800
aaggtcaagt taaagtgact gataaagttg ctccagaacc agaaggtgaa ttaccttatg 160860
ttcatcctct tccacatcgt acttcagctt acatctggtg cggatggtgg gttatggatg 160920
aaatccaaaa aatgactgaa gaaggtaaag attggaaaac tgaagatcca gatagtaaat 160980
actacctgca tcgttacact cttcagaaga tgttgaaaga ctatccggaa gttgatgttc 161040
aagaatcacg taatggatac atcatccata aaactgcttt agaaactggt atcatctata 161100
cctatccata atcgtaaggg gcttcggccc ctttcttcgt ttttaaagca tacaaacaca 161160
tcttgggatt gatgtataat ggcacaaacc aaataatacg ggattgatta tgagagctga 161220
agttgaagtt tatacattac atgaggcggg attttcattc gtagaaattg ctcaaaaaat 161280
cggtttacaa cctaaagaag ttggattact atggactaaa gccgagacag ctcggtcaaa 161340
gtttaaagca aaagaaaaag ttgtataccg taaacgtttg attaacaaaa aggtgaagaa 161400
atgagttttg cacaggaatt aagagaaagg gccctggcca ctaaagccaa tttgttgaaa 161460
gattttattg ctaacttctc tgtgatggca gagaaagccg ctgacaaagg ccagacacaa 161520
tttacatact atccgtcaaa gaatgattta actatcactg agcaaattgg ggagtggttc 161580
cgagataatg gctttcagta caaaattaat cacgaccagc gtgatgggca ctggatagaa 161640
atcaagttct agtatgcttt acattttttg atggtataat gaatctaggt tctatccatt 161700
caaattaaac atcgggtcgg agatagagtc tctgctaatt attttgatat tattatttat 161760
aatggtgatt tatgtttaag aaatacagca gtcttgaaaa ccactacaac tctaagttta 161820
ttgaaaaact ctacactaat ggtttgacta ccggtgtttg ggtagcacgt gagaaaatcc 161880
atgggaccaa cttctcgtta ataattgaac gtgacaacgt cacatgcgcc aagcgcacag 161940
gccctattct tccagcagaa gatttttatg gttatgaaat cgtactcaag aagtatgata 162000
aagctattaa agccgttcaa gaagtcatgg aaagtatttc aacttcggtg ccggtgtcat 162060
atcaagtctt tggtgaattc gctggtggtg gaatccagaa aggtgttgac tacggtgaaa 162120
aagattttta tgtgttcgat atcatcataa acacggaaag tgatgatact tattatatga 162180
gtgattacga aatgcaagat ttctgtaata cgtttggttt taaaatggca ccaatgcttg 162240
gacgtggcac atttgatgct cttatcatga ttccaaacga ccttgattct gtcttagccg 162300
cttataatgc tactgcgtca gaagaccttg tagaagcaaa taattgtgta tttgatgcta 162360
atgttattgg cgataataca gcagaaggtt atgttctgaa gccttgtttc cctaaatggt 162420
tgccaaacgg tactcgtgta gctattaagt gcaagaactc taaattcagt gaaaagaaaa 162480
agtctgataa gcctattaaa actcaggttc cattaaccga aattgacaaa aacttgcttg 162540
atgttctagc ttgttatgtt acattaaacc gtgttaataa tgtgatttct aagattggga 162600
ctgtaacgcc aaaagatttt ggcaaagtga tgggattgac tgttcaagat attctggaag 162660
aaacttctcg tgaaggtatt gtattaacat catccgataa ttcgaatctt gttaagaaag 162720
aattagtcag aatggtgcaa gatgttctgc gtcctgcatg gattgaatta gtatcataac 162780
gaaaaaggga ccgtaaggtc cctttgtttt attcatcaac gataattttt ggtaatttaa 162840
caccgagtaa aacagacaag tctgaacgtc ctgccatttt atccatgtcc ccaccatcaa 162900
ttactctcgc ttctttttca tcttttgcta ctgtgtaagg attcgcagat aaagcatatc 162960
taaccaataa tccgatagat ggttgcaagc tttctggatc aactacgact ttaaatgcac 163020
cgacatgttc cgggtcatct aaatctactc cttcagtgta tggagcataa aagatggacc 163080
ctacaatttc tttttcgccg atattttcta caacacccac aataacataa tctaacggac 163140
tgttggtatc gcagtaaaga ggtaatccat ttgccaagaa tccataagca ttttgtgaaa 163200
gatacttgtc atcttccggc ttatgtttta accaaccaga agcagcaaga atagcagctg 163260
cacgagctga ggctacacaa aacgttgcag tataagttgt ctctttttga atgtgtgata 163320
ccatttcaca caccattcga tataatgaac gacctgcttc tggagcggat gcatagctca 163380
agtcaataaa tccggtgtca gtaattccag taactttata acgtttcgat acagtaatta 163440
aagactgaag aatatcttta ttaatttcat cagccatttc agtagcaagc aaatcttcta 163500
agaagttagg ggcatcaaat ccattcgctt ccaaatcttg cgctaattca accgtgaggc 163560
cagttttaag tttacgagat ttgactgaag tttgccattt attaatctgg aatcttgcat 163620
cagaaatttc actatcagag ctttcaaatt tgcttgttac cgctgcatct gaaaataacc 163680
gtacctttaa atgaacgact gcaatctgaa gagctaattc tagatcactt tcttgaatat 163740
ctgcaaatgg tgtatcttct aacaccttat agacgatatt attatatttg aaaaaatcac 163800
ctttatttag tgtgtctttt gattcttctg tgagttcggt aattttttct cggtctacat 163860
atccaacttc gcctgcataa gtagcaccag ttttaaatgt gaattcgtta tctgggttaa 163920
gatatttgat accataaaaa gcagcaacag gttgattagt tctttgtgtt gctacaatgt 163980
cagaatatat taatttagtc gtagcgcgag tcaaagcaac gagatttggg cgaccgattg 164040
agttgctagt agacgttgta gattcacgca ataatttttg gattttactc attgcatttt 164100
ttccttatgt gatatagatt atttataaag attgtttaca acgtatttgg tatgtgatac 164160
tatagactta tcaactacag aggagtaaac aaaatgacta aagcacgttt cttacgagat 164220
actttaaaag ttctggaagc tgaagcagtt aagttagtag aaaaatatgg tgcaaaagtt 164280
aatggtaatg ccttcaacaa agtatggatg aaagttgatt ctgaagctcg agctaaaggt 164340
tattgggcca ctgataaact tgcgtcattc aaaaacaaag acggttctcc ggcatatgtc 164400
caagaaggta tgcctaattg gcaaaatatt ttgaaaactt acatcgaaat tgcacagaaa 164460
taaaaccaaa aatgggagac cgaagtctcc caaaataaga tttaatcaat taagattaga 164520
tgccttttac atatacacgg cggaagtaag cgttcttacc aaggctgttc aggatagacg 164580
gcataccgga ctggatgcga gcacctggag cctgcaggga actttcagca aacgggttaa 164640
caccgatacc gtaacgagtt ttaaagccca ttaccggctg gaagttctta ggatcggaac 164700
cacgcagtgg ggtaagtgca acgtaaggag catagtaaat acctgcatcc atttcgttag 164760
cgcctttgta accaacggtg aagtaatcct gtttagcata ctggtcgatg tatacgcggt 164820
atttaccacc aagtacaccg gcaaatacag atttagtagt gtcggtatta aaaccagaag 164880
ccaggccctg tgcagcgtaa gaaataccag tatcaactga agccagtacg ttaactacgt 164940
tacgggaagc gataatgaag ttaccttcac cacgaccggt ttgacgagca atttcaactg 165000
cttctttatc aatctggaac aacagagatt taaagctttc accggcccaa cgagcaccac 165060
ggatatcaat cgggtcctgg aagtcaaata caccagcttt agaacccgga gtcagggtca 165120
taccagattt accaacctgt gcagagtagt taatccaatc aacaacttca cggttgattt 165180
ctagcataat ttctgtagcc agaataccgc tcagttcagc atcagcatcc ataccgtgta 165240
ctgcacggag gtcttgtgct aattcgatag agtaagcagc tttcagctgg cgagatttag 165300
cttcgataac ttgtttatcg atacggaagc ccatttcatt ccatgggtta tcggtagaac 165360
cgttgaaacc ttcctggagt tcagcgatag aagtagccat accttcagcg atttctacca 165420
gtgcaccagc ttccatttgt ttcttaactt ctgcatctaa tttagctgca tcagttgcac 165480
cagaatcaag tgttacgaca gcagaagctt gcagatatac agtaccagtt tcttggaaga 165540
agtgagtata gatatcacct acaacagtag tagtgtcagc agccagagct gggaatttct 165600
tagcagcacc ctgaccagag aacatcgcgt ctggggcata catcggatgg aaagcttctt 165660
tagcgccaac agcgataggg tctttaccat atactgcacg gagagcaaat acctgaccgg 165720
tcgggctgtt cataggctga acaccacaaa tatcaaaagc gatcagatta ggaatagcac 165780
gtcgaaccat acccataact gccggcccaa tttgggttac tgcaccagag gtttgacccg 165840
ctgcgatgtt ctgagcatta taaccatggt caccgccaat ttcagcttcg gtcaagaaag 165900
aaccaaacgc ctgagcgatt ttctcgtctt tatattcagg ggatacttcg aaatcttttt 165960
cctggttttc gaagatttta gcgataatag cctgcttgct attagcgatt tccggcaggc 166020
cttcaccttc cagcagttct ttccatttgt ctacgagctg agctttagtt ttgatagtag 166080
tcatttgtgt taacctttaa attagaaacg agatgcgact ttcgcatata aacttacatt 166140
agaattctgt tctacctgag ttgtggtagt gtcaactgct tcggcaacaa aattaagacc 166200
ggcagcgtca ttgtcaactg tatttatact ttcggtaata tcggcttctt ctttagtaga 166260
acctttaacc atttctacaa tagcagttaa cttagtacca aatgcgtcag aataatccat 166320
accttcaacc aggccaataa ctttttcttt ctgagattca gtcaggtctt ttacgctttc 166380
attaatagcg gtttcacgct gaacgtaatt gatatatgca tcacgtttgg taacttcttc 166440
gaacaaacga gcggtttctt ctttatgttc ggccagctct tcttccattt ctgctacaac 166500
atctacagat tcttctggaa caacaacgtt atgttcaaca aacagttctt tcagaccacc 166560
aagcatggat tcgaacaaat cagctttaat gcctttatca actgcgattt ggttttctgc 166620
gagccattct tttgcaagat ggtccaggaa tttagaagct tgttcagcca attttttatc 166680
agctttctct tcagcatctt ctttagcctt ttcaacttct tcttcggctt tttcggcgat 166740
agctttgata tgagattcag ctagtttgac tgcttcctgc ttaacggtgg cttcgaatac 166800

```
agtgctgaaa ttagctttaa cgtccggaga cagttctact gattcgaaaa cactattaag 166860
agcaactgaa gtctcgatat tctgagcttc tttcaaaagt tgttctttga tcattttagt 166920
gtcctgtggt ttagattaca ttattattta taatgctttt aaactctctg cgagagcttt 166980
aaatgcttcg tcagcactgt ttttggtgat ttccaccgaa ttttctgatt ctgatatttg 167040
tttaggagta acccaagcat ctggagcaga aggtccccat acggcatcta cgccgacggt 167100
taatttaaat ccttcgttca cgatacggta ccctttattg gtgtcggtta aagaaccaag 167160
accacgagag gaaacacctg gaatccaacc agctcgtata ttagcagcta atttatcacc 167220
gggaccatgg tcgccttcaa taattctagc acgtccatat acatcgtttc ctttccacca 167280
catatcttca ataatgatag cggcttgcat agggtcaaca tttgcacgag gtggatggtt 167340
taattctcca agggcttgtt tggttgcaac ttgttcttta atatagtcac ttactgcttt 167400
ttccaaaaca cgtttaggat ataaacgttt atttcggtta acaacctctg cctgaagaaa 167460
aataccttct atataaagcc ctggttttaa gccagaatct tttccatcat gagattccaa 167520
cattggaacg ccatcaataa tctcaccggg ttgaccccaa gtttcaataa gtaactcggg 167580
tttattcatt agcttaatcc taatgcttta cgacgtttaa gagctttttt acgcttacgc 167640
aagcctttaa cttggcctga agggttagct tttttagctt taacgacctt acgagcgatt 167700
tgtctacgtt ttgctttaga aagaccagtt gtttggaacg cgttacgttc acgagtttta 167760
cggtctttag tgcgagtgac ttcaccacga gaagaaacat gtttaacgat aaactcattt 167820
aactgttctt cattaataat ggaagccatt gcaacagcta aatccgtttc agtttcaagc 167880
atgttctcga taatagtatt tatatcgtca atatcgagag cagaagacaa tgcatcgatt 167940
cggccctgtg cttcaggaat aagtgcttcg acattttcga gtaccaattc ataagattca 168000
gggataagat acattattca tcgtcctcat catcttcgtc ttcgtcgtca tcgccttcat 168060
cagcgtcgtc ttcagaagct ttcttttctt cttcaggttc ttcgccttca atcaaaaatt 168120
gagaagcgat ttctgctttg cgtgcttcaa tcaaacgaac cgtttttttct gccattgcac 168180
tttcaaaaaa ctttcgagta gcaacgaggt cgtttgattt aatagcttga attaaatcgt 168240
ccattaaaaa tcctcttgtt cttggtcggg gtcttggaaa cgagcctctt tcgactcttc 168300
ttcaatttgc ttagcctctt gttcaatttc ctcgtcagac atctgaagaa tatctttcat 168360
agctgttctg tgagaaatat atttaccaat aaatggttcg gccatctgaa gcatattaat 168420
gcgacgctcc agaatctcag catcctttaa ttccgagaaa taactatccc gatgaaattt 168480
tatcttaata ttatttattt catcattcca ctcatcttct gtaataattc ctttaagaat 168540
taaattagtt ttaagcgggt ctaggaatat ctcttcaaat ttatgttgca gctcacgaat 168600
aaatttacca aatgacaatt catctcgtgt aatagaagta ccagcatcaa actgtatacc 168660
accttggtca cttggaatac gggtaatagg aatacgtaaa gccatataaa gcgcattacg 168720
gaaccaacgt acatcttcca tatttccagt attatctgca cccggtaatg tgtcaacttc 168780
tgttaccgct ttaccatcac gtcgttgtaa ccaataatct tcggtcatcg acataatatg 168840
ctgctggttt ttaatcttgc ctgtagtagc atcatatgca atacggtttt tcatcgtatt 168900
cataacatgt tgcatatgtt ctgctgcttt tcttgaaggc atattacctg tatcaacgta 168960
ccatacacga cgatcgggag cacgagtaat acgataaatt acgacggcat cttcaagaag 169020
ttttaattgg ttcgctggct taatagcccg atgcaaataa ccgatgatat ttttaccaca 169080
gcaatcaact aaaccagaat gggcataaac aatcgcggct ttagggattt ttatttttgt 169140
gccagcttca tatatgcgtc catcacaagc ataagattcg tgtgatgtgt cataaatgaa 169200
```

atattcttta taacccttga ctattttaac accggcttca gtggttgtaa taacttcacg 169260
gacatattga acttgacgtg ggtctaaacg acgaagctct ttaatacctt ctttagggcg 169320
tttagggtca ataattttat ggaagaaaat tcgagaatcc acgtaccaac gtctaaaatg 169380
atctgaacct ttacgttgga aagataaatg atttaacact tcattaaatt catccaacat 169440
cattgatttg atatttggac taaattttgt gttgtctaaa tttatagaaa cgacttctgt 169500
atcatcttca tacacgatag catcggaaac tatttcagag accgcgttat ccacttcata 169560
gttcgtcatc aaatttcgat acgtatcgat taattcacgg gttgatttga gccctggttc 169620
ttgactaccg aacattctct gaaacatagc attatatgtt tgctgtgctt cattttcaga 169680
tacttcgtat tctttagcgc cgtcgtctaa ttttggtgtg gtgatagatt ctaaattttc 169740
tttttcttgg tctttgtaat cacgttcgtc catttttgcc catggagcaa acaaacttaa 169800
gatattaaat ttcattgtat tctccgaatg ggaattatag ttatatttat atggacttct 169860
ccgtcatcac gggaagctgg ggatttctcc ccaaccagat tattcccacc aatcaagagc 169920
aagagttact tcgaacgttt caatctcgtt attgctgtcc cagtcaagag atacttcacc 169980
aacgttagta ggccacaagc cgacaatttc aacttcttta gtgaccgttt tagcatcacg 170040
agcaaattga cgaacgatag cagtcttttt atattcagca ggtttaccac cggtaatttc 170100
attaccttgt cctgctgcaa taccttgcca atcaacaaat ttctgacgaa tgctatgagc 170160
atcatcgttc attactgtaa tagtccaatc atcgaatgta cgatcacctg ccacgttaat 170220
tttacggttc atataagaaa caggaacctt ttcaacgatc gcagcaggaa gagccgtagc 170280
acgacactgg aagctaaagt tttgcccaag gtaagagatt tctacttcga acaggttagg 170340
gcgagcgaaa tcacctgatt cgaaggcacg agttacgtca tctacaaaca tattagcctc 170400
tgtagtaata tgggcttagg attaaccgga ggcccataga attaattttt aaacgatata 170460
gtatatttat atgggctacc gaaatagccc atcaggcgtc ttattaggca cctacagcac 170520
caattagttc gtcgaaatcg gcaccagttg ctgttgctac aaagttcaac gtaatataat 170580
ttatcgagcg ggctggttgt aagtagaaag tagctacaaa ttcattacgg tcgataactg 170640
ctggggtgtt attggtagta tcacaaacaa ctttaaagtt atatacacca ccgagagctt 170700
taataccctg tagatattga gaagtctctg tacggaaaga agaacgggta aatgcgttgt 170760
tcaattcaaa caggcgatat ttggatgctg aaccaatgtt cgttttaacc atattgaaca 170820
aacgacgaac gttaatacgg tcaaatggtg aaggaacaga agtggcagtt ttatcaccgt 170880
acagaacata cccatcacca ccagtaccag taacagggtt aatagcttcc tgatacaaac 170940
gatcacgctg cggttgacga gtttctattg caagcttaat aacgttaaga atttgaccac 171000
ggttataacc ggctggagac atccaaggct gagaaatatt gtctgtgcga gcacaaagac 171060
cagcaatatc agcagctaat ggaacccagc gattcacatc attatatttg tcatattgat 171120
atttatagtt accgtcaata gcagcgtaag tagaacttac attaaagtta ttatcagtgt 171180
aagttcctga cgcagtacgc caatcaacca gattatcaac tgcacgatta acaggaatac 171240
cgactatagt tgcacgtggc ggtgagcaaa gaaccaagca atcttggcga gaatcaccaa 171300
ttgctacaac atgtttctga actgtagaag caacttctaa agattcacct gcacaagaac 171360
cggcaataaa caactgcgca ttaacagatt cgcggtcagc aaacaaatcc caagcttcca 171420
ttaaatcacc agcgtcaacc gtttcattag atgataagcc gccacccagt ttgattacgc 171480
cagagaaacc ttttggccaa ccttgtgcag tagcgaaaat ataattgctt gcgcctttag 171540

-continued

```
caaagaaatc atcaataaag atattactac cataaatatc gcgttcacca cgcttagtag 171600

aaagaattac gctctgaact acagcatcgt tacgacg                          171637
```